US010918687B2

(12) United States Patent
Xing et al.

(10) Patent No.: US 10,918,687 B2
(45) Date of Patent: Feb. 16, 2021

(54) KAVA DERIVED THERAPEUTIC COMPOUNDS AND METHODS OF USE THEREOF

(71) Applicant: KUALITY HERBCEUTICS LLC, Gainesville, FL (US)

(72) Inventors: Chengguo Xing, Gainesville, FL (US); Stephen Hecht, St. Paul, MN (US); Junxuan Lu, Hershey, PA (US); Pramod Upadhyaya, Atlanta, GA (US); Sharon Murphy, St. Paul, MN (US); Pablo Leitzman, Minneapolis, MN (US); Sreekanth Narayanapillai, St. Paul, MN (US); Silvia Balbo, St. Paul, MN (US)

(73) Assignee: Kuality Herbceutics LLC, Gainesville, FL (US)

(*) Notice: Subject to any disclaimer, the term of this patent is extended or adjusted under 35 U.S.C. 154(b) by 0 days.

(21) Appl. No.: 16/750,812

(22) Filed: Jan. 23, 2020

(65) Prior Publication Data
US 2020/0261529 A1    Aug. 20, 2020

Related U.S. Application Data

(62) Division of application No. 15/035,830, filed as application No. PCT/US2014/065038 on Nov. 11, 2014, now Pat. No. 10,624,943.

(60) Provisional application No. 61/902,635, filed on Nov. 11, 2013, provisional application No. 61/904,791, filed on Nov. 15, 2013.

(51) Int. Cl.
| | |
|---|---|
| *A61K 36/67* | (2006.01) |
| *A61K 31/12* | (2006.01) |
| *A61K 31/353* | (2006.01) |
| *A61K 31/366* | (2006.01) |

(52) U.S. Cl.
CPC ............. *A61K 36/67* (2013.01); *A61K 31/12* (2013.01); *A61K 31/353* (2013.01); *A61K 31/366* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 2,524,107 A | 10/1950 | Hedenburg | |
| 4,511,391 A | 4/1985 | Serban et al. | |
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 5,585,386 A | 12/1996 | Rosenbaum | |
| 5,936,128 A | 8/1999 | Ellsworth et al. | |
| 6,288,109 B1 | 9/2001 | Chatterjee et al. | |
| 6,303,157 B1 | 10/2001 | Ono et al. | |
| 10,584,108 B2 | 3/2020 | Xing | |
| 10,624,943 B2 | 4/2020 | Xing et al. | |
| 2001/0031783 A1 | 10/2001 | Steiner | |
| 2003/0105159 A1 | 6/2003 | McCleary et al. | |
| 2004/0029831 A1 | 2/2004 | Ono et al. | |
| 2006/0121132 A1 | 6/2006 | Asakawa et al. | |
| 2016/0279184 A1 | 9/2016 | Xing et al. | |

FOREIGN PATENT DOCUMENTS

| | | |
|---|---|---|
| CN | 1557388 A | 12/2004 |
| CN | 1263476 C | 7/2006 |
| DE | 2134094 A1 | 1/1972 |
| GB | 2410435 A | 8/2005 |
| WO | 2002091966 A1 | 11/2002 |
| WO | 2005067950 A1 | 7/2005 |
| WO | 2016179587 A1 | 11/2016 |

OTHER PUBLICATIONS

Peterson, LA , et al., "Pyridyloxobutyl DNA adducts inhibit the repair of O6-methylguanine", Cancer Res 53, 2780-2785 (1993).
Peterson, LA , et al., "Quantitation of microsomal alpha-hydroxylation of the tobacco-specific nitrosamine, 4-(methylnitrosamino)-1-(3-pyridyl)-1-butanone", Cancer Res 51, 5495-5500 (1991).
Peterson, LA , et al., "Role of aldehydes in the toxic and mutagenic effects of nitrosamines", Chem Res Toxicol 26, 1464-1473 (2013).
Pittler, MH , et al., "Efficacy of kava extract for treating anxiety: systematic review and meta-analysis", J Clin Psychopharmacol 20(1), 84-89 (2000).
Poe, S , et al., "A Boron-Based Synthesis of the Natural Product (+)-trans-Dihydrolycoricidine", Angew Chem Int Ed 50, 4189-4192 (2011).
Prokopczyk, B , et al., "Effects of dietary 1,4-phenylenebis(methylene)selenocyanate on 4-(methylnitrosamino)-1-(3-pyridyl)-1-butanone-induced DNA adduct formation in lung and liver of A/J mice and F344 rats", Carcinogenesis 17, 749-753 (1996).
Puppala, M , et al., "Pilot in Vivo Structure—Activity Relationship of Dihydromethysticin in Blocking 4-(Methylnitrosamino)-1-(3-pyridyl)-1-butanone-Induced O6-Methylguanine and Lung Tumor in A/J Mice", J Med Chem 60, 7935-7920 (2017).

(Continued)

*Primary Examiner* — Susan Hoffman
(74) *Attorney, Agent, or Firm* — Viksnins Harris Padys Malen LLP

(57) ABSTRACT

Certain embodiments of the invention provide a composition comprising at least two compounds selected from the group consisting of dihydromethysticin, methysticin, dihydrokavain, kavain, desmethoxyyangonin and 11-methoxyyangonin, wherein the composition is substantially free of flavokawain B. Certain embodiments of the invention also provide a method for treating or preventing cancer in a mammal (e.g., a human) in need of such treatment comprising, administering to the mammal a carrier and a compound selected from the group consisting of dihydromethysticin, methysticin, dihydrokavain, kavain, desmethoxyyangonin and 11-methoxyyangonin, wherein the compound is substantially free of other kava extract components.

42 Claims, 37 Drawing Sheets

(56) References Cited

OTHER PUBLICATIONS

Reagan-Shaw, S., et al., "Dose translation from animal to human studies revisited", FASEB J 22, 659-661 (2008).
Rowe, A., et al., "Are mould hepatotoxins responsible for kava hepatotoxicity?", Res 26, 1768-1770 (2012).
Sarris, J., et al., "Kava in the treatment of generalized anxiety disorder: a double-blind, randomized, placebo-controlled study", J Clin Psychopharmacol 33(5), 643-648 (2013).
Sarris, "St. John's wort and Kava in treating major depressive disorder with comorbid anxiety: a randomised double-blind placebo-controlled pilot trial", Hum Psychopharmacol 24, 41-48 (2009).
Sarris, J., et al., "The Kava Anxiety Depression Spectrum Study (KADSS): a randomized, placebo-controlled crossover trial using an aqueous extract of Piper methysticum", Psychopharmacology (Berl) 205, 399-407 (2009).
Savard, J., et al., "Regiospecific syntheses of quinones using vinylketene acetals derived from unsaturated esters", Tetrahedron Lett 20, 4911-4914 (1979).
Shaik, A., et al., "Identification of methysticin as a potent and non-toxic NF-* B inhibitor from kava, potentially responsible for kava's chemopreventive activity", Supplementary Data, 1-9, http://www.sciencedirect.com, XP055375380 (2009).
Shaik, A., et al., "Identification of methysticin as a potent and non-toxic NF-kB inhibitor from kava, potentially responsible for kava's chemopreventive activity", Bioorganic & Medicinal Chemistry Letter, 19, 5732-5736; Supporting Information, 9 pages (2009).
Smissman, E., et al., "The Synthesis of 3-Alkoxy-cis-2-trans-4-unsaturated Acids", J Org Chem 29, 3161-3165 (1964).
Sorrentino, L., et al., "Safety of ethanolic kava extract: Results of a study of chronic toxicity in rats", Phytomedicine 13, 542-549 (2006).
Sreekanth, C., et al., "Dihydromethysticin from kava blocks tobacco carcinogen 4-(methylnitrosamino)-1-(3-pyridyl)-1-butanone-induced lung tumorigenesis and differentially reduces DNA damage in A/J mice", Carcinogenesis 35(10), 2365-2372 (2014).
Sturla, SJ, et al., "Mass spectrometric analysis of relative levels of pyridyloxobutylation adducts formed in the reaction of DNA with a chemically activated form of the tobacco-specific carcinogen 4-(methylnitrosamino)-1-(3-pyridyl)-1-butanone", Chem Res Toxicol 18, 1048-1055 (2005).
Tamura, Y, "Nonsteroidal Antiinflammatory Agents. 1. 5-Alkoxy-3-biphenylylacetic Acids and Related Compounds as New Potential Antiinflammatory Agents", Journal of Medicinal Chemistry 20(5), 709-714 (1977).
Tang, Y, et al., "Flavokawain B, a kava chalcone, induces apoptosis via up-regulation of death-receptor 5 and Bim expression in androgen receptor negative, hormonal refractory prostate cancer cell lines and reduces tumor growth", Int J Cancer 127(8), 1758-1768 (2010).
Tang, S, et al., "Gene expression signatures associated with suppression of TRAMP prostate carcinogenesis by a kavalactone-rich Kava fraction", Mol. Carcinog., doi:10.1002/mc.22469 (2016).
Teschke, R, et al., "Contaminant hepatotoxins as culprits for kava hepatotoxicity—fact or fiction?", Phytother Res 27, 472-474 (2013).
Teschke, R, et al., "Kava hepatotoxicity: a clinical survey and critical analysis of 26 suspected cases", Eur J Gastroenterol Hepatol 20, 1182-1193 (2008).
Teschke, R, et al., "Kava hepatotoxicity: regulatory data selection and causality assessment", Dig Liver Dis 41, 891-901 (2009).
Triolet, J, et al., "Reduction in Colon Cancer Risk by Consumption of Kava or Kava Fractions in Carcinogen-Treated Rats", Nutrition and Cancer 64(6), 838-846 (2012).
Upadhyaya, P, et al., "Comparative levels of O6-methylguanine, pyridyloxobutyl—, and pyridylhydroxybutyl-DNA adducts in lung and liver of rats treated chronically with the tobacco-specific carcinogen 4-(methylnitrosamino)-1-(3-pyridyl)-1-butanone", Drug Metab Dispos 37, 1147-1151 (2009).
Upadhyaya, P, et al., "Quantitation of pyridylhydroxybutyl-DNA adducts in liver and lung of F-344 rats treated with 4-(methylnitrosamino)-1-(3-pyridyl)-1-butanone and enantiomers of its metabolite 4-(methylnitrosamino)-1-(3-pyridyl)-1-butanol", Chem Res Toxicol 21, 1468-1476 (2008).
Upadhyaya, P, et al., "Tumorigenicity and metabolism of 4-(methylnitrosamino)-1-(3-pyridyl)-1-butanol enantiomers and metabolites in the A/J mouse", Carcinogenesis 20, 1577-1582 (1999).
Urban, AM, et al., "Formation and repair of pyridyloxobutyl DNA adducts and their relationship to tumor yield in A/J mice", Chem Res Toxicol 25, 2167-2178 (2012).
Wang, F., et al., "CYP17 gene polymorphisms and prostate cancer risk: a meta-analysis based on 38 independent studies", Prostate 71(11), 1167-1177 (2011).
Xuan, T, et al., "Efficacy of extracting solvents to chemical components of kava (Piper methysticum) roots", Journal of Natural Medicines 62(2), 188-194 (2007).
Yang, X, et al., "Kava extract, an herbal alternative for anxiety relief, potentiates acetaminophen-induced cytotoxicity in rat hepatic cells", Phytomedicine 18, 592-600 (2011).
Zhang, H, et al., "Molluscicidal activity of Aglaia duperreana and the constituents of its twigs and leaves", Fitoterapia 83, 1081-1086 (2012).
Zhou, P, et al., "Flavokawain B, the hepatotoxic constituent from kava root, induces GSH-sensitive oxidative stress through modulation of IKK/NF-kappaB and MAPK signaling pathways", FASEB J 24, 4722-4732 (2010).
Zi, X, et al., "Flavokawain A, a novel chalcone from kava extract, induces apoptosis in bladder cancer cells by involvement of Bax protein-dependent and mitochondria-dependent apoptotic pathway and suppresses tumor growth in mice", Cancer Res 65, 3479-3486 (2005).
CAPLUS, Accession No. 1964:425284, Lefeuvre et al., Document No. 61:25284, 1 page (1964).
CAPLUS, Accession No. 1974:45604, Haensel et al., document No. 80:45604, 2 pages (1973).
CAPLUS, Afarinka et al., document No. 140:423524, 1 pages (2003).
Fan, Q, et al., "A Mild and Efficient Asymmetric Hetero-Diels-Alder Reaction of the Brassard Diene with Aldehydes", Eur J Org Chem, 3542-3552 (2005).
Klohs, M, "Chemistry of Kava", U.S. Public Health Service Publication No. 1645, 126-132 (1967).
U.S. Office Action for U.S. Appl. No. 16/747,327, 16 pages, dated Aug. 6, 2020.
Anke, J, et al., "Kava Hepatotoxicity: Are we any closer to the truth?", Planta Med 70, 193-196 (2004).
Burns, DM, et al., "Do changes in cigarette design influence the rise in adenocarcinoma of the lung", Cancer Causes Control 22, 13-22 (2011).
Chiaverotti, T, et al., "Dissociation of epithelial and neuroendocrine carcinoma lineages in the transgenic adenocarcinoma of mouse prostate model of prostate cancer", Am J Pathol 172(1), 236-246 (2008).
Chinese Office Action, and Search Report for CN Application No. 201480072832.2, 13 pages, (dated Mar. 2019).
Cohen, V, et al., "Chemoprevention of lung cancer", Curr Opin Pulm Med 10, 279-283 (2004).
Crampsie, MA, et al., "Phenylbutyl isoselenocyanate modulates phase I and II enzymes and inhibits 4-(methylnitrosamino)-1-(3-pyridyl)-1-butanone-induced DNA adducts in mice", Cancer Prev Res 4, 1884-1894 (2011).
Disilvestro, RA, et al., "Kava feeding in rats does not cause liver injury nor enhance galactosamine-induced hepatitis", Food Chem Toxicol 45, 1293-1300 (2007).
Fatima, A, et al., "Cytotoxic activity of (S)-goniothalamin and analogues against human cancer cells", Bioorganic & Medicinal Chemistry 14(3), 622-631 (2006).
Fujii, K, et al., "Structure-Activity Relations for Methylenedioxyphenyl and Related Compounds on Hepatic Microsomal Enzyme Function, as Measured by Prolongation of Hexobarbital Narcosis and Zoxazolamine Paralysis in Mice", Toxicology and Applied Pharmacology 16, 482-494 (1970).
Fujii, K, et al., "Stucture-activity relations for methylenedioxyphenyl and related compounds on hepatic microsomal enzyme function, as measured by prolongation of hexobarbital narcosis and zoxazolamine

(56) References Cited

OTHER PUBLICATIONS paralysis in mice", Chemical Abstract Accession No. 1970:402132, Document No. 73:2132, 2 pages (1970).
Greenberg, NM, et al., "Prostate cancer in a transgenic mouse", PNAS 92(8), 3439-3443 (1995).
Guo, L, et al., "Analysis of gene expression changes of drug metabolizing enzymes in the livers of F344 rats following oral treatment with kava extract", Food Chem Toxicol 47, 433-442 (2009).
Guo, L, et al., "Gene expression profiling in male B6C3F1 mouse livers exposed to kava identifies—changes in drug metabolizing genes and potential mechanisms linked to kava toxicity", Food Chem Toxicol 48, 686-696 (2010).
Hecht, SS, "Biochemistry, biology, and carcinogenicity of tobacco-specific N-nitrosamines", Chem Res Toxicol 11, 559-603 (1998).
Hecht, SS, et al., "Chemoprevention of lung carcinogenesis in addicted smokers and ex-smokers", Nat Rev Cancer 9, 476-488 (2009).
Hecht, SS, "Lung carcinogenesis by tobacco smoke", Int J Cancer 131, 2724-2732 (2012).
Hecht, SS, "Progress and challenges in selected areas of tobacco carcinogenesis", Chem Res Toxicol 21, 160-171 (2008).
Hou, J, et al., "Structure-based optimization of click-based histone deacetylase inhibitors", European Journal of Medicinal Chemistry 46, 3190-3200 (2011).
Huan, Y, et al., "Research Progress on Kava", Chinese Journal of Tropical Agricultural 30(11), 68-71, (2010). [English Abstract].
Huss, WJ, et al., "Origin of androgen-insensitive poorly differentiated tumors in the transgenic adenocarcinoma of mouse prostate model", Neoplasia 9(11), 938-950 (2007).
Jaffe, H, et al., "In Vivo Inhibition of Mouse Liver Microsomal Hydroxylating Systems by Methylenedioxyphenyl Insecticidal Synergists and Related Compounds", Life Sciences 7, Part 1, 1051-1062 (1968).
Jaffe, H, et al., "Invivo inhibition of mouse liver microsomal hydroxylating systems by methylenedioxyphenyl insecticidal synergists and related compounds", Chemical Abstract Accession No. 1969:2714, Document No. 70:2714, 1 page (1969).
Jhoo, Jin-Woo, et al., "In Vitro Cytotoxicity of Nonpolar Constituents from Different Parts of Kava Plant (*Piper methysticum*)", J Agric Food Chem 54, 3157-3162 (2006).
Johnson, T, et al., "Chemopreventive Effect of Kava on 4-(Methylnitrosamino)-1-(3-pyridyl)-1-butanone plus Benzo [a]pyrene-Induced Lung Tumorigenesis in A/J Mice", Cancer Prev Res 1, 430-438 (2008).
Johnson, T, et al., "Lung Tumorigenesis Suppressing Effects of a Commercial Kava Extract and Its Selected Compounds in A/J Mice", American Journal of Chinese Medicine, vol. 39 (4), 727-742 (2011).
Jyothi, D, et al., "An efficient synthesis of some 5-substitutued-3-methyl-2-cyclohexen-1-ones using microwaves", Indian Journal of Chemistry 47B, 630-632 (2008).
Kava Kava, "Summary of Data for Chemical Selection", ntp.niehs.nih.gov/ntp/htdocs/chem._background/exsumpdf/kava_508.pdf, 13 pages (1998).
Lao, Y, et al., "Formation and accumulation of pyridyloxobutyl DNA adducts in F344 rats chronically treated with 4-(methylnitrosamino)-1-(3-pyridyl)-1-butanone and enantiomers of its metabolite, 4-(methylnitrosamino)-1-(3-pyridyl)-1-butanol", Chem Res Toxicol 20, 235-245 (2007).
Lao, Y, et al., "Quantitation of pyridyloxobutyl DNA adducts of tobacco-specific nitrosamines in rat tissue DNA by high-performance liquid chromatography-electrospray ionization-tandem mass spectrometry", Chem Res Toxicol 19, 674-682 (2006).
Laporte, "Neurocognitive effects of kava (*Piper methysticum*): a systematic review", Hum Psychopharmacol 26, 102-111 (2011).

Lebot, V, et al., "Detection of flavokavins (A, B, C) in cultivars of kava (*Piper methysticum*) using high performance thin layer chromatography (HPTLC)", Food Chem 151, 554-560 (2014).
Leitzman, P, et al., "Kava blocks 4-(methylnitrosamino)-1-(3-pyridyl)-1-butanone-induced lung tumorigenesis in association with reducing O6-methylguanine DNA adduct in A/J mice", Cancer Prev Res (Phila), 7(1), 86-96 (2014).
Li, Y, et al., "Methysticin and 7,8-Dihydromethysticin are Two Major Kavalactones in Kava Extract to Induce CYP1A1", Toxicological Sciences 124(2), 388-399 (2011).
Lin, E, et al., "Flavokawain B inhibits growth of human squamous carcinoma cells: Involvement of apoptosis and cell cycle dysregulation in vitro and in vivo", J Nutr Biochem 23, 368-378 (2012).
Liu, L, et al., "Reduced lung tumorigenesis in human methylguanine DNA—methyltransferase transgenic mice achieved by expression of transgene within the target cell", Carcinogenesis 20, 279-284 (1999).
Loechler, EL, et al., "In vivo mutagenesis by O6-methylguanine built into a unique site in a viral genome", Proc Natl Acad Sci 81, 6271-6275 (1984).
Magar, K et al., "Ruthenium(II)-Catalyzed Protocol for Preparation of Diverse $\alpha,\beta$- and $\beta,\beta$-Dihaloenones from Diazodicarbonyls", Adv Synth Catal 356, 3422-3432 (2014).
Malkinson, "Primary lung tumors in mice as an aid for understanding, preventing, and treating human adenocarcinoma of the lung", Lung Cancer 32, 265-279 (2001).
Martin, AC, et al., "Measuring the chemical and cytotoxic variability of commercially available kava (*Piper methysticum* G. Forster).", PLoS One 9(11), e111572, 7 pages (2014).
Morse, MA, et al., "Effects of aromatic isothiocyanates on tumorigenicity, O6-methylguanine formation, and metabolism of the tobacco-specific nitrosamine 4-(methylnitrosamino)-1-(3-pyridyl)-1-butanone in A/J mouse lung", Cancer Res 49, 2894-2897 (1989).
Morse, MA, et al., "Effects of indole-3-carbinol on lung tumorigenesis and DNA methylation induced by 4-(methylnitrosamino)-1-(3-pyridyl)-1-butanone (NNK) and on the metabolism and disposition of NNK in A/J mice", Cancer Res 50(9), 2613-2617 (1990).
Murphy, SE, et al., "Effects of phenobarbital and 3-methylcholanthrene induction on the formation of three glucuronide metabolites of 4-(methylnitrosamino)-1-(3-pyridyl)-1-butanone, NNK", Chemico-Biological Interactions 103 (3), 153-166 (1997).
Narayanapillai, S, et al., "Dihydromethysticin from kava blocks tobacco carcinogen 4-(methylnitrosamino)-1-(3-pyridyl)-1-butanone-induced lung tumorigenesis and differentially reduces DNA damage in A/J mice", Carcinogenesis vol. 35(10), 2365-2372 (2014).
Narayanapillai, S, et al., "Flavokawains A and B in Kava, not Dihydromethysticin, Potentiate Acetaminophen-Induced Hepatotoxicity in C57BL/6 Mice", Chemical Research in Toxicology 27, 1871-1876 (2014).
National Toxicology Program, "Toxicology and carcinogenesis studies of kava kava extract (CAS No. 9000-38-8) in F344/N rats and B6C3F1 mice (Gavage Studies).", National Toxicology Program Tech Rep Ser (571), 1-186 (2012).
Ni, W, et al., "Quantitation of 13 heterocyclic aromatic amines in cooked beef, pork, and chicken by liquid chromatography-electrospray ionization/tandem mass spectrometry", Journal of Agricultural and Food Chemistry, 56 (1), 68-78 (2008).
Nishikawa, A, et al., "Induction of colon tumors in C57BL/6J mice fed MeIQx, IQ, or PhIP followed by dextran sulfat; sodium treatment", Journal of Society of Toxicology 84(2), 243-248 (2005).
O'Donnell, EP, et al., "Quantitative analysis of early chemically-induced pulmonary lesions in mice of varying susceptibilities to lung tumorigenesis", Cancer Lett 241, 197-202 (2006).
Patent Cooperation Treaty, International Searching Authority, Search Report and Written Opinion for PCT/US2014/65038, 13 pages, dated Jan. 26, 2016.
Peterson, LA, et al., "O6-methylguanine is a critical determinant of 4-(methylnitrosamino)-1-(3-pyridyl)-1-butanone tumorigenesis in A/J mouse lung", Cancer Res 51, 5557-5564 (1991).
U.S. Appl. No. 16/747,327.

| Figure 29. Effect of different kava treatment schedules on lung tumor incidence and multiplicity induced by NNK in A/J mice at 119 day end points. | | | | | | | |
|---|---|---|---|---|---|---|---|
| Group | No. of mice at termination (initiation) | Body Weight at termination (mean ± SD g/mouse) | Liver weight at termination (mean ± SD g/mouse) | Lung tumors | | | $p^*$ |
| | | | | % of Mice with tumors | Tumors /mouse (mean ± SD) | Reduction in tumor multiplicity (%) | |
| 1 (untreated control) | 10(10) | 26.8 ± 2.7 | 1.24 ± 0.18 | 10 | 0.1 ± 0.3 | -- | -- |
| 2 (carcinogen control) | 40(40) | 23.4 ± 2.2 | 1.01 ± 0.10 | 100 | 17.5 ± 4.8 | -- | -- |
| 3 (kava Day 1 – Day 14) | 15(15) | 22.9 ± 1.5 | 1.04 ± 0.09 | 33 | 0.3 ± 0.5 | 98.9 | <0.01 |
| 4 (kava Day 1 – Day 21) | 15(15) | 23.1 ± 1.7 | 1.04 ± 0.11 | 13 | 0.2 ± 0.6 | 99.4 | <0.01 |
| 5 (kava Day 1 – Day 119) | 15(15) | 21.9 ± 1.9 | 1.09 ± 0.16 | 33 | 0.3 ± 0.5 | 98.9 | <0.01 |
| 6 (kava Day 15 – Day 119) | 15(15) | 22.6 ± 2.6 | 1.02 ± 0.12 | 100 | 13.3 ± 4.3 | 24.1 | <0.05 |
| 7 (kava Day 15 – Day 28) | 15(15) | 23.7 ± 1.8 | 1.06 ± 0.09 | 100 | 15.3 ± 5.4 | 12.7 | >0.05 |
| 8 (kava Day 22 – Day 119) | 15(15) | 21.3 ± 2.1 | 1.03 ± 0.10 | 100 | 16.1 ± 6.3 | 8.2 | >0.05 |
| 9 (kava Day 29 – Day 119) | 15(15) | 21.4 ± 1.1 | 1.03 ± 0.11 | 100 | 15.8 ± 6.2 | 10.1 | >0.05 |
| Note: Female A/J mice in Groups 2-9 were treated with NNK (100 and 67 mg/kg bodyweight on Day 7 and Day 14 respectively) in 0.1 mL saline via i.p. injection. Mice were maintained on AIN-93G diet until Day 21 and then shifted to AIN-93M diet for the duration of the experiment. Kava dose was 5 mg/g of diet. *: Compared with Group 2 by Dunnett's test. | | | | | | | |

FIGURE 30

| Figure 30. Effect of kava on lung tumor incidence and multiplicity induced by NNK in A/J mice at 25 weeks (175 days) and 34 week (238 days) time point. | | | | | | | | |
|---|---|---|---|---|---|---|---|---|
| | Group | No. of mice at termination (initiation) | Body Weight at termination (mean ± SD, g/mouse) | Liver weight at termination (mean ± SD g/mouse) | Lung tumors | | | $p^*$ |
| | | | | | % of Mice with tumors | Tumors/mouse (mean ± SD) | Reduction in tumor multiplicity (%) | |
| 25. week | 1 (untreated control) | 5(5) | 27.5 ± 3.8 | 1.19 ± 0.16 | 0 | 0.0 ± 0.0 | -- | -- |
| | 2 (carcinogen control) | 23(25) | 26.4 ± 2.9 | 1.11 ± 0.19 | 100 | 18.1 ± 5.1 | -- | -- |
| | 3 (kava at 5 mg/g diet) | 15(15) | 25.6 ± 2.3 | 1.11 ± 0.18 | 27 | 0.3 ± 0.5 | 98.5 | <0.01 |
| 34. week | 4 (untreated control) | 4(5) | 30.8 ± 2.7 | 1.25 ± 0.05 | 25 | 0.5 ± 1.0 | -- | -- |
| | 5 (carcinogen control) | 25(25) | 27.1 ± 3.0 | 1.16 ± 0.16 | 100 | 26.5 ± 7.8 | -- | -- |
| | 6 (kava at 5 mg/g diet) | 15(15) | 27.2 ± 3.9 | 1.06 ± 0.13 | 90 | 1.1 ± 0.6 | 97.7 | <0.01 |
| Note: Female A/J mice in Groups 2, 3, 5, and 6 were treated with NNK (100 and 67 mg/kg bodyweight on Day 7 and Day 14 respectively) in 0.1 mL saline via i.p. injection. The mice were maintained on AIN-93G diet until Day 21 and then shifted to AIN-93M diet for the duration of the experiment. Kava treatment at a dose of 5 mg/g of diet was between Day 1 – Day 14. *: Compared between Groups 2 and 3 and between Groups 5 and 6. | | | | | | | | |

FIGURE 31

Figure 31. Effect of bolus kava via daily gavage on lung tumor incidence and multiplicity induced by NNK in A/J mice.

| Group | No. of mice at termination (initiation) | Body Weight at termination (mean ± SD, g/mouse) | Liver weight at termination (mean ± SD g/mouse) | Lung tumors | | | |
|---|---|---|---|---|---|---|---|
| | | | | % of Mice with tumors | Tumors/mouse (mean ± SD) | Reduction in tumor multiplicity (%) | $p^*$ |
| 1 (untreated control) | 5(5) | 24.1 ± 4.4 | 1.05 ± 0.17 | 20 | 0.2 ± 0.4 | -- | -- |
| 2 (carcinogen control) | 5(5) | 22.9 ± 3.3 | 0.92 ± 0.14 | 100 | 16.6 ± 3.1 | -- | -- |
| 3 (20 mg kava daily Day 6 – Day 15) | 5(5) | 21.7 ± 1.6 | 0.93 ± 0.12 | 40 | 0.4 ± 0.5 | 98.8 | <0.01 |
| 4 (20 mg kava daily Day 6 – 8 and 13 – 15) | 5(5) | 21.7 ± 1.7 | 0.89 ± 0.08 | 0 | 0.0 ± 0.0 | 100 | <0.01 |

Note: Female A/J mice in Groups 2-4 were treated with NNK (100 and 67 mg/kg bodyweight on Day 7 and Day 14 respectively) in 0.1 mL saline via i.p. injection. The mice were maintained on AIN-93G diet until Day 21 and then shifted to AIN-93M diet for the duration of the experiment. The mice were given cottonseed oil (0.2 mL) via gavage once a day or kava (20 mg) in cottonseed oil (0.2 mL) on the specified days. *: Compared with Group 2 by Dunnett's test.

FIGURE 32

Figure 32. Dose-response effect of kava and different kava fractions on lung tumor incidence and multiplicity induced by NNK in A/J mice.

| Group | No. of mice at termination(initiation) | Body Weight at termination (mean ± SD, g/mouse) | Liver weight at termination (mean ± SD g/mouse) | Lung tumors | | | |
|---|---|---|---|---|---|---|---|
| | | | | % of Mice with tumors | Tumors/mouse (mean ± SD) | Reduction in tumor multiplicity (%) | $p^*$ |
| 1 (untreated control) | 5(5) | 24.3 ± 2.7 | 1.08 ± 0.17 | 20 | 0.2 ± 0.4 | -- | -- |
| 2 (carcinogen control) | 25(25) | 23.5 ± 1.9 | 0.94 ± 0.15 | 100 | 16.0 ± 5.2 | -- | -- |
| 3 (kava at 5 mg/g diet) | 15(15) | 24.0 ± 3.4 | 1.00 ± 0.13 | 13 | 0.1 ± 0.4 | 100 | <0.01 |
| 4 (kava at 2.5 mg/g diet) | 15(15) | 23.3 ± 2.0 | 1.00 ± 0.12 | 27 | 0.3 ± 0.5 | 99.4 | <0.01 |
| 5 (kava at 1.25 mg/g diet) | 15(15) | 23.1 ± 1.5 | 0.89 ± 0.09 | 20 | 0.2 ± 0.4 | 100 | <0.01 |
| 6 (Fraction A at 2.5 mg/g diet) | 15(15) | 23.3 ± 2.6 | 1.00 ± 0.10 | 100 | 12.0 ± 5.0 | 25.3 | <0.01 |
| 7 (Fraction B at 2.5 mg/g diet) | 15(15) | 23.4 ± 2.9 | 0.97 ± 0.10 | 7 | 0.1 ± 0.5 | 100 | <0.01 |
| 8 (Fraction C at 2.5 mg/g diet) | 15(15) | 22.7 ± 2.2 | 0.95 ± 0.11 | 93 | 3.5 ± 2.5 | 70.2 | <0.01 |

Note: Female A/J mice in Groups 2-8 were treated with NNK (100 and 67 mg/kg bodyweight on Day 7 and Day 14 respectively) in 0.1 mL saline via i.p. injection. The mice were maintained on AIN-93G diet until Day 21 and then shifted to AIN-93M diet for the duration of the experiment. Kava modality treatment was between Day 1 – Day 14. *: Compared with Group 2 by Dunnett's test.

FIGURE 33

Experimental Design

| Group# | Mouse Genotype | Group ID | Dietary Treatment | Enrolled number of mice |
|---|---|---|---|---|
| 1 | TRAMP | Vehicle | Vehicle-diet | N=24<br>Kill 7 mice @16 weeks<br>Kill 17 mice @28 weeks |
| 2 | TRAMP | Kava | Kava Fraction B, 0.4% diet @8 weeks of age | N=24<br>Kill 7 mice @16 weeks<br>Kill 17 mice @28 weeks |
| 3 | Wild Type | Vehicle | Vehicle-diet | N=10<br>Kill 5 mice @16 weeks<br>Kill 5 mice @28 weeks |
| 4 | Wild Type | Kava | Kava Fraction B, 0.4% diet @8 weeks of age | N=10<br>Kill 5 mice @16 weeks<br>Kill 5 mice @28 weeks |

FIGURE 34

Prostate Tumors (28 weeks of age)

| Group# | Mouse | Group ID | Visible Tumors | Tumor Incidence |
|---|---|---|---|---|
| 1 | TRAMP | Vehicle | 7 (out of 14 mice) | 50.0% |
| 2 | TRAMP | Kava | 2 (out of 14 mice) | 14.3% |
|  |  |  | $X^2 = 4.09$ | $P<0.05$ ($X^2_{p=0.05}$ 3.84) |

FIGURE 35

Prostate Tumor Weight (g) and lobe location (VP = ventral prostate lobe)

| Rank # | Vehicle group (7/14 mice) | Kava group (2/14 mice) |
| --- | --- | --- |
| 1 | 8.5125 @28wk | 7.9674 @25wk |
| 2 | 1.2266 @28wk | 4.3293 @28wk |
| 3 | 0.9672 (VP)@28wk | |
| 4 | 0.7345 (VP)@28wk | |
| 5 | 0.4022 (VP)@28wk | |
| 6 | 0.0883 (VP)@28wk | |
| 7 | 0.0693 (VP)@28wk | |

FIGURE 36

| Effect of different agents on lung tumor incidence and multiplicity induced by NNK in A/J mice. | | | | | | | |
|---|---|---|---|---|---|---|---|
| Group | No. of mice at termination (initiation) | Body Weight at termination (mean ± SD, g/mouse) | Liver weight at termination (mean ± SD g/mouse) | % of Mice with tumors | Lung tumors Tumors /mouse (mean ± SD) | Reduction in tumor multiplicity (%) | $p^*$ |
| 1 (untreated control) | 5(5) | 23.8 ± 2.5 | 1.07 ± 0.13 | 20 | 0.2 ± 0.4 | - | - |
| 2 (carcinogen control) | 9(10) | 22.6 ± 3.1 | 1.07 ± 0.15 | 100 | 13.9 ± 6.9 | - | - |
| 3 (kava, 1.25mg/g) | 5(5) | 23.7 ± 1.8 | 1.06 ± 0.13 | 80 | 0.8 ± 0.4 | 95.6 | < 0.01 |
| 4 ((+)-DHM, 0.5mg/g) | 5(5) | 23.7 ± 1.5 | 1.08 ± 0.11 | 60 | 0.4 ± 0.5 | 97.1 | < 0.01 |
| 5 ((+)-DHM, 0.05mg/g) | 5(5) | 25.0 ± 0.7 | 1.12 ± 0.05 | 60 | 0.4 ± 0.5 | 97.1 | < 0.01 |
| 6 ((+)-DHK, 0.5mg/g) | 5(5) | 23.2 ± 1.5 | 1.09 ± 0.07 | 100 | 14.8 ± 12.8 | - | > 0.05 |
| 7 ((+)-DHK, 0.05mg/g) | 5(5) | 23.1 ± 0.5 | 1.04 ± 0.04 | 100 | 19.6 ± 5.6 | - | > 0.05 |
| 8 ((±)-DHM, 0.5mg/g) | 5(5) | 23.4 ± 1.5 | 1.07 ± 0.09 | 0 | 0 | 100 | < 0.01 |
| Note: Female A/J mice in Groups 2-9 were treated with NNK (100 and 67 mg/kg bodyweight on Day 7 and Day 14 respectively) in 0.1 mL saline via i.p. injection. Mice were maintained on AIN-93G diet until Day 21 and then shifted to AIN-93M diet for the duration of the experiment. Treatments were between Day 1 and Day 14. *: Compared with Group 2 by Dunnett's test using ONE-WAY ANOVA. | | | | | | | |

KAVA DERIVED THERAPEUTIC COMPOUNDS AND METHODS OF USE THEREOF

RELATED APPLICATIONS

This application is a divisional application of U.S. patent application Ser. No. 15/035,830, now U.S. Pat. No. 10,624,943, which is a National Stage Entry under 35 U.S.C. § 371 of International Patent Application Number PCT/US2014/065038 that was filed on Nov. 11, 2014, which claims priority from U.S. Provisional Application No. 61/902,635 that was filed on Nov. 11, 2013 and U.S. Provisional Application No. 61/904,791 that was filed on Nov. 15, 2013, which applications are herein incorporated by reference.

GOVERNMENT FUNDING

This invention was made with government support under R01-CA142649 awarded by the National Cancer Institute/National Institutes of Health. The government has certain rights in the invention.

BACKGROUND OF THE INVENTION

Lung cancer is the leading cause of malignancy-related mortality because of its high incidence and the lack of effective treatments. Since tobacco usage contributes to 85-90% of its development, tobacco cessation is the most straightforward strategy for reducing lung cancer incidence and mortality. However, because of the addictive nature of nicotine in tobacco, limited progress has been achieved in reducing tobacco usage. An alternative approach is to block or slow down tobacco carcinogen-induced lung cancer development via chemoprevention (Hecht et al., Nat. Rev. Cancer 2009; 9:476-88). Although a number of compounds have been identified as potential chemopreventive agents against lung tumorigenesis in animal models, their moderate in vivo efficacy leaves ample room for improvement and introduces significant challenges for clinical application/evaluation. In addition, there are very limited successes in cancer chemoprevention relative to cancer therapy. Therefore, there is currently an unmet need for additional agents that are useful for treating or preventing cancer.

SUMMARY OF THE INVENTION

Certain embodiments of the invention provide a method, comprising:
a) combining an ethanolic kava extract and silica gel to provide a mixture;
b) evaporating the mixture to provide a silica gel having kava residue adsorbed thereon;
c) loading the silica gel having kava residue adsorbed thereon on a chromatography column to provide a kava-adsorbed silica gel column;
d) eluting the kava-adsorbed silica gel column with a solvent system to provide a first kava extract fraction, a second kava extract fraction, and a third kava extract fraction, wherein the first kava extract fraction consists essentially of non-polar compounds, including flavokawains, the second kava extract fraction consists essentially of kavalactones and flavanones, and the third kava extract fraction consists essentially of polar compounds.

Certain embodiments of the invention provide a second kava extract fraction prepared by a method described herein.

Certain embodiments of the invention provide a composition comprising 11-methoxyyangonin and/or flavanone:

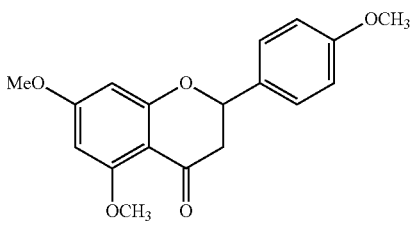 [SMILES: COc1ccc(C2CC(=O)c3c(OC)cc(OC)cc3O2)cc1]

and at least one compound selected from the group consisting of dihydromethysticin, methysticin, dihydrokavain, kavain and desmethoxyyangonin, wherein the composition is substantially free of flavokawain B and/or flavokawain A.

Certain embodiments of the invention provide a composition comprising at least one compound selected from the group consisting of dihydromethysticin, wherein the weight percent of dihydromethysticin in the composition is about 20 to 99%; methysticin, wherein the weight percent of methysticin in the composition is about 10 to 99%; dihydrokavain, wherein the weight percent of dihydrokavain in the composition is about 40 to 99%; kavain, wherein the weight percent of kavain in the composition is about 40 to 99%; desmethoxyyangonin, wherein the weight percent of desmethoxyyangonin in the composition is about 30 to 99%; and 11-methoxyyangonin, wherein the weight percent of 11-methoxyyangonin in the composition is about 20 to 99%.

Certain embodiments of the invention provide a kava extract comprising 11-methoxyyangonin and/or flavanone:

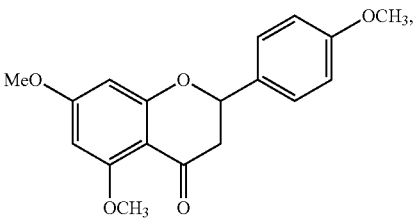

and at least one compound selected from the group consisting of dihydromethysticin, methysticin, dihydrokavain, kavain and desmethoxyyangonin, wherein the extract is substantially free of flavokawain B and/or flavokawain A.

Certain embodiments of the invention provide a kava extract consisting essentially of dihydromethysticin, 11-methoxyyangonin, desmethoxyyangonin, dihydrokavain, kavain, methysticin and flavanone:

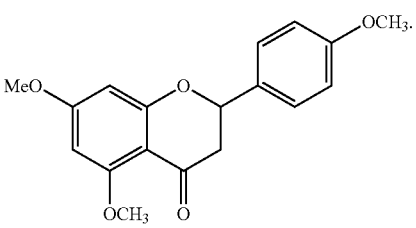

Certain embodiments of the invention provide a pharmaceutical composition comprising a composition or kava extract as described herein and a pharmaceutically acceptable carrier.

Certain embodiments of the invention provide a method for treating or preventing cancer in a mammal in need of such treatment comprising, administering to the mammal dihydromethysticin and a carrier, wherein the dihydromethysticin is substantially free of other kava extract components.

Certain embodiments of the invention provide a method for treating or preventing cancer in a mammal in need of such treatment comprising, administering to the mammal methysticin and a carrier, wherein the methysticin is substantially free of other kava extract components.

Certain embodiments of the invention provide a method for treating or preventing cancer in a mammal in need of such treatment comprising, administering to the mammal dihydrokavain and a carrier, wherein the dihydrokavain is substantially free of other kava extract components.

Certain embodiments of the invention provide a method for treating or preventing cancer in a mammal in need of such treatment comprising, administering to the mammal kavain and a carrier, wherein the kavain is substantially free of other kava extract components.

Certain embodiments of the invention provide a method for treating or preventing cancer in a mammal in need of such treatment comprising, administering to the mammal desmethoxyyangonin and a carrier, wherein the desmethoxyyangonin is substantially free of other kava extract components.

Certain embodiments of the invention provide a method for treating or preventing cancer in a mammal in need of such treatment comprising, administering to the mammal 11-methoxyyangonin and a carrier, wherein the 11-methoxyyangonin is substantially free of other kava extract components.

Certain embodiments of the invention provide a method for treating or preventing cancer in a mammal in need of such treatment comprising, administering to the mammal a composition or kava extract as described herein.

Certain embodiments of the invention provide a method for preventing tumorigenesis, reducing DNA damage, reducing protein damage and/or detoxifying physical or chemical carcinogens in a mammal in need of such treatment comprising, administering to the mammal dihydromethysticin and a carrier, wherein the dihydromethysticin is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal methysticin and a carrier, wherein the methysticin is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal dihydrokavain and a carrier, wherein the dihydrokavain is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal kavain and a carrier, wherein the kavain is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal desmethoxyyangonin and a carrier, wherein the desmethoxyyangonin is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal 11-methoxyyangonin and a carrier, wherein the 11-methoxyyangonin is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal a composition or kava extract as described herein.

BRIEF DESCRIPTION OF THE FIGURES

FIG. 1A. The amount of DNA adducts at different time points after NNK treatment; NNK alone: ■; NNK+kava: ▲). FIG. 1B. Relative amount of DNA adducts in NNK+kava treatment group at different time points after NNK treatment (the amount with kava treatment normalized to that induced by NNK alone at the same time point). FIG. 1C. The amount of DNA adducts with different kava fraction treatment 24 h after NNK treatment. FIG. 1D. Relative amount of DNA adducts by different kava fractions normalized to that induced by NNK alone at the 24 h time point.

FIG. 17A, Chemical structures of five natural kavalactones isolated from Fraction B. FIG. 17B, Their effects on NNK-induced POB adducts and $O^6$-mG adduct. Comparison was made with the NNK treatment group by Dunnett's test when ONE-WAY ANOVA was statistically significant. n=3 each group. *p<0.05 and **p<0.01.

FIG. 18A, Dose-response effect of natural (+)-DHM on NNK-induced $O^6$-mG (a) and three POB adducts (b-d) in comparison to kava, (+)-DHK and synthetic (±)-DHM. FIG. 18B, Dose-response effect of natural (+)-DHM on NNK-induced 7-mG (a) and three PHB adducts (b-d) in comparison to kava, (+)-DHK and synthetic (±)-DHM.

FIG. 18C, Percentage of different DNA adducts from mice treated with (+)-DHM (1 mg/g of diet) relative to that from NNK-treated control mice. For FIGS. 18A and 18B, comparison was made with NNK treatment group by Dunnett's test when ONE-WAY ANOVA was statistically significant. n=3 each group. *p<0.05 and **p<0.01. For FIG. 18C, ONE-WAY ANOVA was not statistically significant.

FIG. 20A, Weekly time-course of bodyweight changes. FIG. 20B, Average daily-food consumption (disappearance) estimated weekly. The weekly bodyweights of the control and (+)-DHM treated mice were analyzed by a two-tailed Student t-test, and none of the comparisons were statistically significant.

FIG. 21A, 8 weeks. FIG. 21B, 17 weeks. p values were given when possible with comparison between the control group (n=5) and the (+)-DHM treatment group (n=10) using a two-tailed Student t-test.

FIG. 24A. Serum ALT and AST. FIG. 24B. The number of mice with different grades of liver lesions. FIG. 24C. The relationships among serum ALT, AST and the grades of liver lesions. For FIG. 24A, comparisons were made with APAP treatment group by Dunnett's test when ONE-WAY ANOVA was statistically significant (n=8-15).

FIGS. 27A & 27B. Serum ALT and AST. Comparisons were made with APAP treatment group by Dunnett's test when ONE-WAY ANOVA was statistically significant (n=5). FIG. 27C. Serum level of ALT and AST from the dead mouse in the high-dose FKA and FKB group with APAP co-treatment. FIG. 27D. Photomicrographs of H&E-stained livers from a control mouse (Panel A) and a mouse treated with FKA and FKB plus APAP (Panel B). Note extensive karyorrhexis (arrow) reflecting acute necrosis of hepatocytes (increased eosinophilia) in mouse treated with FKA, FKB and APAP (Panel B).

FIG. 29. Effect of different kava treatment schedules on lung tumor incidence and multiplicity induced by NNK in A/J mice at 119 day end points.

FIG. 30. Effect of kava on lung tumor incidence and multiplicity induced by NNK in A/J mice at 25 weeks (175 days) and 34 week (238 days) time point.

FIG. 31. Effect of bolus kava via daily gavage on lung tumor incidence and multiplicity induced by NNK in A/J mice.

FIG. 32. Dose-response effect of kava and different kava fractions on lung tumor incidence and multiplicity induced by NNK in A/J mice.

FIG. 33. Experimental design for prostate cancer prevention with TRAMP models.

FIG. 34. Prostate tumors at the age of 28 weeks.

FIG. 35. Prostate tumor weight (g) and lobe location (VP=ventral prostate lobe).

FIG. 36. Effect of different agents on lung tumor incidence and multiplicity induced by NNK in A/J mice.

DETAILED DESCRIPTION

Figure 1A:
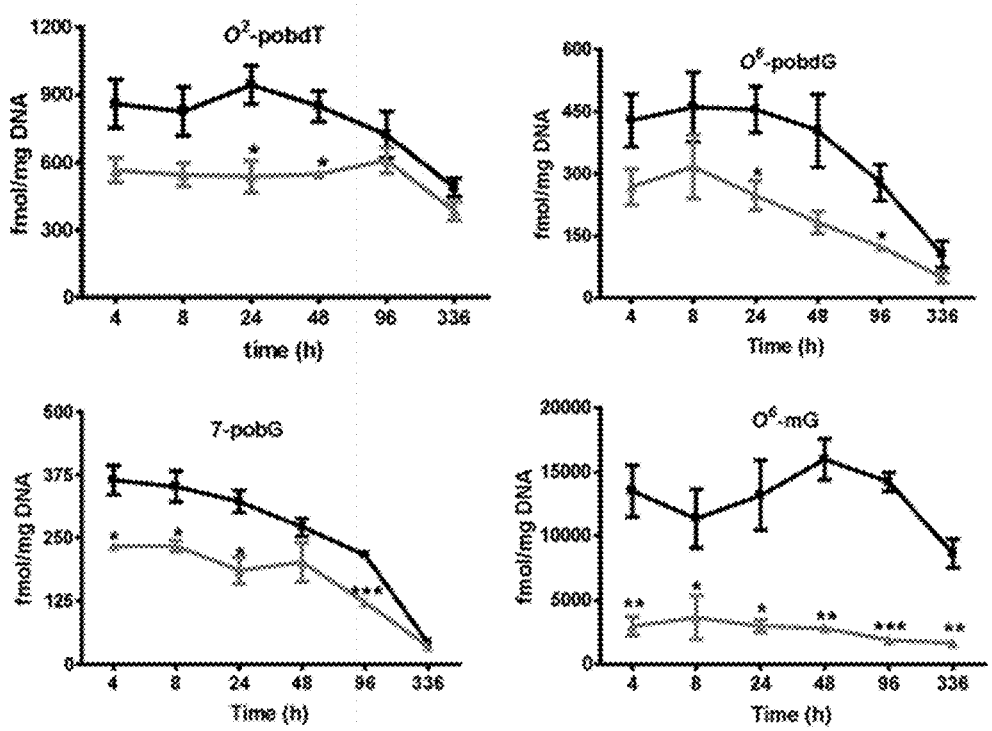
FIGS. 1A-1D. Characterization of the effect of kava and kava fractions on DNA adducts induced by NNK in the lung of A/J mice (n=3 each group): *$p<0.05$; $p<0.01$; *$p<0.001$.

Certain embodiments of the invention provide a composition comprising at least two compounds selected from the group consisting of dihydromethysticin, methysticin, dihydrokavain, kavain, desmethoxyyangonin and 11-methoxyyangonin, wherein the composition is substantially free of flavokawain B and/or flavokawain A.

In certain embodiments, the at least two compounds are dihydromethysticin and methysticin.

In certain embodiments, the at least two compounds are dihydromethysticin and dihydrokavain.

In certain embodiments, the at least two compounds are dihydromethysticin and kavain.

In certain embodiments, the at least two compounds are methysticin and dihydrokavain.

In certain embodiments, the at least two compounds are methysticin and kavain.

In certain embodiments, the at least two compounds are dihydrokavain and kavain.

In certain embodiments, the composition comprises at least three compounds selected from the group consisting of dihydromethysticin, methysticin, dihydrokavain, kavain, desmethoxyyangonin and 11-methoxyyangonin, wherein the composition is substantially free of flavokawain B and/or flavokawain A.

In certain embodiments, the at least three compounds are dihydromethysticin, methysticin and dihydrokavain.

In certain embodiments, the at least three compounds are dihydromethysticin, methysticin and kavain.

In certain embodiments, the at least three compounds are dihydromethysticin, dihydrokavain and kavain.

In certain embodiments, the at least three compounds are methysticin, dihydrokavain and kavain.

In certain embodiments, the composition comprises at least four compounds selected from the group consisting of dihydromethysticin, methysticin, dihydrokavain, kavain, desmethoxyyangonin and 11-methoxyyangonin, wherein the composition is substantially free of flavokawain B and/or flavokawain A.

In certain embodiments, the composition comprises at least five compounds selected from the group consisting of dihydromethysticin, methysticin, dihydrokavain, kavain, desmethoxyyangonin and 11-methoxyyangonin, wherein the composition is substantially free of flavokawain B and/or flavokawain A.

In certain embodiments, the composition comprises dihydromethysticin, methysticin, dihydrokavain, kavain, desmethoxyyangonin and 11-methoxyyangonin, wherein the composition is substantially free of flavokawain B and/or flavokawain A.

In certain embodiments, the composition further comprises flavanone:

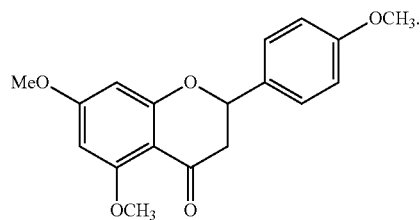 [SMILES: COc1ccc(C2CC(=O)c3c(OC)cc(OC)cc3O2)cc1]

In certain embodiments, the composition is substantially free of flavokawain B.

In certain embodiments, the composition is substantially free of flavokawain A.

In certain embodiments, the composition is substantially free of bornyl ester of 3,4-methylenedioxy cinnamic acid:

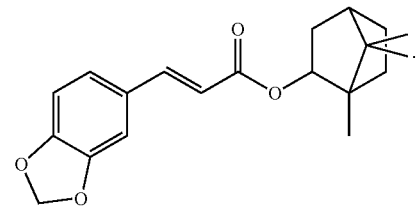 [SMILES: CC1(C)C2CCC1(C)C(OC(=O)/C=C/c1ccc3c(c1)OCO3)C2]

In certain embodiments, the composition is substantially free of bornyl ester of cinnamic acid:

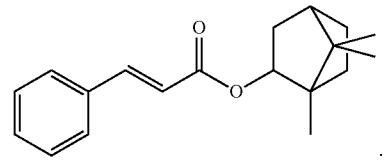 [SMILES: CC1(C)C2CCC1(C)C(OC(=O)/C=C/c1ccccc1)C2]

In certain embodiments, the composition is substantially free of flavanone:

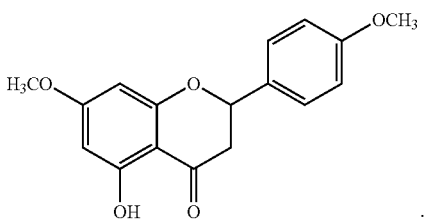 [SMILES: COc1ccc(C2CC(=O)c3c(O)cc(OC)cc3O2)cc1]

In certain embodiments, the composition is substantially free of pinostrobin.

Certain embodiments of the invention provide a composition comprising 11-methoxyyangonin and/or flavanone:

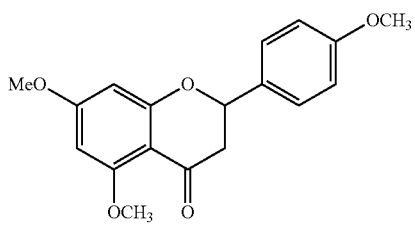 [SMILES: COc1ccc(C2CC(=O)c3c(OC)cc(OC)cc3O2)cc1]

and at least one compound selected from the group consisting of dihydromethysticin, methysticin, dihydrokavain, kavain and desmethoxyyangonin, wherein the composition is substantially free of flavokawain B and/or flavokawain A.

In certain embodiments, the at least one compound is dihydromethysticin.

In certain embodiments, the composition comprises at least two compounds selected from the group consisting of dihydromethysticin, methysticin, dihydrokavain, kavain and desmethoxyyangonin, wherein the composition is substantially free of flavokawain B and/or flavokawain A.

In certain embodiments, the composition comprises at least three compounds selected from the group consisting of dihydromethysticin, methysticin, dihydrokavain, kavain and desmethoxyyangonin, wherein the composition is substantially free of flavokawain B and/or flavokawain A.

In certain embodiments, the composition comprises at least four compounds selected from the group consisting of dihydromethysticin, methysticin, dihydrokavain, kavain and desmethoxyyangonin, wherein the composition is substantially free of flavokawain B and/or flavokawain A.

In certain embodiments, the composition comprises 11-methoxyyangonin.

In certain embodiments, the composition comprises flavanone:

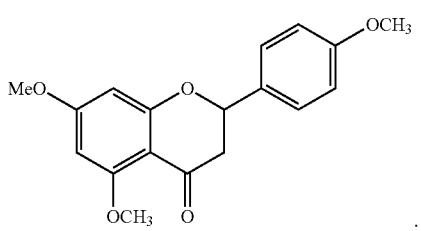 [SMILES: COc1ccc(C2CC(=O)c3c(OC)cc(OC)cc3O2)cc1]

In certain embodiments, the composition comprises 11-methoxyyangonin and flavanone:

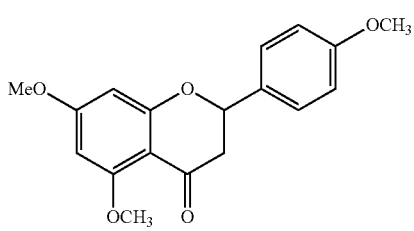

In certain embodiments, the composition is substantially free of flavokawain B.

In certain embodiments, the composition is substantially free of flavokawain A.

In certain embodiments, the composition is substantially free of bornyl ester of 3,4-methylenedioxy cinnamic acid:

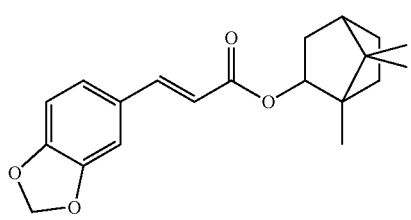

In certain embodiments, the composition is substantially free of bornyl ester of cinnamic acid:

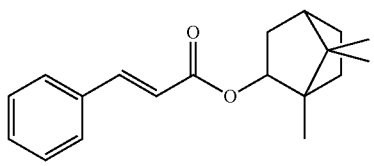

In certain embodiments, the composition is substantially free of flavanone:

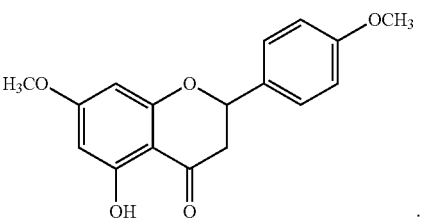 [SMILES: COc1ccc(C2CC(=O)c3c(O)cc(OC)cc3O2)cc1]

In certain embodiments, the composition is substantially free of pinostrobin.

In certain embodiments, the composition is substantially free of methysticin.

Certain embodiments of the invention provide a composition comprising at least one compound selected from the group consisting of dihydromethysticin, wherein the weight percent of dihydromethysticin in the composition is 15±5%; methysticin, wherein the weight percent of methysticin in the composition is 6±5%; dihydrokavain, wherein the weight percent of dihydrokavain in the composition is 30±5%; kavain, wherein the weight percent of kavain in the composition is 29±5%; desmethoxyyangonin wherein the weight percent of desmethoxyyangonin in the composition is 12±5%; and 11-methoxyyangonin wherein the weight percent of 11-methoxyyangonin in the composition is 0.8±0.5%.

In certain embodiments, the at least one compound is dihydromethysticin, and wherein the weight percent of dihydromethysticin in the composition is 15±5%.

In certain embodiments, the at least one compound is kavain, and wherein the weight percent of kavain in the composition is 29±5%.

In certain embodiments, the at least one compound is methysticin, and wherein the weight percent of methysticin in the composition is 6±5%.

In certain embodiments, the at least one compound is dihydrokavain, and wherein the weight percent of dihydrokavain in the composition is 30±5%.

In certain embodiments, the at least one compound is desmethoxyyangonin, and wherein the weight percent of desmethoxyyangonin in the composition is 12±5%.

In certain embodiments, the at least one compound is 11-methoxyyangonin, and wherein the weight percent of 11-methoxyyangonin in the composition is 0.8±0.5%.

In certain embodiments of the invention, the composition comprises at least two compounds selected from the group consisting of dihydromethysticin, wherein the weight percent of dihydromethysticin in the composition is 15±5%; methysticin, wherein the weight percent of methysticin in the composition is 6±5%; dihydrokavain, wherein the weight percent of dihydrokavain in the composition is 30±5%; kavain, wherein the weight percent of kavain in the composition is 29±5%; desmethoxyyangonin wherein the weight percent of desmethoxyyangonin in the composition is 12±5%; and 11-methoxyyangonin wherein the weight percent of 11-methoxyyangonin in the composition is 0.8±0.5%.

In certain embodiments of the invention, the composition comprises at least three compounds selected from the group consisting of dihydromethysticin, wherein the weight percent of dihydromethysticin in the composition is 15±5%; methysticin, wherein the weight percent of methysticin in the composition is 6±5%; dihydrokavain, wherein the weight percent of dihydrokavain in the composition is 30±5%; kavain, wherein the weight percent of kavain in the composition is 29±5%; desmethoxyyangonin wherein the weight percent of desmethoxyyangonin in the composition is 12±5%; and 11-methoxyyangonin wherein the weight percent of 11-methoxyyangonin in the composition is 0.8±0.5%.

In certain embodiments of the invention, the composition comprises at least four compounds selected from the group consisting of dihydromethysticin, wherein the weight percent of dihydromethysticin in the composition is 15±5%; methysticin, wherein the weight percent of methysticin in the composition is 6±5%; dihydrokavain, wherein the weight percent of dihydrokavain in the composition is 30±5%; kavain, wherein the weight percent of kavain in the composition is 29±5%; desmethoxyyangonin wherein the weight percent of desmethoxyyangonin in the composition is 12±5%; and 11-methoxyyangonin wherein the weight percent of 11-methoxyyangonin in the composition is 0.8±0.5%.

In certain embodiments of the invention, the composition comprises at least five compounds selected from the group consisting of dihydromethysticin, wherein the weight percent of dihydromethysticin in the composition is 15±5%; methysticin, wherein the weight percent of methysticin in the composition is 6±5%; dihydrokavain, wherein the weight percent of dihydrokavain in the composition is 30±5%; kavain, wherein the weight percent of kavain in the composition is 29±5%; desmethoxyyangonin wherein the weight percent of desmethoxyyangonin in the composition is 12±5%; and 11-methoxyyangonin wherein the weight percent of 11-methoxyyangonin in the composition is 0.8±0.5%.

In certain embodiments of the invention, the composition comprises dihydromethysticin, wherein the weight percent of dihydromethysticin in the composition is 15±5%; methysticin, wherein the weight percent of methysticin in the composition is 6±5%; dihydrokavain, wherein the weight percent of dihydrokavain in the composition is 30±5%; kavain, wherein the weight percent of kavain in the composition is 29±5%; desmethoxyyangonin wherein the weight percent of desmethoxyyangonin in the composition is 12±5%; and 11-methoxyyangonin wherein the weight percent of 11-methoxyyangonin in the composition is 0.8 f 0.5%.

In certain embodiments, the composition further comprises flavanone:

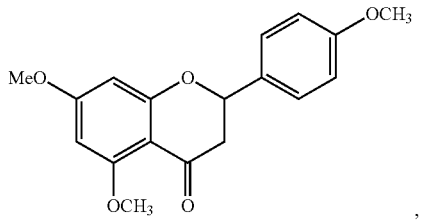 [SMILES: COc1ccc(C2CC(=O)c3c(OC)cc(OC)cc3O2)cc1]

and
wherein the weight percent of the flavanone in the composition is 1±0.5%.

In certain embodiments, the composition is substantially free of flavokawain B.

In certain embodiments, the composition is substantially free of flavokawain A.

In certain embodiments, the composition is substantially free of bornyl ester of 3,4-methylenedioxy cinnamic acid:

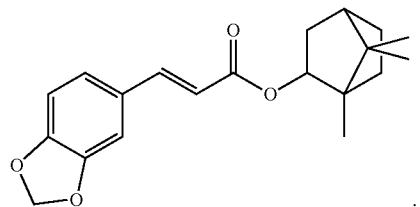 [SMILES: CC1(C)C2CCC1(C)C(OC(=O)/C=C/c1ccc3c(c1)OCO3)C2]

In certain embodiments, the composition is substantially free of bornyl ester of cinnamic acid:

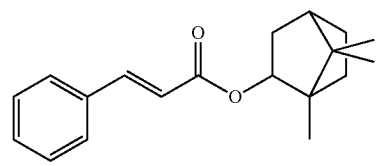

In certain embodiments, the composition is substantially free of flavanone:

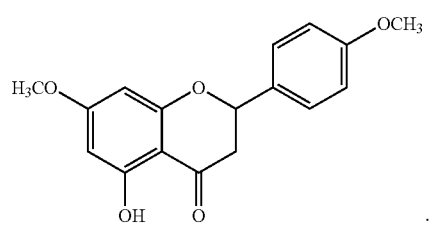 [SMILES: COc1ccc(C2CC(=O)c3c(O)cc(OC)cc3O2)cc1]

In certain embodiments, the composition is substantially free of pinostrobin.

Certain embodiments of the invention provide a composition comprising at least one compound selected from the group consisting of dihydromethysticin, wherein the weight percent of dihydromethysticin in the composition is about 20 to 99%; methysticin, wherein the weight percent of methysticin in the composition is about 10 to 99%; dihydrokavain, wherein the weight percent of dihydrokavain in the composition is about 40 to 99%; kavain, wherein the weight percent of kavain in the composition is about 40 to 99%; desmethoxyyangonin, wherein the weight percent of desmethoxyyangonin in the composition is about 30 to 99%; and 11-methoxyyangonin, wherein the weight percent of 11-methoxyyangonin in the composition is about 20 to 99%.

In certain embodiments, the at least one compound is dihydromethysticin, wherein the weight percent of dihydromethysticin in the composition is about 20 to 99% (e.g., about 25 to 95%, about 30 to 90%, about 35 to 85%, about 40 to 80%, about 45 to 75%, about 50 to 70%, or about 55 to 65%).

In certain embodiments, the at least one compound is kavain, wherein the weight percent of kavain in the composition is about 40 to 99% (e.g., about 45 to 95%, about 50 to 90%, about 55 to 85%, about 60 to 80%, or about 65 to 75%).

In certain embodiments, the at least one compound is methysticin, wherein the weight percent of methysticin in the composition is about 10 to 99% (e.g., about 15 to 95%, about 20 to 90%, about 25 to 85%, about 30 to 80%, about 35 to 75%, about 40 to 70%, about 45 to 65%, or about 50 to 60%).

In certain embodiments, the at least one compound is dihydrokavain, wherein the weight percent of dihydrokavain in the composition is about 40 to 99% (e.g., about 45 to 95%, about 50 to 90%, about 55 to 85%, about 60 to 80%, or about 65 to 75%).

In certain embodiments, the at least one compound is desmethoxyyangonin, wherein the weight percent of desmethoxyyangonin in the composition is 30 to 99% (e.g., about 35 to 95%, about 40 to 90%, about 45 to 85%, about 50 to 80%, about 55 to 75%, or about 60 to 70%).

In certain embodiments, the at least one compound is 11-methoxyyangonin, wherein the weight percent of 11-methoxyyangonin in the composition is 20 to 99% (e.g., about 25 to 95%, about 30 to 90%, about 35 to 85%, about 40 to 80%, about 45 to 75%, about 50 to 70%, or about 55 to 65%).

In certain embodiments, the composition is substantially free of methysticin.

In certain embodiments, the composition further comprises flavanone:

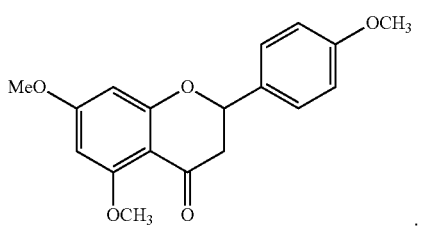 [SMILES: COc1ccc(C2CC(=O)c3c(OC)cc(OC)cc3O2)cc1]

and
wherein the weight percent of the flavanone in the composition is about 20 to 99% (e.g., about 25 to 95%, about 30 to 90%, about 35 to 85%, about 40 to 80%, about 45 to 75%, about 50 to 70%, or about 55 to 65%).

In certain embodiments, the composition is substantially free of flavokawain B.

In certain embodiments, the composition is substantially free of flavokawain A.

In certain embodiments, the composition is substantially free of bornyl ester of 3,4-methylenedioxy cinnamic acid:

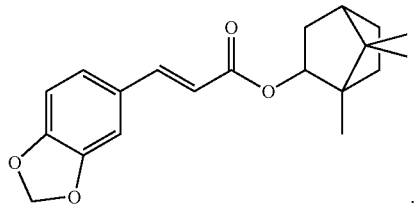 [SMILES: CC1(C)C2CCC1(C)C(OC(=O)/C=C/c1ccc3c(c1)OCO3)C2]

In certain embodiments, the composition is substantially free of bornyl ester of cinnamic acid:

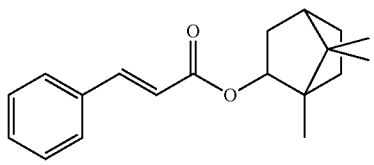

In certain embodiments, the composition is substantially free of flavanone:

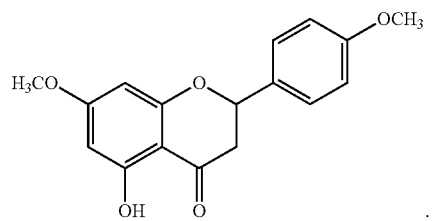 [SMILES: COc1ccc(C2CC(=O)c3c(O)cc(OC)cc3O2)cc1]

In certain embodiments, the composition is substantially free of pinostrobin.

In certain embodiments, the composition is a kava extract.

Certain embodiments of the invention provide a kava extract comprising at least one compound selected from the group consisting of dihydromethysticin, methysticin, dihydrokavain, kavain, desmethoxyyangonin and 11-methoxyyangonin, wherein the extract is substantially free of flavokawain B and/or flavokawain A.

In certain embodiments, the at least one compound is dihydrokavain.

In certain embodiments, the at least one compound is kavain.

In certain embodiments, the at least one compound is methysticin.

In certain embodiments, the at least one compound is dihydromethysticin.

In certain embodiments, the at least one compound is desmethoxyyangonin.

In certain embodiments, the at least one compound is 11-methoxyyangonin.

In certain embodiments of the invention, the kava extract comprises at least two compounds selected from the group consisting of dihydromethysticin, methysticin, dihydrokavain, kavain, desmethoxyyangonin and 11-methoxyyangonin, wherein the extract is substantially free of flavokawain B and/or flavokawain A.

In certain embodiments of the invention, the kava extract comprises at least three compounds selected from the group consisting of dihydromethysticin, methysticin, dihydrokavain, kavain, desmethoxyyangonin and 11-methoxyyangonin, wherein the extract is substantially free of flavokawain B and/or flavokawain A.

In certain embodiments of the invention, the kava extract comprises at least four compounds selected from the group consisting of dihydromethysticin, methysticin, dihydrokavain, kavain, desmethoxyyangonin and 11-methoxyyangonin, wherein the extract is substantially free of flavokawain B and/or flavokawain A.

In certain embodiments of the invention, the kava extract comprises at least five compounds selected from the group consisting of dihydromethysticin, methysticin, dihydrokavain, kavain, desmethoxyyangonin and 11-methoxyyangonin, wherein the extract is substantially free of flavokawain B and/or flavokawain A.

In certain embodiments of the invention, the kava extract comprises dihydromethysticin, methysticin, dihydrokavain, kavain, desmethoxyyangonin and 11-methoxyyangonin, wherein the extract is substantially free of flavokawain B and/or flavokawain A.

In certain embodiments, the kava extract further comprises flavanone:

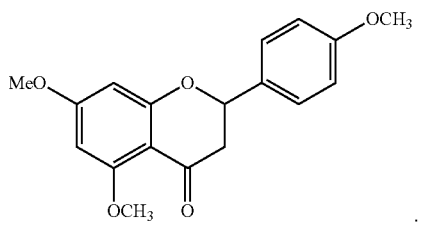 [SMILES: COc1ccc(C2CC(=O)c3c(OC)cc(OC)cc3O2)cc1]

In certain embodiments, the kava extract is substantially free of flavokawain B.

In certain embodiments, the kava extract is substantially free of flavokawain A.

In certain embodiments, the kava extract is substantially free of bornyl ester of 3,4-methylenedioxy cinnamic acid:

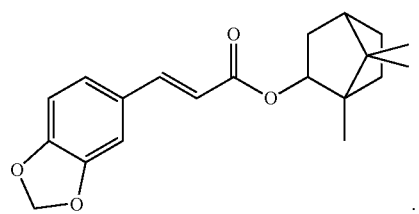 [SMILES: CC1(C)C2CCC1(C)C(OC(=O)/C=C/c1ccc3c(c1)OCO3)C2]

In certain embodiments, the kava extract is substantially free of bornyl ester of cinnamic acid:

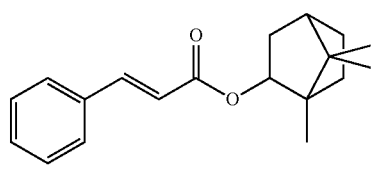

In certain embodiments, the kava extract is substantially free of flavanone:

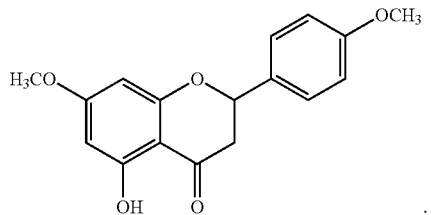 [SMILES: COc1ccc(C2CC(=O)c3c(O)cc(OC)cc3O2)cc1]

In certain embodiments, the kava extract is substantially free of pinostrobin.

Certain embodiments of the invention provide a kava extract comprising 11-methoxyyangonin and/or flavanone:

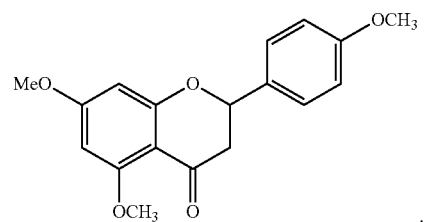 [SMILES: COc1ccc(C2CC(=O)c3c(OC)cc(OC)cc3O2)cc1]

and at least one compound selected from the group consisting of dihydromethysticin, methysticin, dihydrokavain, kavain and desmethoxyyangonin, wherein the extract is substantially free of flavokawain B and/or flavokawain A.

In certain embodiments, the at least one compound is dihydrokavain.

In certain embodiments, the at least one compound is kavain.

In certain embodiments, the at least one compound is methysticin.

In certain embodiments, the at least one compound is dihydromethysticin.

In certain embodiments, the at least one compound is desmethoxyyangonin.

In certain embodiments, the kava extract is substantially free of methysticin.

In certain embodiments, the kava extract is substantially free of flavokawain B.

In certain embodiments, the kava extract is substantially free of flavokawain A.

In certain embodiments, the kava extract is substantially free of bornyl ester of 3,4-methylenedioxy cinnamic acid:

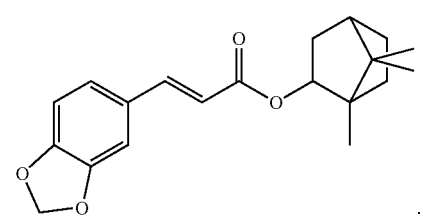 [SMILES: CC1(C)C2CCC1(C)C(OC(=O)/C=C/c1ccc3c(c1)OCO3)C2]

In certain embodiments, the kava extract is substantially free of bornyl ester of cinnamic acid:

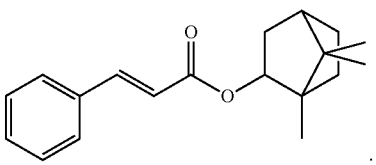 [SMILES: CC1(C)C2CCC1(C)C(OC(=O)/C=C/c1ccccc1)C2]

In certain embodiments, the kava extract is substantially free of flavanone:

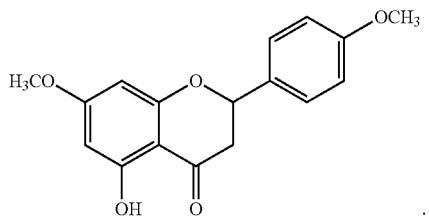

In certain embodiments, the kava extract is substantially free of pinostrobin.

Certain embodiments of the invention provide a kava extract consisting essentially of dihydromethysticin, 11-methoxyyangonin, desmethoxyyangonin, dihydrokavain, kavain, methysticin and flavanone:

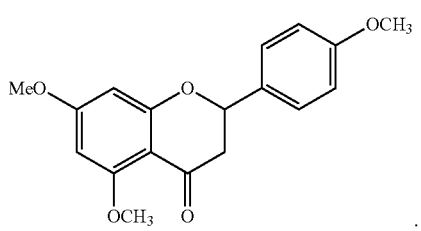 [SMILES: COc1ccc(C2CC(=O)c3c(OC)cc(OC)cc3O2)cc1]

Certain embodiments of the invention provide a kava extract consisting essentially of dihydromethysticin, 11-methoxyyangonin, desmethoxyyangonin, dihydrokavain, kavain and methysticin.

Certain embodiments of the invention provide a kava extract consisting essentially of dihydromethysticin, dihydrokavain, kavain and methysticin.

Certain embodiments of the invention provide a composition or kava extract as described herein, wherein the composition or extract is suitable for ingestion by a mammal (e.g., a human or a dog).

Certain embodiments of the invention provide a composition or kava extract formulated in a tablet, capsule, powder, spray, chewing gum, inhalable, patch, nano-emulsion, cream, gel, stent or liquid.

Certain embodiments of the invention provide a pharmaceutical composition comprising a composition or kava extract as described herein and a pharmaceutically acceptable carrier.

Certain embodiments of the invention provide a method, comprising:
 a) combining an ethanolic kava extract and silica gel to provide a mixture;
 b) evaporating the mixture to provide a silica gel having kava residue adsorbed thereon;
 c) loading the silica gel having kava residue adsorbed thereon on a chromatography column to provide a kava-adsorbed silica gel column;
 d) eluting the kava-adsorbed silica gel column with a solvent system to provide a first kava extract fraction, a second kava extract fraction, and a third kava extract fraction, wherein the first kava extract fraction consists essentially of non-polar compounds, including flavokawains, the second kava extract fraction consists essentially of kavalactones and flavanones, and the third kava extract fraction consists essentially of polar compounds.

In certain embodiments, step d) comprises eluting with 28% ethyl acetate (EA) and 72% hexane (Hex) 5 column volumes (CV), followed by 90% EA and 10% Hex 4.1 CV, and then 35% MeOH and 65% EA 5.5 CV.

In certain embodiments, the weight ratio of kava residue to the total weight of silica gel having kava residue adsorbed thereon is 0.3±0.2.

In certain embodiments, the weight ratio of kava residue to the total weight of silica gel having kava residue adsorbed thereon is 0.3±0.15.

In certain embodiments, the weight ratio of kava residue to the total weight of silica gel having kava residue adsorbed thereon is 0.3±0.1.

Certain embodiments of the invention provide a second kava extract fraction prepared by a method described herein.

Certain embodiments of the invention provide a method for treating or preventing cancer in a mammal (e.g., a human or a dog) in need of such treatment comprising, administering to the mammal a carrier and a compound selected from the group consisting of dihydromethysticin, methysticin, dihydrokavain, kavain, desmethoxyyangonin and 11-methoxyyangonin, wherein the compound is substantially free of other kava extract components.

Certain embodiments of the invention provide a composition comprising a carrier and a compound selected from the group consisting of dihydromethysticin, methysticin, dihydrokavain, kavain, desmethoxyyangonin and 11-methoxyyangonin, for use in medical therapy, wherein the compound is substantially free of other kava extract components.

Certain embodiments of the invention provide a composition comprising a carrier and a compound selected from the group consisting of dihydromethysticin, methysticin, dihydrokavain, kavain, desmethoxyyangonin and 11-methoxyyangonin, for the prophylactic or therapeutic treatment of cancer, wherein the compound is substantially free of other kava extract components.

Certain embodiments of the invention provide the use of a composition comprising a carrier and a compound selected from the group consisting of dihydromethysticin, methysticin, dihydrokavain, kavain, desmethoxyyangonin and 11-methoxyyangonin, to prepare a medicament for preventing or treating cancer in a mammal, wherein the compound is substantially free of other kava extract components.

Certain embodiments of the invention provide a method for treating or preventing cancer in a mammal (e.g., a human or a dog) in need of such treatment comprising, administering to the mammal dihydromethysticin and a carrier, wherein the dihydromethysticin is substantially free of other kava extract components.

Certain embodiments of the invention provide a composition comprising dihydromethysticin and a carrier for the prophylactic or therapeutic treatment of cancer in a mammal, wherein the dihydromethysticin is substantially free of other kava extract components.

Certain embodiments of the invention provide the use of a composition comprising dihydromethysticin and a carrier to prepare a medicament for treating or preventing cancer in a mammal, wherein the dihydromethysticin is substantially free of other kava extract components.

Certain embodiments of the invention provide the use of a composition comprising dihydromethysticin and a carrier for use in medical therapy, wherein the dihydromethysticin is substantially free of other kava extract components.

In certain embodiments, the dihydromethysticin is (+)-dihydromethysticin.

In certain embodiments, the dihydromethysticin is (±)-dihydromethysticin.

In certain embodiments, the dihydromethysticin is enriched in (+)-dihydromethysticin (e.g., at least about 51%, 60%, 70%, 80%, 90%, 95% or 99% (+)-dihydromethysticin).

In certain embodiments, the dihydromethysticin is enriched in (−)-dihydromethysticin (e.g., at least about 51%, 60%, 70%, 80%, 90%, 95% or 99% (−)-dihydromethysticin).

In certain embodiments, the dihydromethysticin is (−)-dihydromethysticin.

In certain embodiments, the other kava extract components are selected from the group consisting of 11-methoxyyangonin, desmethoxyyangonin, dihydrokavain, kavain, methysticin, pinostrobin, flavokawain B, flavokawain A,

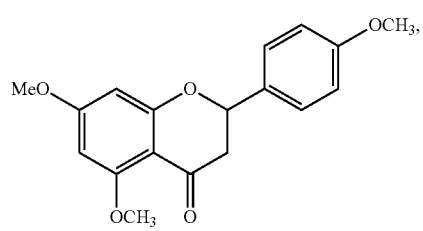
flavanone

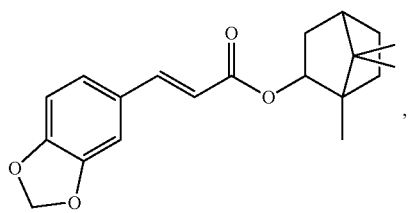
bornyl ester of 3,4-methylenedioxy cinnamic acid

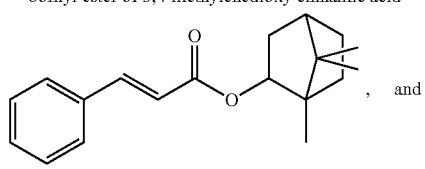, and
bornyl ester of cinnamic acid

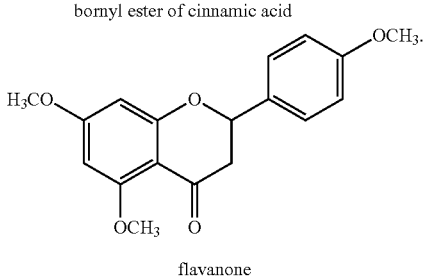
flavanone

Certain embodiments of the invention provide a method for treating or preventing cancer in a mammal in need of such treatment comprising, administering to the mammal methysticin and a carrier, wherein the methysticin is substantially free of other kava extract components.

Certain embodiments of the invention provide a composition comprising methysticin and a carrier for the prophylactic or therapeutic treatment of cancer in a mammal, wherein the methysticin is substantially free of other kava extract components.

Certain embodiments of the invention provide the use of a composition comprising methysticin and a carrier to prepare a medicament for treating or preventing cancer in a mammal, wherein the methysticin is substantially free of other kava extract components.

Certain embodiments of the invention provide the use of a composition comprising methysticin and a carrier for use in medical therapy, wherein the methysticin is substantially free of other kava extract components.

In certain embodiments, the other kava extract components are selected from the group consisting of 11-methoxyyangonin, desmethoxyyangonin, dihydrokavain, kavain, dihydromethysticin, pinostrobin, flavokawain B, flavokawain A,

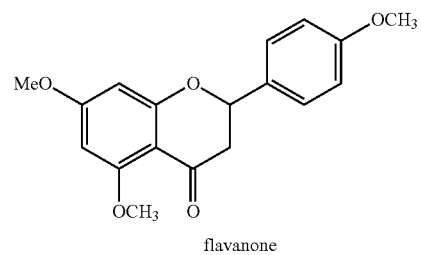
flavanone

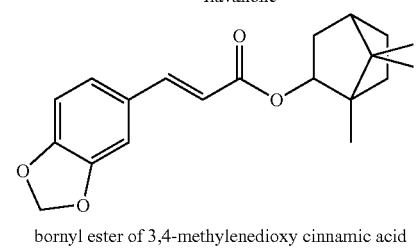,
bornyl ester of 3,4-methylenedioxy cinnamic acid

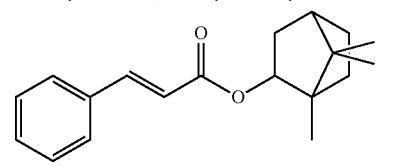
bornyl ester of cinnamic acid , and

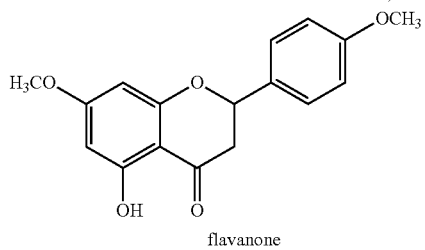
flavanone

Certain embodiments of the invention provide a method for treating or preventing cancer in a mammal in need of such treatment comprising, administering to the mammal dihydrokavain and a carrier, wherein the dihydrokavain is substantially free of other kava extract components.

Certain embodiments of the invention provide a composition comprising dihydrokavain and a carrier for the prophylactic or therapeutic treatment of cancer in a mammal, wherein the dihydrokavain is substantially free of other kava extract components.

Certain embodiments of the invention provide the use of a composition comprising dihydrokavain and a carrier to prepare a medicament for treating or preventing cancer in a mammal, wherein the dihydrokavain is substantially free of other kava extract components.

Certain embodiments of the invention provide the use of a composition comprising dihydrokavain and a carrier for use in medical therapy, wherein the dihydrokavain is substantially free of other kava extract components.

In certain embodiments, the other kava extract components are selected from the group consisting of 11-methoxyyangonin, desmethoxyyangonin, dihydromethysticin, kavain, methysticin, pinostrobin, flavokawain B, flavokawain A,

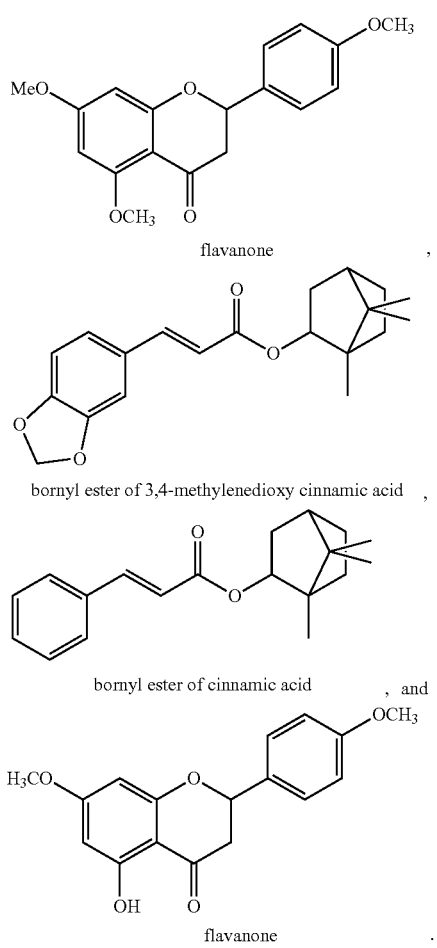 [SMILES: COc1ccc(C2CC(=O)c3c(OC)cc(OC)cc3O2)cc1 ; CC1(C)C2CCC1(C)C(OC(=O)/C=C/c1ccc3c(c1)OCO3)C2 ; CC1(C)C2CCC1(C)C(OC(=O)/C=C/c1ccccc1)C2 ; COc1ccc(C2CC(=O)c3c(O)cc(OC)cc3O2)cc1]

flavanone, bornyl ester of 3,4-methylenedioxy cinnamic acid, bornyl ester of cinnamic acid, and flavanone.

Certain embodiments of the invention provide a method for treating or preventing cancer in a mammal in need of such treatment comprising, administering to the mammal kavain and a carrier, wherein the kavain is substantially free of other kava extract components.

Certain embodiments of the invention provide a composition comprising kavain and a carrier for the prophylactic or therapeutic treatment of cancer in a mammal, wherein the kavain is substantially free of other kava extract components.

Certain embodiments of the invention provide the use of a composition comprising kavain and a carrier to prepare a medicament for treating or preventing cancer in a mammal, wherein the kavain is substantially free of other kava extract components.

Certain embodiments of the invention provide the use of a composition comprising kavain and a carrier for use in medical therapy, wherein the kavain is substantially free of other kava extract components.

In certain embodiments, the other kava extract components are selected from the group consisting of 11-methoxyyangonin, desmethoxyyangonin, dihydrokavain, dihydromethysticin, methysticin, pinostrobin, flavokawain B, flavokawain A,

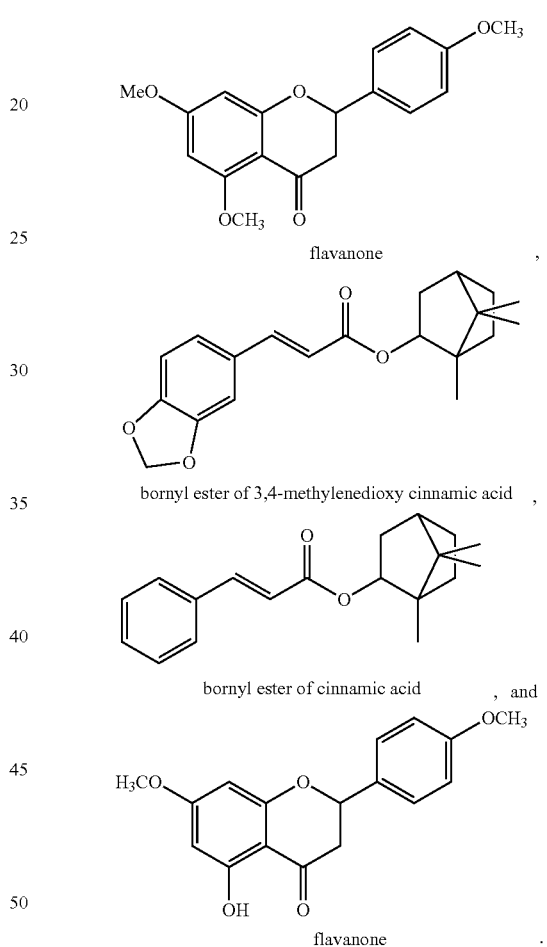

flavanone, bornyl ester of 3,4-methylenedioxy cinnamic acid, bornyl ester of cinnamic acid, and flavanone.

Certain embodiments of the invention provide a method for treating or preventing cancer in a mammal in need of such treatment comprising, administering to the mammal desmethoxyyangonin and a carrier, wherein the desmethoxyyangonin is substantially free of other kava extract components.

Certain embodiments of the invention provide a composition comprising desmethoxyyangonin and a carrier for the prophylactic or therapeutic treatment of cancer in a mammal, wherein the desmethoxyyangonin is substantially free of other kava extract components.

Certain embodiments of the invention provide the use of a composition comprising desmethoxyyangonin and a carrier to prepare a medicament for treating or preventing cancer in a mammal, wherein the desmethoxyyangonin is substantially free of other kava extract components.

Certain embodiments of the invention provide the use of a composition comprising desmethoxyyangonin and a carrier for use in medical therapy, wherein the desmethoxyyangonin is substantially free of other kava extract components.

In certain embodiments, the other kava extract components are selected from the group consisting of 11-methoxyyangonin, dihydromethysticin, dihydrokavain, kavain, methysticin, pinostrobin, flavokawain B, flavokawain A,

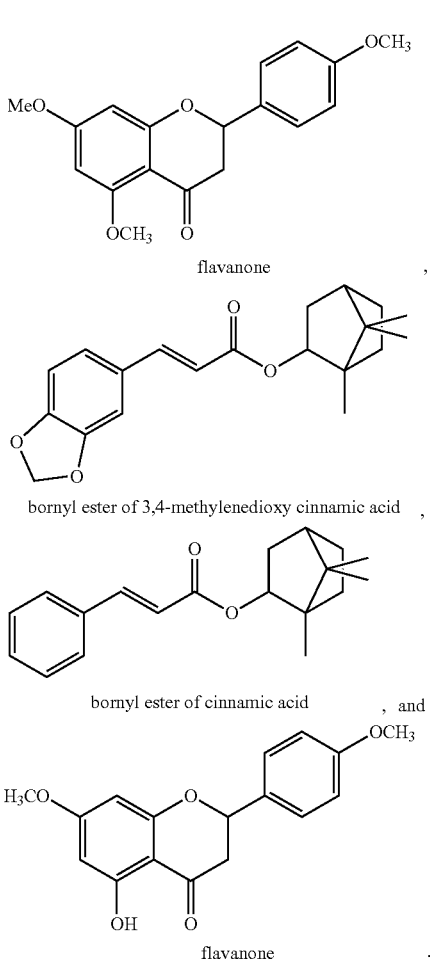

Certain embodiments of the invention provide a method for treating or preventing cancer in a mammal in need of such treatment comprising, administering to the mammal 11-methoxyyangonin and a carrier, wherein the 11-methoxyyangonin is substantially free of other kava extract components.

Certain embodiments of the invention provide a composition comprising 11-methoxyyangonin and a carrier for the prophylactic or therapeutic treatment of cancer in a mammal, wherein the 11-methoxyyangonin is substantially free of other kava extract components.

Certain embodiments of the invention provide the use of a composition comprising 11-methoxyyangonin and a carrier to prepare a medicament for treating or preventing cancer in a mammal, wherein the 11-methoxyyangonin is substantially free of other kava extract components.

Certain embodiments of the invention provide the use of a composition comprising 11-methoxyyangonin and a carrier for use in medical therapy, wherein the 11-methoxyyangonin is substantially free of other kava extract components.

In certain embodiments, the other kava extract components are selected from the group consisting of desmethoxyyangonin, dihydromethysticin, dihydrokavain, kavain, methysticin, pinostrobin, flavokawain B, flavokawain A,

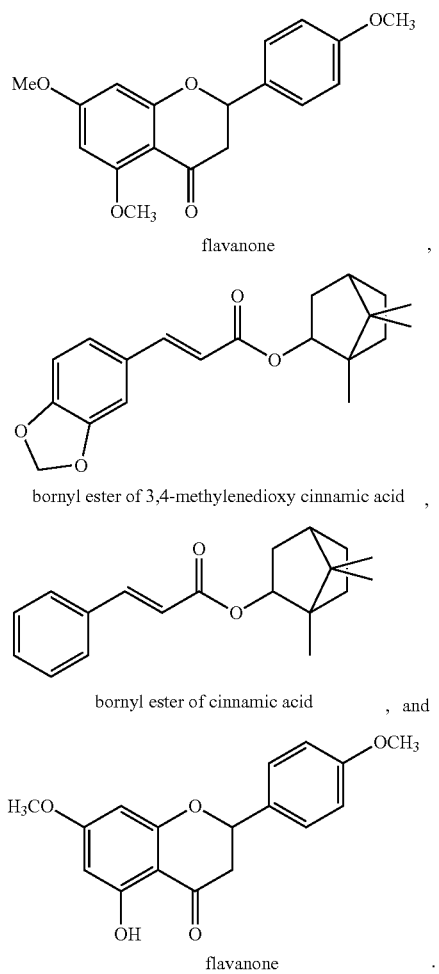 [SMILES: COc1ccc(C2CC(=O)c3c(OC)cc(OC)cc3O2)cc1 ; CC1(C)C2CCC1(C)C(OC(=O)/C=C/c1ccc3c(c1)OCO3)C2 ; CC1(C)C2CCC1(C)C(OC(=O)/C=C/c1ccccc1)C2 ; COc1ccc(C2CC(=O)c3c(O)cc(OC)cc3O2)cc1]

In certain embodiments, the other kava extract components are selected from the group consisting of pinostrobin, flavokawain B, flavokawain A,

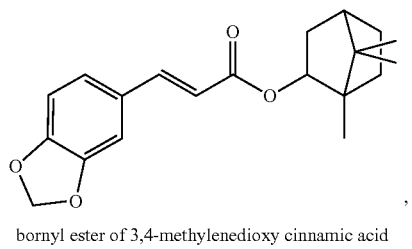

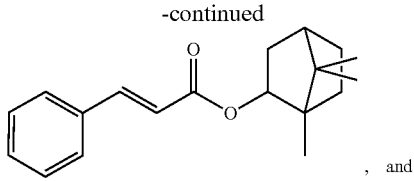

bornyl ester of cinnamic acid

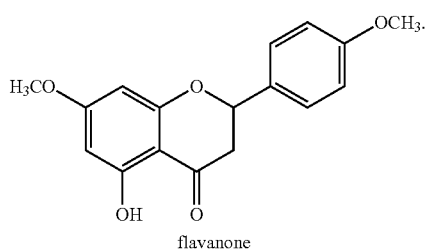

flavanone

Certain embodiments of the invention provide a method for treating or preventing cancer in a mammal in need of such treatment comprising, administering to the mammal a composition or kava extract as described herein.

Certain embodiments of the invention provide, a composition or kava extract as described herein for the prophylactic or therapeutic treatment of cancer in a mammal.

Certain embodiments of the invention provide the use of a composition or kava extract as described herein to prepare a medicament for treating or preventing cancer in a mammal.

Certain embodiments of the invention provide a composition or kava extract as described herein for use in medical therapy.

In certain embodiments, the cancer is lung cancer, prostate cancer, skin cancer, melanoma, genitourinary cancer, colon and rectum cancer, breast cancer, ovarian cancer, esophageal cancer, pancreatic cancer, urinary bladder cancer, cervical cancer, liver cancer, kidney and renal cancer, head and neck cancer, brain cancer or various hematological cancers.

Certain embodiments of the invention provide a method for preventing tumorigenesis, reducing DNA damage, reducing protein damage and/or detoxifying physical or chemical carcinogens in a mammal in need of such treatment comprising, administering to the mammal a carrier and a compound selected from the group consisting of dihydromethysticin, methysticin, dihydrokavain, kavain, desmethoxyyangonin and 11-methoxyyangonin, wherein the compound is substantially free of other kava extract components.

Certain embodiments of the invention provide a method for preventing tumorigenesis, reducing DNA damage, reducing protein damage and/or detoxifying physical or chemical carcinogens in a mammal in need of such treatment comprising, administering to the mammal a composition or kava extract as described herein.

Certain embodiments of the invention provide a method for preventing tumorigenesis, reducing DNA damage, reducing protein damage, and/or detoxifying physical or chemical carcinogens in a mammal (e.g., a human) in need of such treatment comprising, administering to the mammal dihydromethysticin and a carrier, wherein the dihydromethysticin is substantially free of other kava extract components.

Certain embodiments of the invention provide a composition comprising dihydromethysticin and a carrier for preventing tumorigenesis, reducing DNA damage, reducing protein damage, and/or detoxifying physical or chemical carcinogens in a mammal, wherein the dihydromethysticin is substantially free of other kava extract components.

Certain embodiments of the invention provide the use of a composition comprising dihydromethysticin and a carrier to prepare a medicament for preventing tumorigenesis, reducing DNA damage, reducing protein damage, and/or detoxifying physical or chemical carcinogens in a mammal, wherein the dihydromethysticin is substantially free of other kava extract components.

In certain embodiments, the dihydromethysticin is (+)-dihydromethysticin.

In certain embodiments, the dihydromethysticin is (±)-dihydromethysticin.

In certain embodiments, the dihydromethysticin is enriched in (+)-dihydromethysticin (e.g., at least about 51%, 60%, 70%, 80%, 90%, 95% or 99% (+)-dihydromethysticin).

In certain embodiments, the dihydromethysticin is enriched in (−)-dihydromethysticin (e.g., at least about 51%, 60%, 70%, 80%, 90%, 95% or 99% (−)-dihydromethysticin).

In certain embodiments, the dihydromethysticin is (−)-dihydromethysticin.

In certain embodiments, the other kava extract components are selected from the group consisting of 11-methoxyyangonin, desmethoxyyangonin, dihydrokavain, kavain, methysticin, pinostrobin, flavokawain B, flavokawain A,

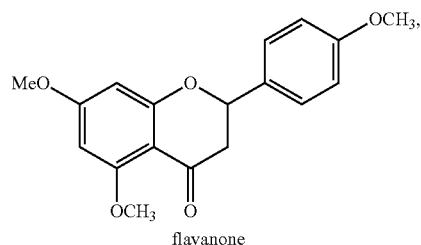

flavanone

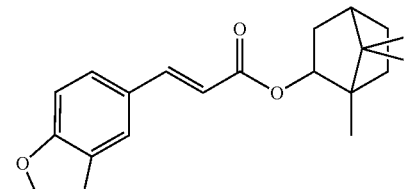

bornyl ester of 3,4-methylenedioxy cinnamic acid

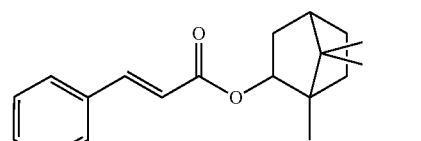

, and bornyl ester of cinnamic acid

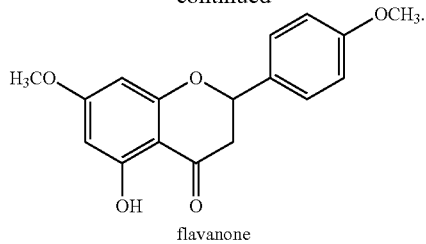

flavanone

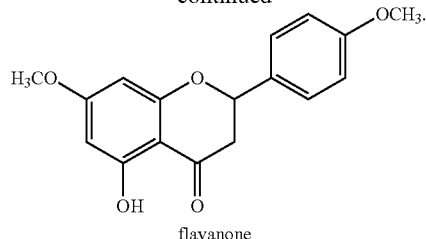

flavanone

Certain embodiments of the invention provide a method for preventing tumorigenesis, reducing DNA damage, reducing protein damage, and/or detoxifying physical or chemical carcinogens in a mammal in need of such treatment comprising, administering to the mammal methysticin and a carrier, wherein the methysticin is substantially free of other kava extract components.

Certain embodiments of the invention provide a composition comprising methysticin and a carrier for preventing tumorigenesis, reducing DNA damage, reducing protein damage, and/or detoxifying physical or chemical carcinogens in a mammal, wherein the methysticin is substantially free of other kava extract components.

Certain embodiments of the invention provide the use of a composition comprising methysticin and a carrier to prepare a medicament for preventing tumorigenesis, reducing DNA damage, reducing protein damage, and/or detoxifying physical or chemical carcinogens in a mammal, wherein the methysticin is substantially free of other kava extract components.

In certain embodiments, the other kava extract components are selected from the group consisting of 11-methoxyyangonin, desmethoxyyangonin, dihydrokavain, kavain, dihydromethysticin, pinostrobin, flavokawain B, flavokawain A, Certain embodiments of the invention provide a method for preventing tumorigenesis, reducing DNA damage, reducing protein damage, and/or detoxifying physical or chemical carcinogens in a mammal in need of such treatment comprising, administering to the mammal dihydrokavain and a carrier, wherein the dihydrokavain is substantially free of other kava extract components.

Certain embodiments of the invention provide a composition comprising dihydrokavain and a carrier for preventing tumorigenesis, reducing DNA damage, reducing protein damage, and/or detoxifying physical or chemical carcinogens in a mammal, wherein the dihydrokavain is substantially free of other kava extract components.

Certain embodiments of the invention provide the use of a composition comprising dihydrokavain and a carrier to prepare a medicament for preventing tumorigenesis, reducing DNA damage, reducing protein damage, and/or detoxifying physical or chemical carcinogens in a mammal, wherein the dihydrokavain is substantially free of other kava extract components.

In certain embodiments, the other kava extract components are selected from the group consisting of 11-methoxyyangonin, desmethoxyyangonin, dihydromethysticin, kavain, methysticin, pinostrobin, flavokawain B, flavokawain A,

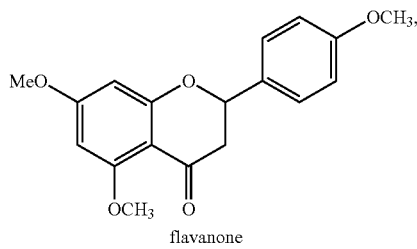

flavanone

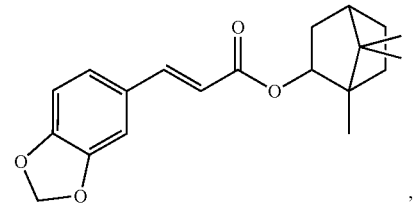

bornyl ester of 3,4-methylenedioxy cinnamic acid

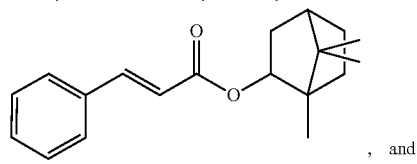

, and bornyl ester of cinnamic acid

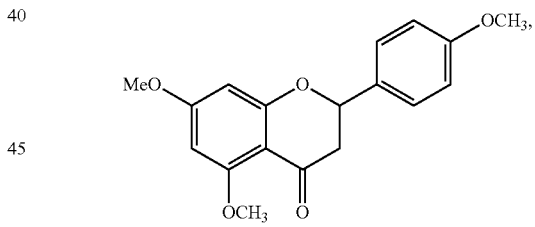

flavanone

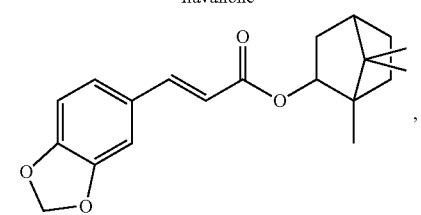

bornyl ester of 3,4-methylenedioxy cinnamic acid

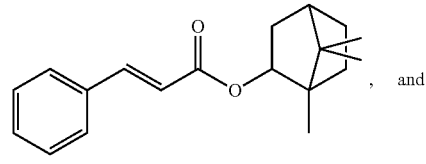

, and bornyl ester of cinnamic acid

-continued

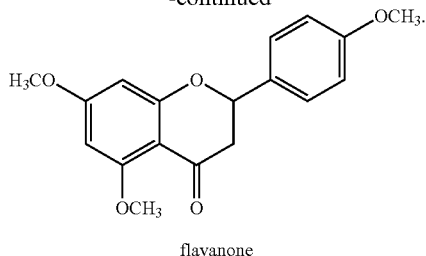

flavanone

Certain embodiments of the invention provide a method for preventing tumorigenesis, reducing DNA damage, reducing protein damage and/or detoxifying physical or chemical carcinogens in a mammal in need of such treatment comprising, administering to the mammal kavain and a carrier, wherein the kavain is substantially free of other kava extract components.

Certain embodiments of the invention provide a composition comprising kavain and a carrier for preventing tumorigenesis, reducing DNA damage, reducing protein damage and/or detoxifying physical or chemical carcinogens in a mammal, wherein the kavain is substantially free of other kava extract components.

Certain embodiments of the invention provide the use of a composition comprising kavain and a carrier to prepare a medicament for preventing tumorigenesis, reducing DNA damage, reducing protein damage, and/or detoxifying physical or chemical carcinogens in a mammal, wherein the kavain is substantially free of other kava extract components.

In certain embodiments, the other kava extract components are selected from the group consisting of 11-methoxyyangonin, desmethoxyyangonin, dihydrokavain, dihydromethysticin, methysticin, pinostrobin, flavokawain B, flavokawain A,

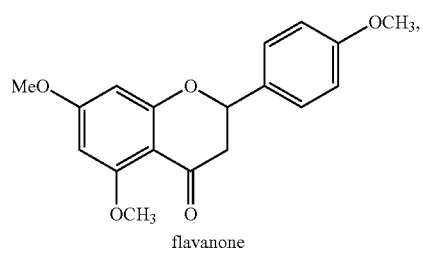

flavanone

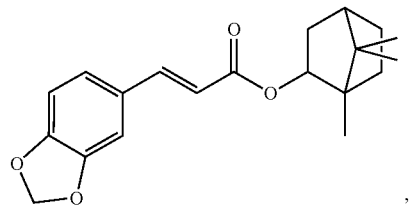

bornyl ester of 3,4-methylenedioxy cinnamic acid

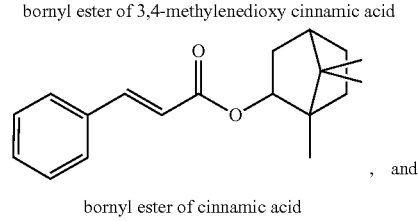

, and bornyl ester of cinnamic acid

-continued

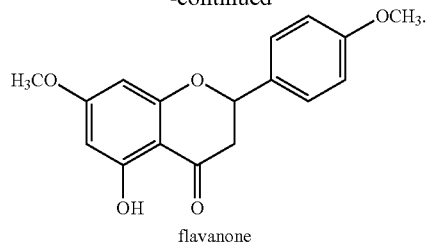

flavanone

Certain embodiments of the invention provide a method for preventing tumorigenesis, reducing DNA damage, reducing protein damage and/or detoxifying physical or chemical carcinogens in a mammal in need of such treatment comprising, administering to the mammal desmethoxyyangonin and a carrier, wherein the desmethoxyyangonin is substantially free of other kava extract components.

Certain embodiments of the invention provide a composition comprising desmethoxyyangonin and a carrier for preventing tumorigenesis, reducing DNA damage, reducing protein damage and/or detoxifying physical or chemical carcinogens in a mammal, wherein the desmethoxyyangonin is substantially free of other kava extract components.

Certain embodiments of the invention provide the use of a composition comprising desmethoxyyangonin and a carrier to prepare a medicament for preventing tumorigenesis, reducing DNA damage, reducing protein damage and/or detoxifying physical or chemical carcinogens in a mammal, wherein the desmethoxyyangonin is substantially free of other kava extract components.

In certain embodiments, the other kava extract components are selected from the group consisting of 11-methoxyyangonin, kavain, dihydrokavain, dihydromethysticin, methysticin, pinostrobin, flavokawain B, flavokawain A,

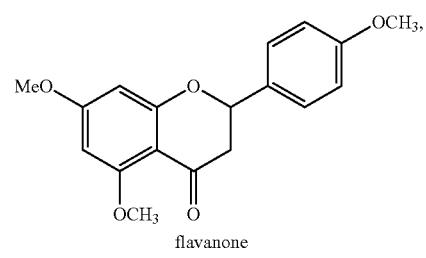

flavanone

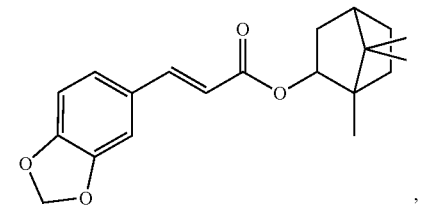

bornyl ester of 3,4-methylenedioxy cinnamic acid

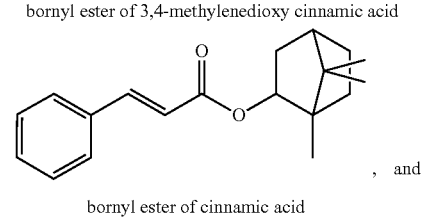

, and bornyl ester of cinnamic acid

31
-continued

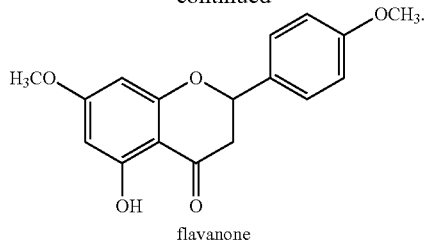
flavanone

Certain embodiments of the invention provide a method for preventing tumorigenesis, reducing DNA damage, reducing protein damage and/or detoxifying physical or chemical carcinogens in a mammal in need of such treatment comprising, administering to the mammal 11-methoxyyangonin and a carrier, wherein the 11-methoxyyangonin is substantially free of other kava extract components.

Certain embodiments of the invention provide a composition comprising 11-methoxyyangonin and a carrier for preventing tumorigenesis, reducing DNA damage, reducing protein damage and/or detoxifying physical or chemical carcinogens in a mammal, wherein the 11-methoxyyangonin is substantially free of other kava extract components.

Certain embodiments of the invention provide the use of a composition comprising 11-methoxyyangonin and a carrier to prepare a medicament for preventing tumorigenesis, reducing DNA damage, reducing protein damage and/or detoxifying physical or chemical carcinogens in a mammal, wherein the 11-methoxyyangonin is substantially free of other kava extract components.

In certain embodiments, the other kava extract components are selected from the group consisting of desmethoxyyangonin, kavain, dihydrokavain, dihydromethysticin, methysticin, pinostrobin, flavokawain B, flavokawain A,

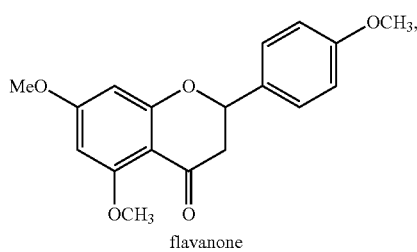
flavanone

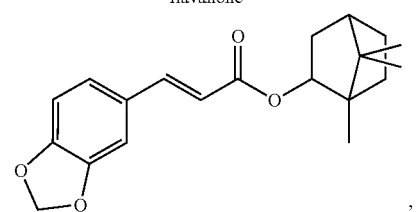
bornyl ester of 3,4-methylenedioxy cinnamic acid

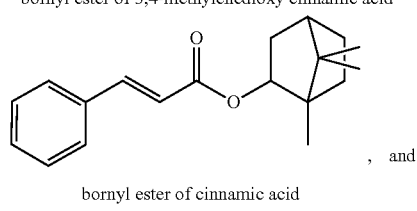
, and bornyl ester of cinnamic acid

32
-continued

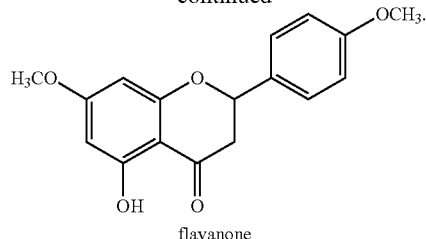
flavanone

In certain embodiments, the other kava extract components are selected from the group consisting of pinostrobin, flavokawain B, flavokawain A,

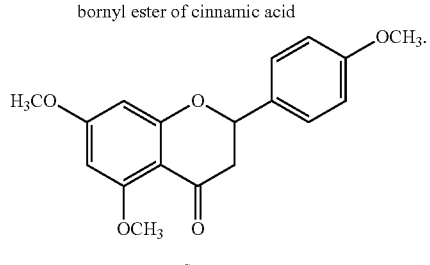

bornyl ester of 3,4-methylenedioxy cinnamic acid bornyl ester of cinnamic acid flavanone Certain embodiments of the invention provide a method for preventing tumorigenesis, reducing DNA damage, reducing protein damage and/or detoxifying physical or chemical carcinogens in a mammal in need of such treatment comprising, administering to the mammal a composition or kava extract as described herein.

Certain embodiments of the invention provide a composition or kava extract as described herein for preventing tumorigenesis, reducing DNA damage, reducing protein damage and/or detoxifying physical or chemical carcinogens in a mammal.

Certain embodiments of the invention provide the use of a composition or kava extract as described herein to prepare a medicament for preventing tumorigenesis, reducing DNA damage, reducing protein damage and/or detoxifying physical or chemical carcinogens in a mammal.

In certain embodiments, the DNA damage is reduced by about 1%, 5%, 10%, 15%, 20%, 25%, 30%, 35%, 40%, 45%, 50%, 55%, 60%, 65%, 70%, 75%, 80%, 85%, 90%, 95%, or 100%, as compared to a mammal not administered a composition or kava extract as described herein.

In certain embodiments, the protein damage is reduced by about 1%, 5%, 10%, 15%, 20%, 25%, 30%, 35%, 40%, 45%, 50%, 55%, 60%, 65%, 70%, 75%, 80%, 85%, 90%, 95%, or 100%, as compared to a mammal not administered a composition or kava extract as described herein.

In certain embodiments, the DNA damage is a DNA adduct, caused by physical or chemical carcinogens.

In certain embodiments, the DNA adduct is a $O^6$-methylguanine DNA adduct.

In certain embodiments, the DNA adduct is a 7-methylguanine DNA adduct.

In certain embodiments, the DNA adducts are BaP, PhIP, POB and/or PHB adducts.

In certain embodiments, the DNA adducts are POB and PHB DNA adducts (e.g., 7-pobG, 7-[4-(3-pyridyl)-4-oxobut-1-yl]guanine; $O^2$-pobdT, $O^2$-[4-(3-pyridyl)-4-oxobut-lyl]thymidine; $O^6$-pobdG, $O^6$-[4-(3-pyridyl)-4-oxobut-1-yl]-2'-deoxyguanosine; $O^2$-pobC, $O^2$-[4-(3-pyridyl)-4-oxobut-1-yl]cytidine).

Certain embodiments of the invention provide a composition comprising a carrier and a compound selected from the group consisting of dihydromethysticin, methysticin, dihydrokavain, kavain, desmethoxyyangonin and 11-methoxyyangonin for use in medical therapy, wherein the compound is substantially free of other kava extract components.

Certain embodiments of the invention provide a composition comprising a carrier and a compound selected from the group consisting of dihydromethysticin, methysticin, dihydrokavain, kavain, desmethoxyyangonin and 11-methoxyyangonin for the prophylactic or therapeutic treatment of cancer, wherein the compound is substantially free of other kava extract components.

Certain embodiments of the invention provide a composition comprising a carrier and a compound selected from the group consisting of dihydromethysticin, methysticin, dihydrokavain, kavain, desmethoxyyangonin and 11-methoxyyangonin to prepare a medicament for preventing or treating cancer in a mammal, wherein the compound is substantially free of other kava extract components.

In certain embodiments, the compound is dihydromethysticin.

In certain embodiments, the compound is methysticin.

In certain embodiments, the compound is dihydrokavain.

In certain embodiments, the compound is kavain.

In certain embodiments, the compound is desmethoxyyangonin.

In certain embodiments, the compound is 11-methoxyyangonin.

The invention also provides processes and intermediates disclosed herein that are useful for preparing compositions and extracts described herein (see, e.g., the Examples).

As used herein, the phrase "substantially free of" means the composition or kava extract comprises less than about 5%, 4%, 3%, 2%, 1%, 0.9%, 0.8%, 0.7%, 0.6%, 0.5%, 0.4%, 0.3%, 0.2%, 0.1% or 0.05% by weight of the designated compound(s) and/or components.

As used herein, the phrase "consisting essentially of" means the composition or kava extract comprises less than about 5%, 4%, 3%, 2%, 1%, 0.9%, 0.8%, 0.7%, 0.6%, 0.5%, 0.4%, 0.3%, 0.2%, 0.1% or 0.05% by weight of other compounds and/or components.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. As described in the Examples, the compositions, kava extracts and compounds (e.g., such as, dihydromethysticin, methysticin, dihydrokavain, kavain, desmethoxyyangonin and 11-methoxyyangonin) described herein, have chemopreventive properties, and therefore, are useful for both the treatment and prevention of cancer.

The terms "cancer" and "cancerous" refer to or describe the physiological condition in mammals that is typically characterized by unregulated cell accumulation. A "tumor" comprises one or more cancerous cells. Examples of cancer include, but are not limited to, carcinoma, lymphoma, blastoma, sarcoma, and leukemia or lymphoid malignancies. Specific examples of cancers include, but are not limited to, lung cancer, prostate cancer, skin cancer, melanoma, genitourinary cancer, colon and rectum cancer, breast cancer, ovary cancer, esophageal cancer, pancreatic cancer, urinary bladder cancer, cervical cancer, liver cancer, kidney and renal cancer, head and neck cancer, brain cancer or various hematological cancers. Examples of cancer also include, but are not limited to, cancerous lesions in the above tissues, such as familial adenomatous polyposis, hyperplasia, dysplasia, aberrant crypt foci, adenoma, and others.

The phrase "detoxifying physical or chemical carcinogens" refers to enhancing elimination/deactivation of toxic species generated from physical or chemical carcinogens, reducing the generation of toxic species from physical or chemical carcinogens, and/or activating the immune system to improve self-defense against physical or chemical carcinogens.

As used herein, the terms "protein damage" refers to natural proteins, such as hemoglobin, being modified by the reactive metabolites/species generated by the chemical or physical carcinogens (Murphy et al., Chemico-Biological Interactions 1997; 103:153-166). Methods for measuring protein damage are known in the art, for example, as described in Murphy et al., Chemico-Biological Interactions 1997; 103:153-166.

As used herein, the term "mammal" includes, but is not limited to, humans, mice, rats, guinea pigs, monkeys, dogs, cats, horses, cows, pigs, and sheep, and poultry.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

When a bond in a compound formula herein is drawn in a non-stereochemical manner (e.g. flat), the atom to which the bond is attached includes all stereochemical possibilities.

For example, in certain embodiments, all stereochemical possibilities are included for the following compounds:

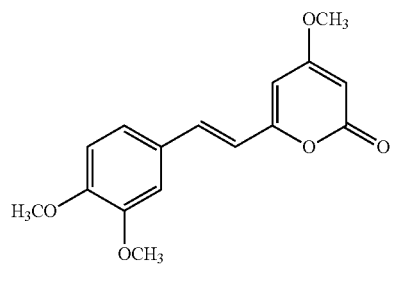

11-Methoxyyangonin

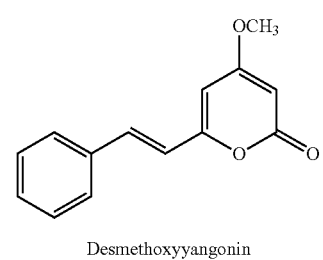

Desmethoxyyangonin

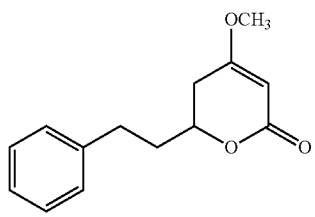

Dihydrokavain

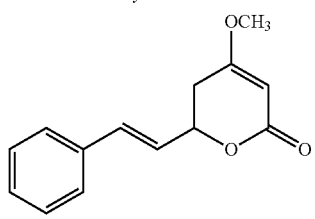

Kavain

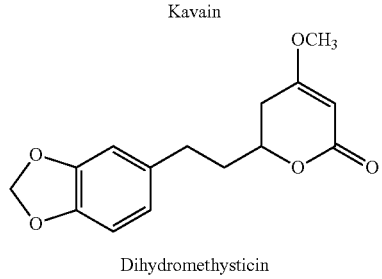

Dihydromethysticin

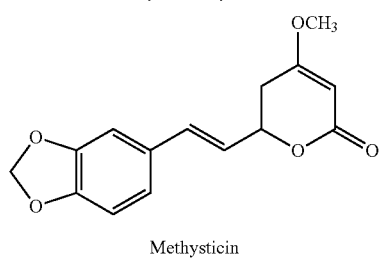

Methysticin

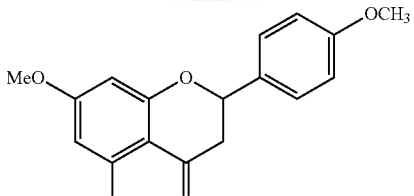

flavanone

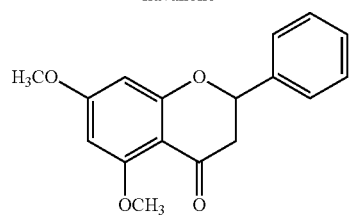

Pinostrobin

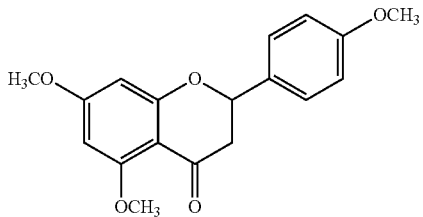

flavanone

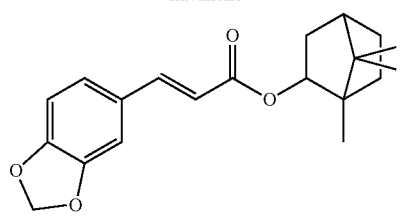

Bornyl esters of 3,4-methylenedioxy cinnamic acid

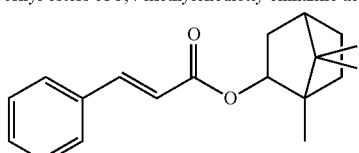

Bornyl esters of cinnamic acid

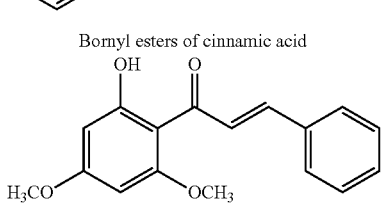

Flavokawain B

When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted. For example, in certain embodiments, the atom to which the stereochemical bond is attached is enriched in the absolute stereoisomer depicted for the following compounds:

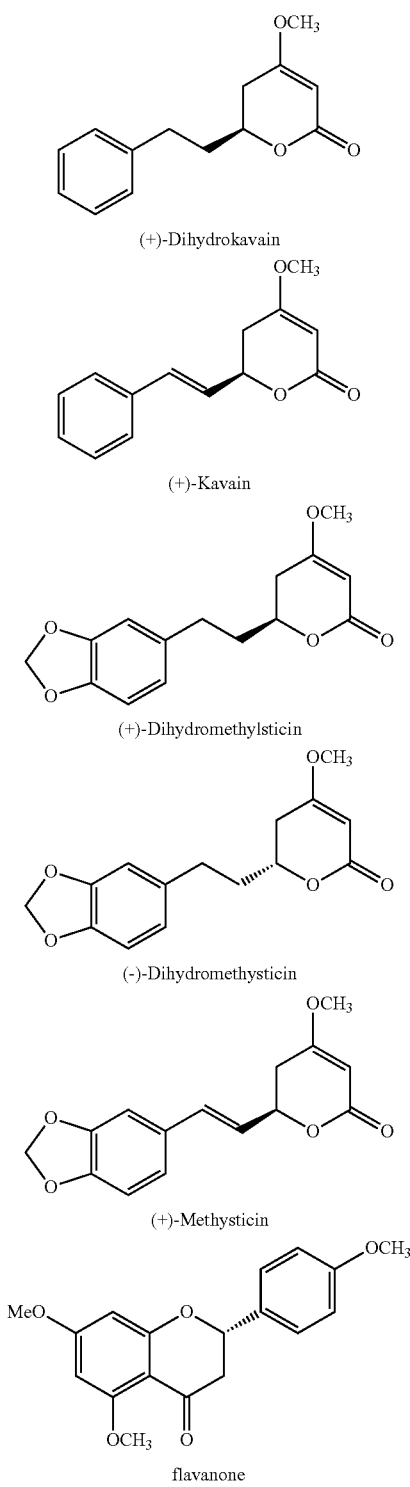

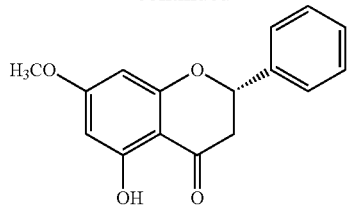

Pinostrobin

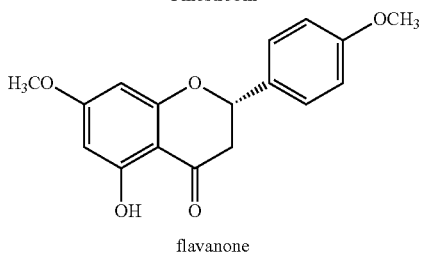

flavanone

In certain embodiments, the invention provides a composition enriched in non-natural (−)-dihydromethysticin:

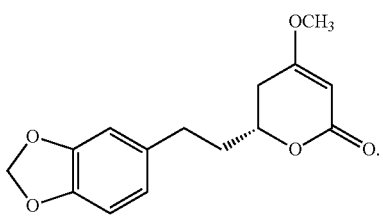 [SMILES: COC1=CC(=O)O[C@H](CCc2ccc3c(c2)OCO3)C1]

The compositions, kava extracts and compounds described herein (e.g., such as, dihydromethysticin, methysticin, dihydrokavain, kavain, desmethoxyyangonin and 11-methoxyyangonin) can be formulated as compositions (e.g., pharmaceutical) and administered to a mammalian host, such as a human patient in a variety of forms adapted to the chosen route of administration, i.e., orally or parenterally, by intravenous, intramuscular, topical or subcutaneous routes.

Thus, the present compositions, kava extracts and compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food and drinks of the patient's diet. For oral therapeutic administration, the present compositions, kava extracts and compounds may be combined with one or more excipients and used in the form of ingestible tablets, buccal tablets, troches, capsules, elixirs, suspensions, syrups, spray, nano-emulsion, patch, cream, gum, gel, stent, wafers, drinks and the like. Such compositions and preparations should contain at least 0.01% of the present compositions, kava extracts and compounds. The percentage of the compositions and preparations may, of course, be varied and may conveniently be between about 0.1 to about 60% of the weight of a given unit dosage form. The amount of the present compositions, kava extracts and compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the present compositions, kava extracts or compounds, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the present compositions, kava extracts and compounds may be incorporated into sustained-release preparations and devices.

The present compositions, kava extracts and compounds may also be administered intravenously or intraperitoneally by infusion or injection. Solutions of the present compositions, kava extracts and compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the present compositions, kava extracts and compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the present compositions, kava extracts or compounds in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the present compositions, kava extracts and compounds plus any additional desired ingredient present in the previously sterile-filtered solutions.

For topical administration, the present compositions, kava extracts and compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compositions, kava extracts and compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present compositions, kava extracts and compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the present compositions, kava extracts and compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the present compositions, kava extracts or compounds, required for use in the treatment or prevention of cancer, prevention of tumorigenesis, reduction of DNA and protein damage and/or detoxification of physical or chemical carcinogens will vary not only with the particular form selected but also with the route of administration, the nature of the condition being treated and the age and condition of the patient and will be ultimately at the discretion of the attendant physician or clinician.

In general, however, a suitable dose will be in the range of from about 0.05 to about 100 mg/kg, e.g., from about 1 to about 75 mg/kg of body weight per day, such as 3 to about 50 mg per kilogram body weight of the recipient per day, preferably in the range of 0.2 to 90 mg/kg/day, most preferably in the range of 1 to 15 mg/kg/day. For example, in certain embodiments, dihydromethysticin may be administered in the range of about 0.2 to 1.0 mg/kg/day, or from about 0.4 to about 0.8 mg/kg/day, or about 0.6 mg/kg/day.

The present compositions, kava extracts and compounds are conveniently formulated in unit dosage form; for example, containing 5 to 1000 mg, conveniently 10 to 750 mg, most conveniently, 50 to 500 mg of the present compositions, kava extracts or compounds per unit dosage form. In one embodiment, the invention provides a composition comprising a present composition, kava extract or compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention will now be illustrated by the following non-limiting Examples.

Example 1

As described herein, the tumorigenesis-stage specificity of kava, the potential active compounds, and the underlying mechanisms in NNK-induced lung tumorigenesis in A/J mice has now been investigated. In the first experiment, NNK-treated mice were given diets containing kava at a dose of 5 mg/g of diet during different periods. Kava treatments covering the initiation stage reduced the multiplicity of lung adenomas by ~99%. A minimum effective dose is yet to be defined because kava at two lower dosages (2.5 and 1.25 mg/g of diet) were equally effective as 5 mg/g of diet in complete inhibiting lung adenoma formation. Daily gavage of kava (one before, during, and after NNK treatment) completely blocked lung adenoma formation as well. Kavalactone-enriched Fraction B fully recapitulated kava's chemopreventive efficacy while kavalactone-free Fractions A and C were much less effective. Mechanistically, kava and Fraction B reduced NNK-induced DNA damage in lung tissues with a unique and preferential reduction in $O^6$-methylguanine ($O^6$-mG), the highly tumorigenic DNA damage by NNK, correlating and predictive of efficacy on blocking lung adenoma formation. Taken together, these results demonstrate the outstanding efficacy of kava in preventing NNK-induced lung tumorigenesis in A/J mice with high selectivity for the initiation stage in association with the reduction of $O^6$-mG adduct in DNA. They also establish the knowledge basis for the identification of the active compound(s) in kava.

Accordingly, based on these experiments described herein, the present compositions, kava extracts and compounds (e.g., dihydromethysticin, methysticin, dihydrokavain, kavain, desmethoxyyangonin and 11-methoxyyangonin) may be useful for both the treatment and prevention of cancer. They are also expected to have high safety profiles relative to typical cancer therapies and show superior efficacy and drug properties (e.g., oral bioavailability).

Introduction

Lung cancer is the leading cause of malignancy-related mortality because of its high incidence and the lack of effective treatments. Since tobacco usage contributes to 85-90% of its development, tobacco cessation is the most straightforward strategy for reducing lung cancer incidence and mortality. However, because of the addictive nature of tobacco, limited progress has been achieved in reducing tobacco usage. An alternative approach is to block or slow down tobacco carcinogen-induced lung cancer development via chemoprevention (Hecht et al., Nat. Rev. Cancer 2009; 9:476-88). Although a number of compounds have been identified as potential chemopreventive agents against lung tumorigenesis in animal models, their in vivo efficacy leaves ample room for improvement. Additional candidates with novel chemical structures, unique mechanisms, and better efficacy therefore need to be identified.

The A/J mice carry the pulmonary adenoma susceptibility 1 (Pas1) gene, tightly linked to the Kras oncogene (O'donnell et al., Cancer Lett 2006; 241:197-202), so that they have high susceptibility to lung tumor development. The A/J mice would develop lung tumor upon aging with high tumor incidence but low tumor multiplicity even without tobacco carcinogen treatment. With appropriate tobacco carcinogen treatment, A/J mice would develop lung tumors with 100% incidence and high multiplicity in a relatively short period of time (Hecht et al., Nat. Rev. Cancer 2009; 9:476-88). The tumors induced also have morphological, histological and molecular features similar to human lung adenocarcinomas (Malkinson, Lung Cancer 2001; 32:265-79). Therefore, the tobacco carcinogen-treated A/J mouse model is the most commonly used lung tumorigenesis model for evaluating chemopreventive agents with tumor multiplicity being the most practical endpoint.

Kava is an aqueous extract of the roots of *Piper methysticum* and traditionally serves as a beverage for South Pacific islanders. Kava had also been used to treat anxiety (Boerner et al., Phytomedicine 2003; 10 Suppl 4:38-49; Sarris J, et al., J Clin Psychopharmacol 2013; 33(5):643-648), in which case it was prepared as an organic extract. Epidemiological surveillance detected very low cancer incidence rates in several South Pacific countries, including lung cancer (Henderson et al., Fourth symposium on epidemiology and cancer registries in the pacific basin 1984:73-81; Henderson et al., Natl. Cancer Inst. Monogr. 1985; 69:73-81), and traditional kava usage may be a risk-lowering factor (Steiner G G., Hawaii Med. J. 2000; 59:420-2). Kava contains a class of unique chemicals, kavalactones (Rowe et al., Mini Rev Med Chem 2011; 11:79-83), which have not been reported to prevent tumorigenesis. Kava, particularly the anxiolytic preparation, also contains chalcone-based flavokawains, flavanones, and bornyl esters, which may inhibit cancer development.

It has recently been demonstrated that dietary supplement of an ethanol kava extract at a dose of 10 mg/g of diet, during initiation stage or post-initiation stage, effectively reduced lung adenomas multiplicity induced by eight gavage treatment of a mixture of the well-known tobacco carcinogens 4-(methylnitrosamino)-1-(3-pyridyl)-1-butanone (NNK) and benzo(a)pyrene (BaP) without adverse side effects in A/J mice (Johnson et al., Am J Chin Med 2011; 39:727-42; Johnson et al., Cancer Prev Res (Phila) 2008; 1:430-8). Since NNK and BaP induce adenoma formation via different mechanisms, the two-carcinogen model does not provide a feasible system to tackle questions regarding kava's underlying mechanisms and responsible chemicals. The studies described herein were designed to address these questions by using an NNK-induced lung tumorigenesis A/J mouse model. Similar studies using the BaP-induced lung tumorigenesis models may also be carried out.

Materials and Methods

Abbreviations

NNK, 4-(methylnitrosamino)-1-(3-pyridyl)-1-butanone; BaP, benzo(a)pyrene; $O^6$-mG, $O^6$-methylguanine; 7-pobG, 7-[4-(3-pyridyl)-4-oxobut-1-yl]guanine; $O^2$-pobdT, $O^2$-[4-(3-pyridyl)-4-oxobut-lyl]thymidine; $O^6$-pobdG, $O^6$-[4-(3-pyridyl)-4-oxobut-1-yl]-2'-deoxyguanosine; $O^2$-pobC, $O^2$-[4-(3-pyridyl)-4-oxobut-1-yl]cytidine; 7-mG, 7-methylguanine; $O^4$-mT, $O^4$-methylthymidine; CV, column volume; TLC, thin layer chromatography; H&E, hematoxylin and eosin; Pas1, pulmonary adenoma susceptibility 1; ANOVA, analysis of variance; PEITC, phenethyl isothiocyanate.

Chemicals, Reagents, and Animal Diets

NNK was synthesized (Hecht et al., Carcinogenesis 1983; 4:305-10). The kava product was purchased from Gaia Herbs, Inc. (Brevard, N.C.). It is an ethanol extract of the wild crafted lateral root from Vanuatu (standardized to 150 mg/mL total kavalactones). The AIN-93 purified diets from Harlan Teklad (Madison, Wis.) were used herein. The AIN-93G powdered diet started one week before the first dose of NNK and ended one week after the second dose of NNK; thereafter, it was replaced by AIN-93M powdered diet. $O^6$-methylguanine ($O^6$-mG) was purchased from Midwest Research Institute (Kansas City, Mo.). [$CD_3$]$O^6$-mG was purchased from Toronto Research Chemicals (Toronto, Ontario, Canada). 7-[4-(3-Pyridyl)-4-oxobut-1-yl]guanine (7-pobG), $O^2$-[4-(3-pyridyl)-4-oxobut-lyl]thymidine ($O^2$-pobdT), $O^6$-[4-(3-pyridyl)-4-oxobut-1-yl]-2'-deoxyguanosine ($O^6$-pobdG), and the corresponding [pyridine-$D_4$] analogues were synthesized (Lao et al., Chem Res Toxicol 2006; 19:674-82; Sturla et al., Chem Res Toxicol 2005; 18:1048-55). Micrococcal nuclease and phosphodiesterase II were from Worthington Biochemical Corporation (Lakewood, N.J.). Alkaline phosphatase was from Roche Molecular Biochemicals (Indianapolis, Ind.).

Kava Fractionation Preparation and Characterization

Previous investigation of traditional kava and kava from Gaia Herbs revealed that the Gaia Herbs preparation contained some minor non-polar constituents with high toxicity (Shaik et al., Bioorg Med Chem Lett 2009; 19:5732-6). The fractionation protocol of kava from Gaia Herbs using silica gel chromatography was developed and optimized, leading to three modalities—Fractions A, B, and C. Briefly, 350 mL of ethanolic kava extract was mixed with 350 g of silica gel. Solvents were evaporated under vacuum. Based on mass balance, 100 gram kava-adsorbed silica gel contained 28 gram kava residue. Kava-adsorbed silica gel (350 g) was loaded on a sample loading chamber and separated by a Biotage Semi-preparative system. The elution method was 28% ethyl acetate (EA) and 72% hexane (Hex) 5 column volumes (CV), followed by 90% EA and 10% Hex 4.1 CV, and then 35% MeOH and 65% EA 5.5 CV. Different eluents were analyzed by thin layer chromatography (TLC) and the desired eluents were combined with solvent removed to generate Fractions A, B, and C. The quantity of each fraction was measured and the integrity of each fraction was characterized by comparing the fingerprints of their $^1$H-NMR spectra. These fractions were also characterized by HPLC in comparison to traditional kava on a Beckman Coulter System Gold 126 solvent module with a 168 detector. A Clipeus C-18 column (5 μm, 250×4.6 mm) was used for the HPLC analyses. The flow rate used was 0.5 mL/min. The mobile phase A was water while B was acetonitrile. The time program used for the analyses was 70% B (0-5 min), 70-95% B (5-30 min), and 95% B (30-35 min). Compounds in Fractions B and C were further separated by normal phase silica gel chromatography and characterized by $^1$H-NMR and mass spectrometry.

Diet Preparation

Different kava modalities in the appropriate quantity were reconstituted in absolute ethanol (50 mL) and then mixed with AIN-93 powdered diet (150 g). Absolute ethanol (50 mL) was also mixed with AIN-93 powdered diet (150 g) for the control diet preparation. The reconstituted diets were dried under vacuum to remove ethanol, ground to a fine powder and mixed with additional AIN-93 powdered diet to the desired dose. The initial dose of kava (5 mg/g of diet) was chosen based on the results of previous study showing that kava at this dose was well tolerated in A/J mice while its lung cancer chemopreventive efficacy was similar to that at a higher dose (Johnson et al., Am J Chin Med 2011; 39:727-42).

Experiments Assessing Efficacy of Different Kava Regimens on Lung Adenoma Formation Induced by NNK in A/J Mice Female A/J mice, 5-6 weeks of age from the Jackson Laboratory (Bar Harbor, Me.), were handled according to animal welfare protocols approved by IACUC at the University of Minnesota. Upon arrival, mice were housed in the specific pathogen-free animal facilities of Research Animal Resources, University of Minnesota. After one-week acclimation, mice were weighed, randomized into different groups and switched to AIN-93G-powdered diet, defined as Day 1. The number of mice in each group was specified in the Result Section. On Day 7 and Day 14, mice in the negative control groups received 0.1 mL physiological saline solution while mice in the other groups received NNK (100 and 67 mg/kg respectively in 0.1 mL of physiological saline solution) via i.p. injection. At the end of Day 21, mice were switched to AIN-93M-powdered diet until the end of the study. Diet consumption was measured twice weekly and bodyweight was monitored weekly. All mice were euthanized with an overdose of carbon dioxide. The lungs were collected and tumors on the surface of the lung were counted.

Figure 4:
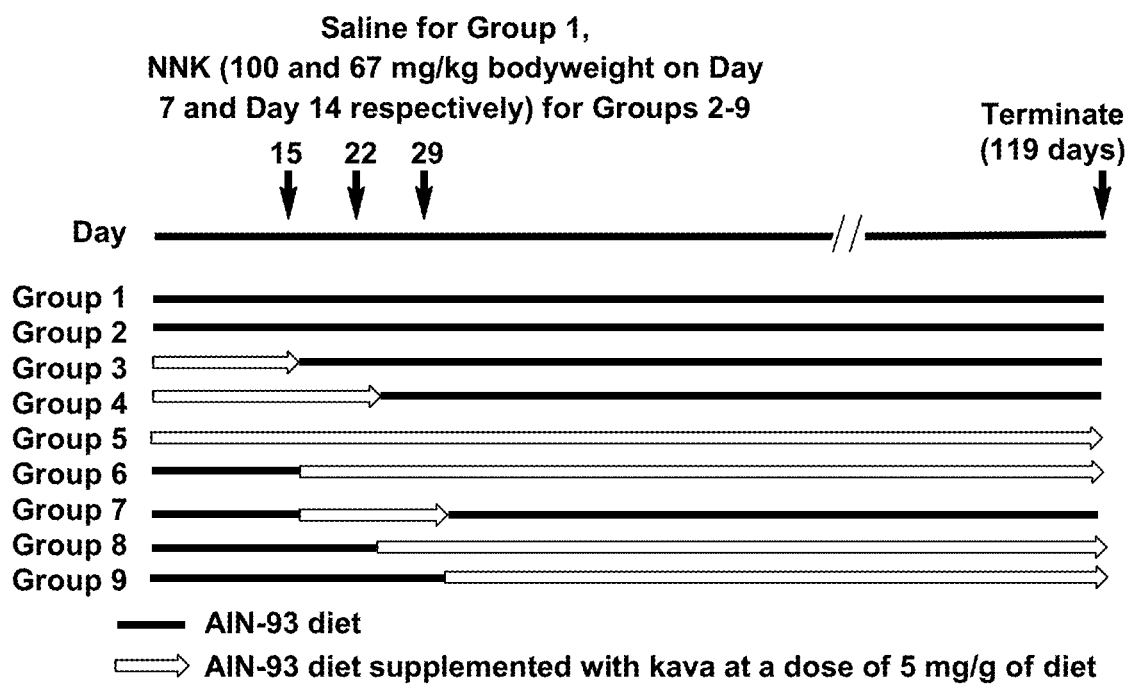
FIG. 4. Study design for evaluating the chemopreventive efficacy of different kava treatment regimens against NNK-induced lung adenoma formation in A/J mice. Beginning at the age of 6-7 weeks, groups of female A/J mice (Groups 2-9) were treated by two dosages of NNK (100 and 67 mg/kg bodyweight on Day 7 and Day 14 respectively) via i.p. injection in 0.1 mL saline. Mice in Group 1 were given two doses of saline (0.1 mL each) on Day 7 and Day 14. Mice in Groups 1 and 2 were maintained on standard diet treatment for the duration of the experiments. Mice in groups 3-9 were given a diet supplemented with kava at a dose of 5 mg/g diet according to the following schedules: Group 3 (Day 1-Day 14); Group 4 (Day 1-Day 21); Group 5 (Day 1-Day 119); Group 6 (Day 15-Day 119); Group 7 (Day 15-Day 28); Group 8 (Day 22-Day 119) and Group 9 (Day 29-Day 119). The study was terminated on Day 119.

For Experiment 1, mice were fed diet supplemented with/without kava at a dose of 5 mg/g of diet during specified periods (FIGS. 4 and 29) to define tumorigenesis-stage specificity. This study was terminated at the end of Day 119. For Experiment 2, mice were fed diet supplemented with/without kava at a dose of 5 mg/g of diet during Day 1-Day 14 (initiation stage only, FIG. 30). Half of the mice were terminated at the end of Week 25 (Day 175) and the other half at the end of Week 34 (Day 238). For Experiment 3, mice were given vehicle (PEG400:EtOH 9:1, 200 μL) or kava in the same vehicle (20 mg/mouse/day) via daily gavage with regimens specified in the Result Section. This study was terminated at the end of Day 119 (FIG. 31). For Experiment 4, mice were fed diet supplemented with kava at lower dosages to define dose-response pattern or different kava fractions at a dose of 2.5 mg/g of diet during Day 1-Day 14. This study was terminated at the end of Day 119 (FIG. 32).

Experiments Evaluating Effect of Kava on Acute DNA Adduct Formation by NNK in A/J Mice After one-week acclimation, A/J mice were weighed and randomized into sixteen groups (3 mice per group) and switched to AIN-93G-powdered diet with the date being defined as Day 1. Mice in Groups 1, 2, 4, 6, 8, 10, and 12 were given AIN-93G diet through the study. Mice in Groups 3, 5, 7, 9, 11 and 13 were given AIN-93G diet supplemented with kava at a dose of 5 mg/g of diet through the study except for mice in Groups 9, 11, and 13, which were switched to plain AIN-93G diet one day after NNK injection to mimic stopping kava treatment one day after the last NNK treatment in the long-term lung tumorigenesis studies. Mice in Groups 14-16 were given AIN-93G diet supplemented with Fractions A, B, and C respectively at a dose of 2.5 mg/g of diet through the study. On Day 7, mice in Group 1 received 0.1 mL physiological saline solution while mice in the other groups received NNK (100 mg/kg in 0.1 mL physiological saline solution) via i.p. injection. Mice in Groups 1, 2, and 3 were euthanized 4 h after NNK injection. Mice in Groups 4 and 5 were euthanized 8 h after NNK injection. Mice in Groups 6, 7, 14, 15, and 16 were euthanized 24 h after NNK injection. Mice in Groups 8 and 9 were euthanized 48 h after NNK injection. Mice in Groups 10 and 11 were euthanized 96 h after NNK injection. Mice in Groups 12 and 13 were euthanized 2 weeks (336 h) after NNK injection. All mice were euthanized with an overdose of carbon dioxide. The lungs were harvested, snap frozen in liquid $N_2$ and stored at −80° C. until DNA isolation.

Isolation and Quantification of DNA Adducts in the Lung Tissues by LC-ESI-MS/MS

DNA was isolated from the whole lung tissue of each individual mouse following Puregene DNA isolation protocol (Qiagen Corp, Valencia, Calif.) (Urban et al., Chem Res Toxicol 2012; 25:2167-78). 7-pobG, $O^2$-pobdT, $O^6$-pobdG, and $O^6$-mG were quantified by LC-ESI-MS/MS, following established protocols (Urban et al., Chem Res Toxicol 2012; 25:2167-78; Peterson et al., Cancer Res 1991; 51:5557-64).

Lung Tumor Histopathology

4-μm-thick sections made from formalin-fixed and paraffin embedded lung tissues were stained with hematoxylin and eosin (H&E).

Statistical Analyses

Data on lung adenoma multiplicity were reported as mean±SD (n=5-40). One-way analysis of variance (ANOVA) was used to compare means among NNK and NNK+kava modality groups for Experiments 1, 3, and 4. Dunnett's test was used for comparisons of the number of tumors on the surface of the lung between NNK control and kava modality treatment groups. p-value≤0.05 was considered statistically significant. For Experiment 2, unpaired t-test was used for comparison between NNK control and kava treatment groups. Two-sided p-value≤0.05 was considered statistically significant. Data on DNA adducts were reported as mean±SD (n=3). For the time-course study, unpaired 1-test was used for comparisons between NNK control and kava treatment groups. Two-sided p-value≤0.05 was considered statistically significant: *p<0.05, p<0.01, and *p<0.001. For the 24-h time point study, one-way ANOVA was used to compare means. Dunnett's test was used for comparisons between NNK control and kava modality treatment groups. p-value≤0.05 was considered statistically significant. All analyses were conducted in GraphPad Prism 4 (GraphPad Software, Inc. La Jolla, Calif.).

Results

Effect of Kava Treatment Schedule with Respect to NNK Exposure on Lung Adenoma Formation in A/J Mice—Experiment 1

To test whether kava inhibited a specific stage of NNK-induced lung tumorigenesis, A/J mice were given two dosages of NNK (100 and 67 mg/kg of bodyweight on Day 7 and Day 14 respectively via i.p. injection). NNK-treated A/J mice were given diet supplemented with kava at a dose of 5 mg/g of diet during different periods of time in reference to NNK exposure. Both the adenoma incidence (presence of one detectable surface adenoma) and the number of adenomas on the lung surface at the end of Day 119 were quantified (FIG. 29).

As expected, A/J mice without NNK treatment had low adenoma incidence (10%) and low adenoma multiplicity (0.1±0.3 lung adenoma/mouse) while NNK-treated A/J mice had 100% adenoma incidence and high adenoma multiplicity (17.5±4.8 lung adenoma/mouse). Kava treatment regimens that started after the final NNK treatment (Groups 6-9, i.e., post-initiation) had no effect on adenoma incidence. Such treatments also had little effect on adenoma multiplicity, except for the Day 15-119 regimen (Group 6), which reduced adenoma multiplicity by 24% (13.3±4.3 lung adenoma/mouse, p<0.05). On the other hand, kava treatments that preceded and covered the NNK exposure period (Groups 3-5, i.e., initiation stage) not only reduced adenoma incidence by 67-87% but also reduced adenoma multiplicity by ~99%, to a level similar to mice without NNK treatment, which is not expected with respect to its outstanding efficacy. None of the long-term kava treatment regimens (Groups 5, 6, 8 and 9) caused >10% reduction in bodyweight, and the short-term treatment regimens (Groups 3, 4 and 7) did not reduce bodyweight relative to NNK-treated mice (Group 2). None of the kava treatment regimens caused significant changes in liver weight in comparison to NNK-treated mice (Group 2). These data indicated a complete blocking effect of kava on NNK-induced initiation of lung tumorigenesis, with a modest post-initiation inhibitory efficacy.

Effect of Kava on Long-Term Lung Tumorigenesis in A/J Mice—Experiment 2

Figures 5A, 5B, 5C:
FIGS. 5A-5C. Representative photomicrographs H&E-stained sections of lungs (n=4 in each group) from negative control mice (FIG. 5A), mice with NNK alone (FIG. 5B), and mice with NNK plus kava at a dose of 5 mg/g of diet (FIG. 5C).

To validate the anti-initiation efficacy of the short kava treatment during NNK treatment period (Day 1-Day 14) and to determine whether such inhibition would persist through later stages of tumorigenesis, the kava and NNK treatment experiments for the initiation stage were replicated and the tumor status at Week 25 (Day 175) and Week 34 (Day 238) was analyzed. As shown in FIG. 30, A/J mice without NNK treatment had no adenoma and NNK-treated A/J mice had 100% adenoma incidence and high adenoma multiplicity (18.1±5.1 lung adenoma/mouse) at Week 25. Kava at a dose of 5 mg/g of diet given during Day 1-Day 14 reduced adenoma incidence by 73% and adenoma multiplicity by 98.5%. As expected for longer duration for tumors to grow, A/J mice at Week 34 had higher adenoma multiplicity (26.5±7.8 lung adenoma/mouse) than those at Week 25. A/J mice without NNK treatment also had higher incidence (25%) and multiplicity (0.5±1.0 lung adenoma/mouse) of spontaneous tumors than those at Week 25. Kava given during Day 1-Day 14 did not reduce adenoma incidence but dramatically reduced adenoma multiplicity by 97.7% (1.1±0.6 lung adenoma/mouse). FIG. 5 shows representative photomicrographs of sections of lung from mice without NNK treatment (FIG. 5A), mice with NNK treatment (FIG. 5B), and mice with NNK and kava treatment (FIG. 5C), which confirmed tumor reduction in the lung interior with kava treatment to the same magnitude as enumerated by counting the visible lung surface lesions. This kava treatment regimen caused no changes in mouse bodyweight and liver weight relative to the NNK-control groups. The data from this experiment not only confirmed the initiation-specific inhibitory efficacy of kava on NNK-induced lung tumorigenesis but also demonstrated the long-lasting protective nature of such a brief treatment.

Effect of Daily Gavage of Kava on Lung Adenoma Formation in A/J Mice—Experiment 3

Given potential pharmacokinetic differences between kava consumption in humans (most practical as a bolus dose through dietary supplement pill/drink) vs. that of continuous rodent food intake in the experiments so far, an experiment to explore whether once daily gavage of kava might be as effective in preventing NNK-induced adenoma formation in A/J mice was carried out. The dose of kava, 20 mg/mouse/day, was chosen based on the fact that A/J mouse consumes 3-4 g of diet/day and the kava dose in diet was 5 mg/g of diet. In one regimen, once daily kava gavage started one day before the first NNK treatment and continued until one day after the second NNK treatment—Group 3 (FIG. 31). In the second regimen, once daily kava gavage started one day before the first NNK treatment, ended one day after the first NNK treatment, resumed one day before the second NNK treatment and ended one day after the second NNK treatment—Group 4 (FIG. 31). When the incidence and number of adenoma on the lung surface at the end of Day 119 were quantified (FIG. 31), A/J mice without NNK treatment had low adenoma incidence (20%) and low adenoma multiplicity (0.2±0.4 lung adenoma/mouse) while NNK-treated A/J mice had 100% adenoma incidence and high adenoma multiplicity (16.6±3.1 lung adenoma/mouse). Both kava gavage regimens reduced adenoma incidence (60-100%) and reduced adenoma multiplicity by ~99%. None of these regimens caused significant bodyweight or liver weight change in comparison to mice in Group 2. These data therefore convincingly established the feasibility of using kava in as few as 3 once-daily bolus treatments (i.e., one dose before, during and after the NNK injection) to block NNK-induced adenoma initiation. Similar experiments may be designed and performed to test whether a single dose shortly before or concurrent with NNK would be sufficient.

Preparation and Characterization of Three Kava Fractions

Figure 6:
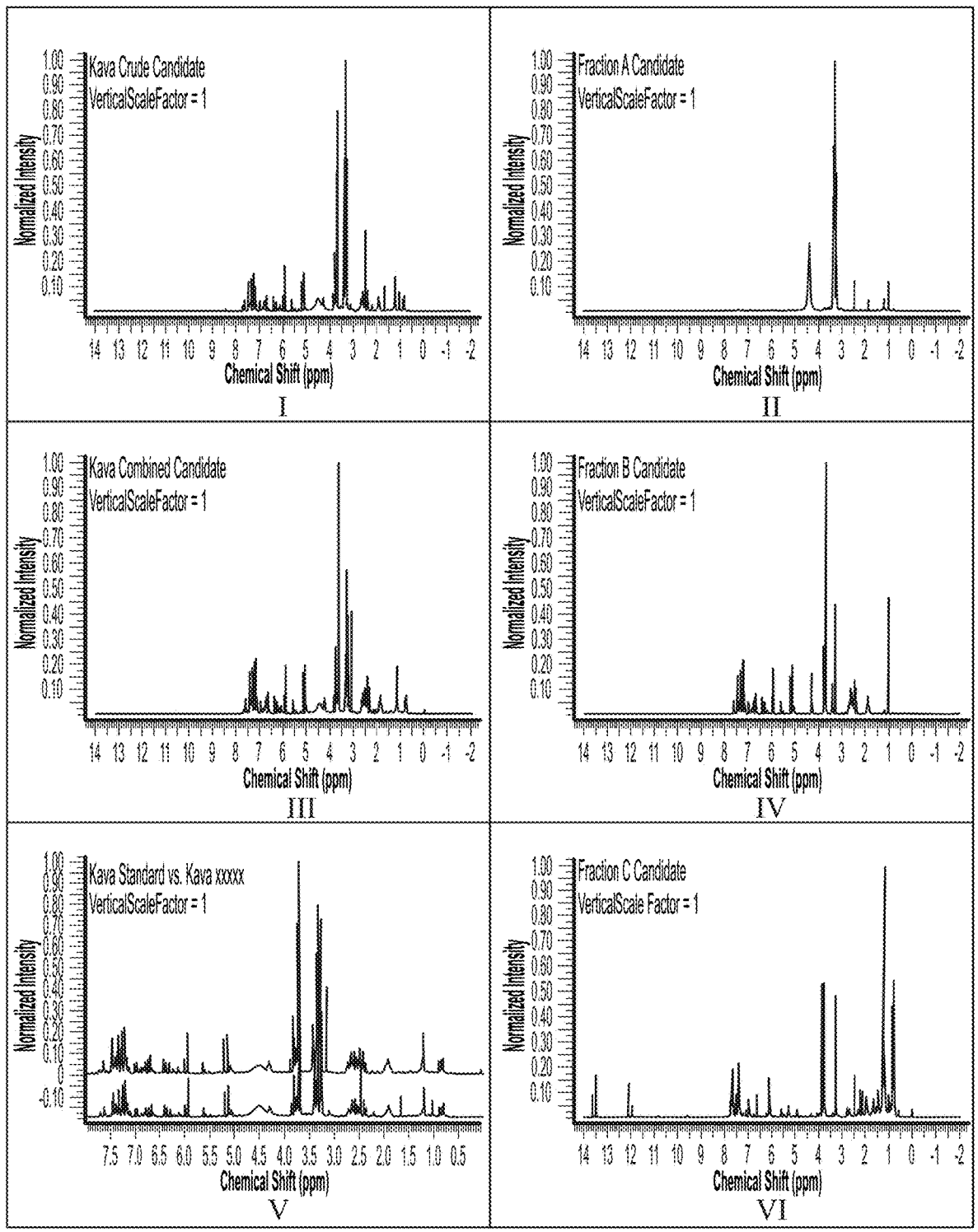
FIG. 6. $^1$H-NMR spectra of different kava fractions and the mass balance of each fraction. I. Kava; II. Fraction A; III. Reconstituted kava from Fractions A, B, and C; IV. Fraction B; V, Comparison between Kava (bottom line) and reconstituted kava (top line) from Fractions A, B, and C; VI. Fraction C; VII. Mass balance of each fraction.
Figure 6:
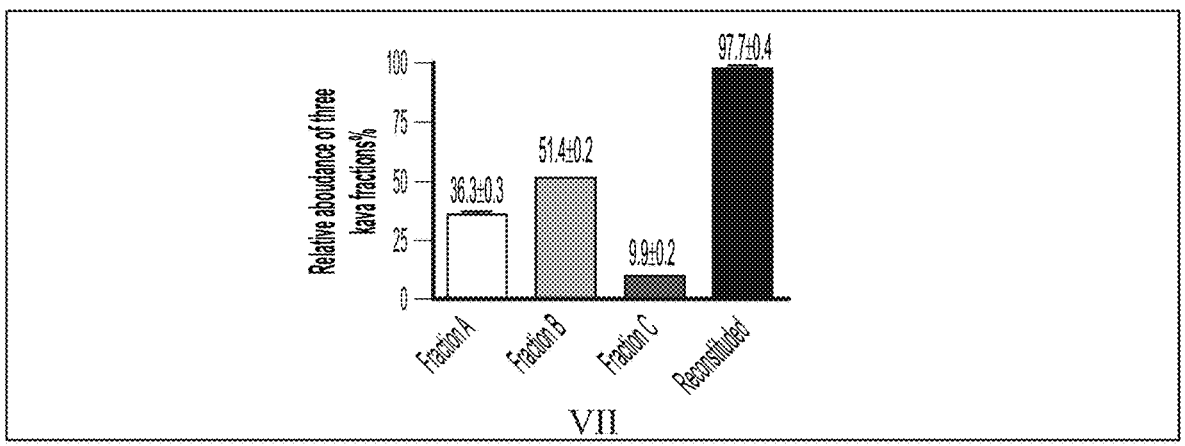
Figure 7:
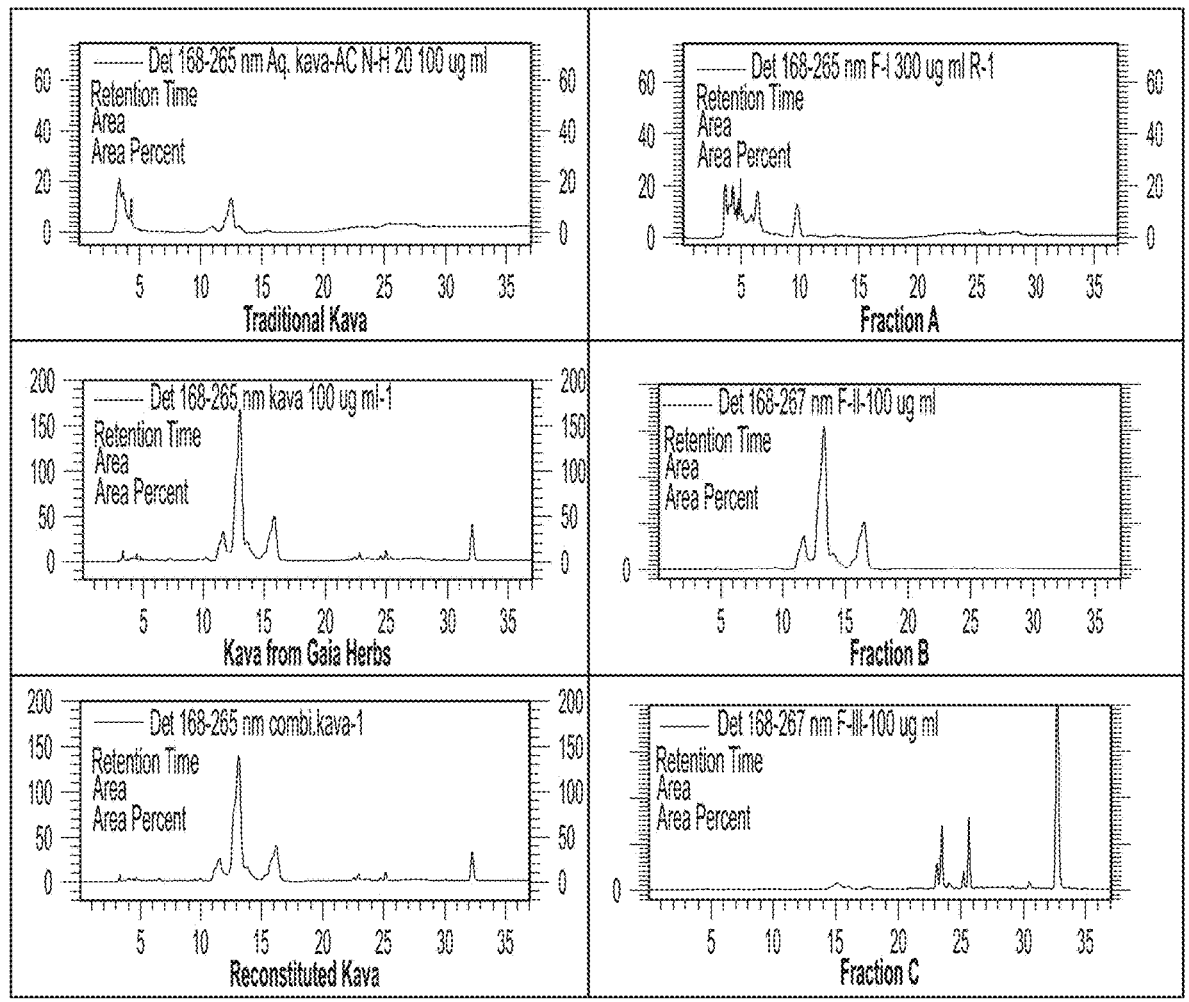
FIG. 7. HPLC traces of traditional kava, kava from Gaia Herbs, reconstituted kava, and Fractions A, B, and C.

Kava from Gaia Herbs was separated into three fractions—Fractions A, B, and C with nineteen repeats. The chemical profile of each fraction was characterized by $^1$H-NMR to ensure the reproducible integrity of each modality (FIG. 6). The mass of each fraction was determined (FIG. 6). Fractions A, B, and C accounted for 36.3%, 51.4%, and 9.9% of the mass balance of kava, respectively. The quantitative mass balance (97.7%) suggests that most, if not all, components were recovered. Reconstituted kava from Fractions A, B, and C also revealed no difference in composition from the original kava preparation, based on $^1$H-NMR and HPLC analyses (FIGS. 6 and 7). HPLC analyses also showed that Fraction C contained chemicals not detectable in traditional kava (FIG. 7).

Figure 8:
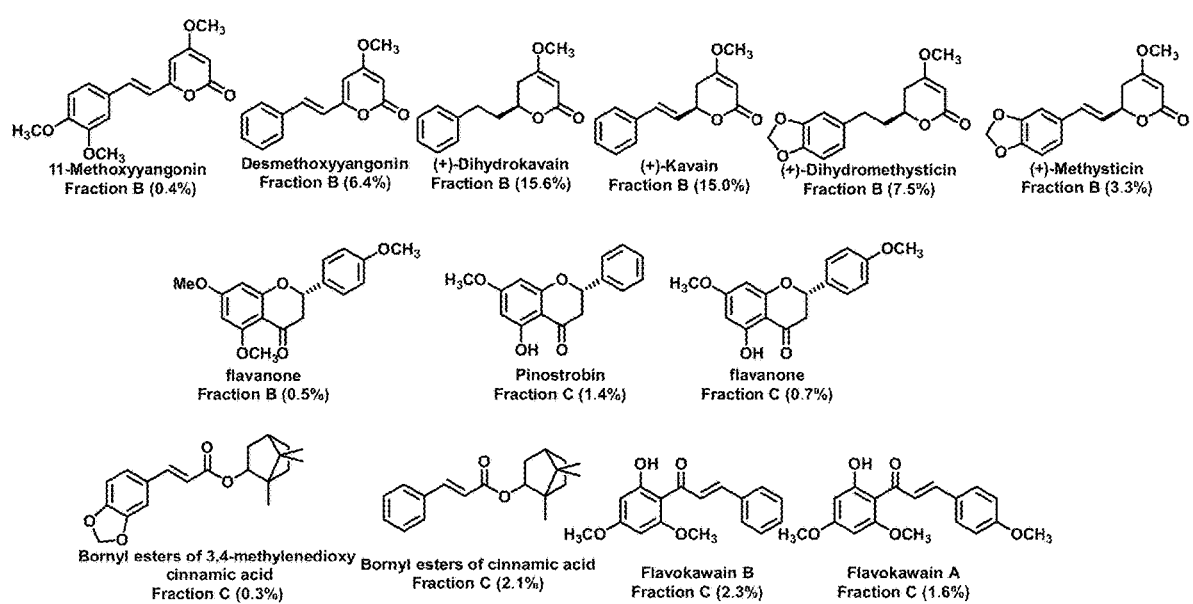
FIG. 8. Chemicals isolated from kava and their natural abundance.
Figure 9:
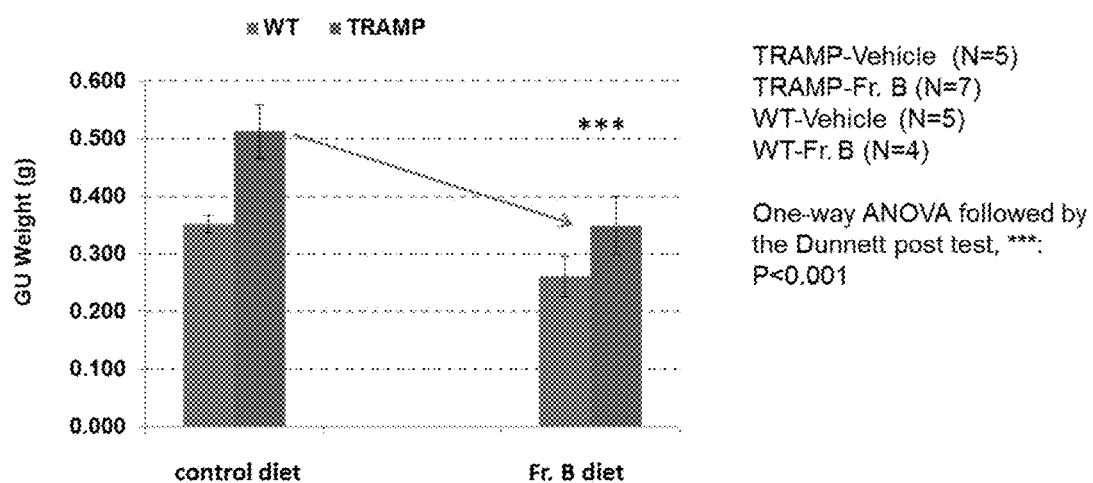
FIG. 9. Genito-urinary track weight (16 weeks of age) (excluding 1 tumor bearing mouse). For each group, the bar on the left represents wildtype mice and the bar on the right represents TRAMP mice.
Figure 10:
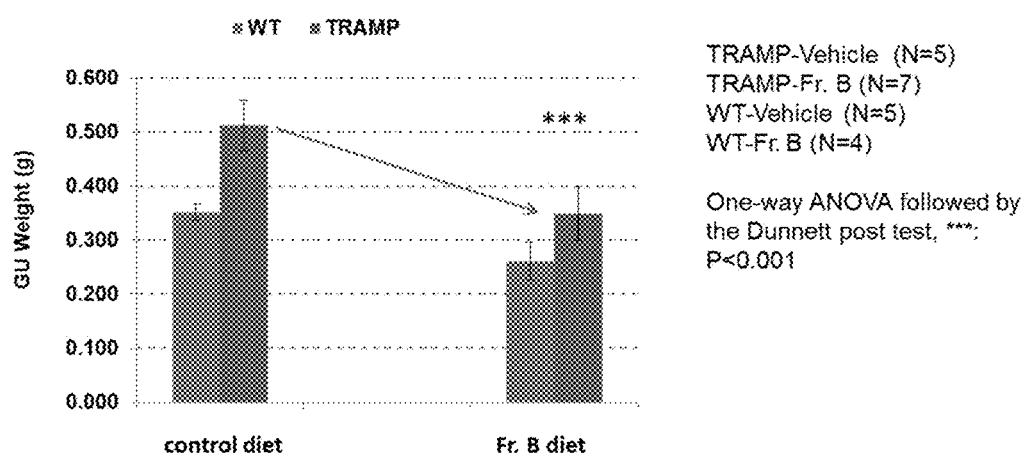
FIG. 10. Prostate Weight (16 weeks of age). For each group, the bar on the left represents wildtype mice and the bar on the right represents TRAMP mice.
Figure 11:
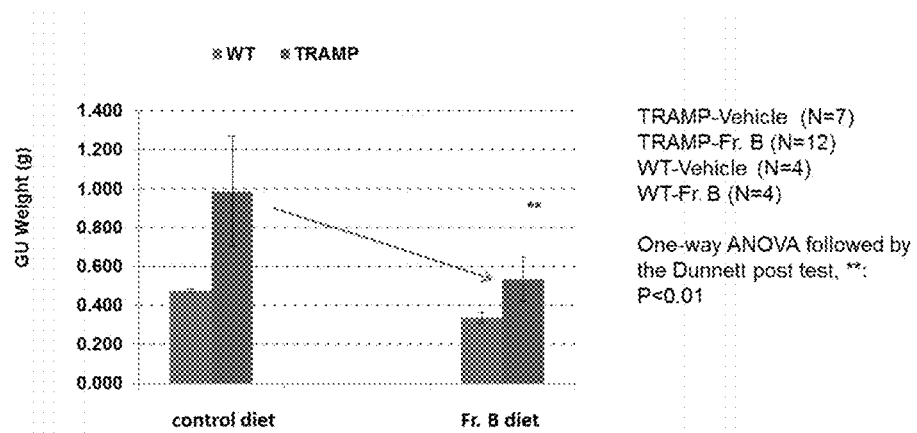
FIG. 11. GU Weight (28 weeks of age) (excluding tumor-bearing mice). For each group, the bar on the left represents wildtype mice and the bar on the right represents TRAMP mice.
Figure 12:
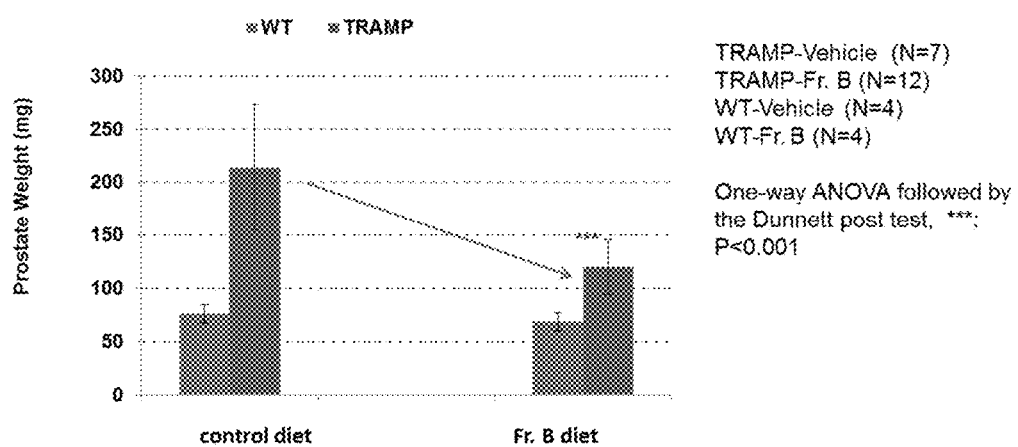
FIG. 12. Prostate Weight (28 weeks of age) (excluding tumor-bearing mice). For each group, the bar on the left represents wildtype mice and the bar on the right represents TRAMP mice.

The major chemicals in Fraction B and C were isolated, characterized by $^1$H-NMR and mass spectrometry, and abundance determined (FIG. 8). All these chemicals have been previously identified from kava products (Duke J, Dr. Duke's phytochemical and ethnobotanical databases, in, 2013 pp. http://www.ars-grin.gov/duke/.). Fraction B contains six kavalactones and one flavanone. Fraction C includes two additional flavanones, two bornyl esters, and two chalcone-based flavokawains A and B. Chemicals in Fraction A were not characterized because the chemopreventive efficacy data showed that Fraction A was the least efficacious and that Gaia Herbs kava's chemopreventive potential could be recapitulated by Fraction B (FIG. 32).

Estimating Minimum Effective Dosage and Searching for Active Fraction Against NNK-Induced Lung Adenoma Formation in A/J Mice—Experiment 4

To determine the minimum dose of kava that could effectively inhibit NNK-induced lung adenoma formation in A/J mice, the same carcinogen protocol as above to initiate tumorigenesis was used. NNK-treated A/J mice were given diet supplemented with kava at a dose of 5, 2.5, and 1.25 mg/g of diet during Day 1-Day 14. The incidence and number of adenoma on the lung surface at the end of Day 119 were quantified (FIG. 32). Similar to previous results, A/J mice without NNK treatment had low adenoma incidence (20%) and multiplicity (0.2±0.4 lung adenoma/mouse) while NNK-treated A/J mice had 100%/adenoma incidence and high adenoma multiplicity (16.0±5.2 lung adenoma/mouse). Kava treatments, at all dosages, reduced adenoma incidence by 73-87% and reduced adenoma multiplicity by ~99%. These data suggested that future experiments would be needed to explore even lower dosages to define the minimum effective dose of kava to block tumor initiation in this model.

In this study, the efficacy of the three kava fractions at a dose of 2.5 mg/g of diet was also evaluated to rank their anti-initiation efficacy (FIG. 32, Groups 6-8). Fraction A, equivalent to kava at a dose of 6.9 mg/g of diet based on its abundance in kava, caused no reduction in adenoma incidence and only weakly reduced adenoma multiplicity by 25% (12.0±5.0 lung adenoma/mouse, p<0.01). Fraction B, equivalent to kava at a dose of 4.9 mg/g of diet, reduced adenoma incidence by 93% and reduced adenoma multiplicity to baseline level (0.1±0.5 lung adenoma/mouse, p<0.01). Fraction C, equivalent to kava at a dose of 25.2 mg/g of diet, did not reduce adenoma incidence but reduced adenoma multiplicity by 70% (3.5±2.5 lung adenoma/mouse, p<0.01). None of these regimens caused significant bodyweight or liver weight changes in comparison to mice in Group 2. The data suggest the Fraction B contained the overwhelming majority, if not all, of the active compounds, Fraction C contained minor amount whereas Fraction A contained literally none.

Figure 1B:
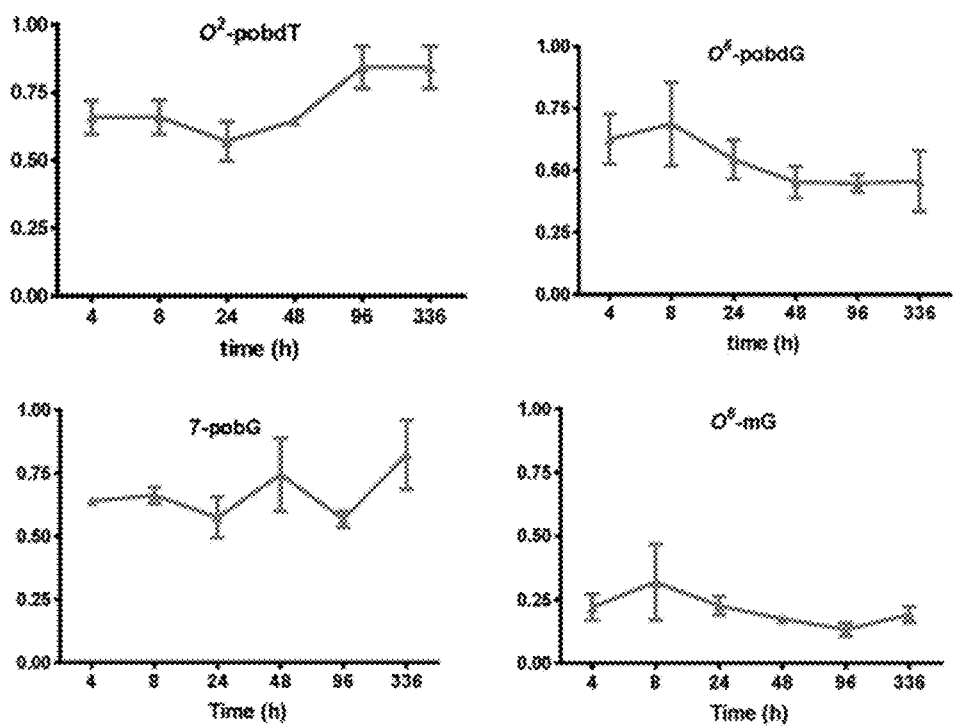

Effect of Kava and its Fractions on DNA Damage Induced by NNK in A/J Mouse Lung Tissues Since the data convincingly established the highly selective anti-initiation efficacy of kava and its Fraction B against NNK-induced lung adenoma formation, reduction of NNK-induced DNA damage as a plausible mechanism of chemoprevention was focused on next. Additional experiments to collect lung tissues were designed to characterize the time-course profiles of four NNK-derived DNA adducts (7-pobG, $O^2$-pobdT, $O^6$-pobdG and $O^6$-mG) in the lung tissues of the A/J mice upon kava exposure at a dose of 5 mg/g of diet. As expected, no NNK-derived DNA adducts were detected in the negative control mice (data not shown) while significant amounts of all four DNA adducts were detected in mice with NNK treatment (FIG. 1A). Kava treatment reduced the quantity of all four DNA adducts (FIG. 1A). When the abundance of each DNA adduct was normalized relative to its time-controlled NNK-treatment group (FIG. 1B), the extents of reduction in 7-pobG, $O^2$-pobdT, and $O^2$-pobdG were similar (30-40%), particularly during the first 24 h after NNK treatment when the contribution of DNA repair and intrinsic instability of these adducts are less important. For $O^6$-mG, however, the reduction was 70-80% (FIG. 1B). Because there were no differences in the relative abundance of any of these four DNA adducts at different time points after NNK treatment (FIG. 1B), kava-induced reduction in these DNA adducts is more likely mediated through the inhibition of their formation instead of the activation of DNA repair mechanisms.

Figure 1C:
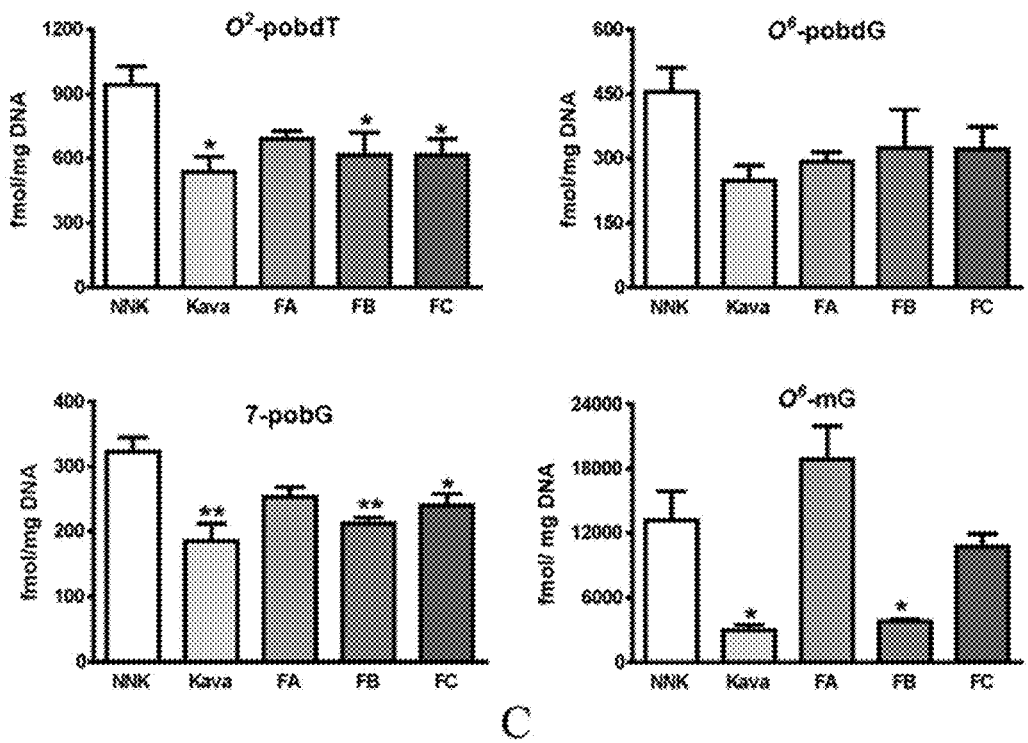
Figure 1D:
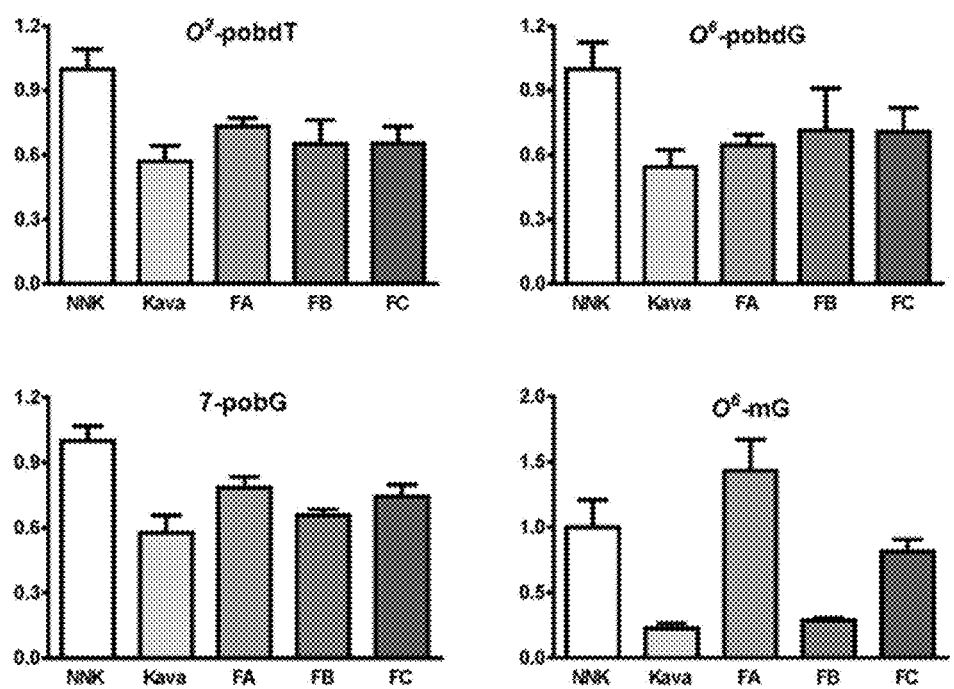

The effect of Fractions A, B, and C at a dose of 2.5 mg/g of diet on NNK-induced DNA adducts 24 h after NNK treatment were evaluated next. As shown in FIG. 1C, all kava fractions reduced NNK-induced DNA damage. However, the extents of reduction in 7-pobG, $O^2$-pobdT, and $O^6$-pobdG were very similar (FIG. 1D) and had no correlation with their distinct capacities in blocking lung adenoma formation. The extents of reduction in $O^6$-mG, on the other hand, were quite different. Fraction B greatly reduced $O^6$-mG (72%) while Fraction A and C had no effect on $O^6$-mG. The extent of reduction in $O^6$-mG correlated with their capabilities in reducing lung adenoma multiplicity (FIG. 32). These data suggest that blocking the formation of $O^6$-mG (and possibly other methylation adducts) in the lung DNA by active compounds in kava Fraction B was a likely mechanism for its efficacy against NNK-induced lung tumorigenesis in this model.

DISCUSSION

The results from this study clearly demonstrated that kava, when given before and during NNK treatment period (initiation stage), was highly efficacious in preventing lung adenoma formation in A/J mice, with a ~99% reduction in adenoma multiplicity at a dose of as low as 1.25 mg/g of diet. The minimum effective dose remains to be defined. Such treatments also reduced lung tumor incidence. A similar degree of chemopreventive effect was maintained even when the studies were terminated at later stages, suggesting that kava blocks lung tumorigenesis instead of slowing down the process. Furthermore, the data convincingly established the feasibility of using kava in as few as 3 once-daily bolus treatments (i.e., before, during and after the NNK injection) to block the adenoma initiation activity of NNK. While these data further substantiated the chemopreventive potential of kava against tobacco-induced lung cancer, they also demonstrated a new paradigm of highly effective initiation-stage specificity of kava against this carcinogen. Such drastic efficacy has not been reported previously in literature except for several synthetic derivatives of phenethyl isothiocyanate (PEITC) (Alworth et al., Carcinogenesis 1993; 14:1711-3).

On the other hand, kava showed much lower efficacy when its treatment started after the second NNK administration, suggesting that kava at this dose and format mainly blocks the initiation of NNK-induced lung tumorigenesis. These results differed from those of previous studies, which demonstrated that kava at a dose of 10 mg/g of diet decreased NNK- and BaP-induced adenoma formation in A/J mice in the post-initiation stage (i.e., kava treatment started one day after the final dose of carcinogen treatment) as well as in the initiation stage (Johnson et al., Cancer Prev Res (Phila) 2008; 1:430-8). There are several differences between these studies that may account for this apparent discrepancy. First of all, the routes of carcinogen administration and the dose-intensity were different. NNK in this study was given by i.p. injection (2 weekly injections) whereas previous work involved gavage of NNK and BaP mixture (8 weekly gavages). These may lead to different metabolic processing of the carcinogen(s) and reactive metabolites toward DNA and thereby different pathogenetic alterations in the target tissues in these models. Secondly, the kava treatment regimen in this study (Group 6), most closely mimicking that used in the previous study, displayed a modest reduction in lung adenoma multiplicity (FIG. 29), albeit to a lesser extent than those in the previous study. This might be explained by the dosage difference in these studies. Finally, kava did not completely block NNK- and BaP-induced lung adenoma formation when it was given during the initiation phase even at a dose of 10 mg/g of diet (Johnson et al., Cancer Prev Res (Phila) 2008; 1:430-8). Compared with the high efficacy against NNK-induced initiation in the current study, it is possible that kava is less effective in blocking BaP-induced lung tumor initiation.

In the search for the active compound(s), a highly reproducible fractionation protocol was developed, separating kava into three fractions. Fraction A contains the polar chemicals, Fraction B contains the chemicals with intermediate polarity, and Fraction C contains the non-polar chemicals not detectable in traditional kava. When evaluated at a dose of 2.5 mg/g of diet, Fractions A and C, equivalent doses much higher than kava at 5 mg/g of diet, only weakly reduced lung adenoma multiplicity with no reduction in tumor incidence. Fraction B, on the other hand, completely blocked NNK-induced lung adenoma formation at a dose equivalent to kava at 5 mg/g of diet. These data clearly demonstrate that Fraction B fully recapitulates kava's lung chemopreventive efficacy and contains the active compounds, whereas Fractions A and C contain none or little. Six kavalactones have been identified in Fraction B, accounting for 94% of its mass balance. Although there had been no report of their efficacy in any in vivo tumorigenesis models, these kavalactones are likely responsible for kava's efficacy in blocking NNK-induced lung tumorigenesis in A/J mice. It is noteworthy that Fraction B is free of flavokawains A and B that may contribute to kava's hepatotoxic risk (Zhou P, et al., Faseb J. 2010; 24:4722-32). Although flavokawains A and B have revealed anticancer activities in several xenograft models (Zi et al., Cancer Res 2005; 65:3479-86; Tang Y et al., Int J Cancer 2010; 127:1758-68; Lin et al., J Nutr Biochem 2012; 23:368-78), results from current studies indicate that they are not the active compounds against NNK-induced lung tumorigenesis initiation, consistent with the results from the previous study (Johnson et al., Am J Chin Med 2011; 39:727-42).

Figure 2:
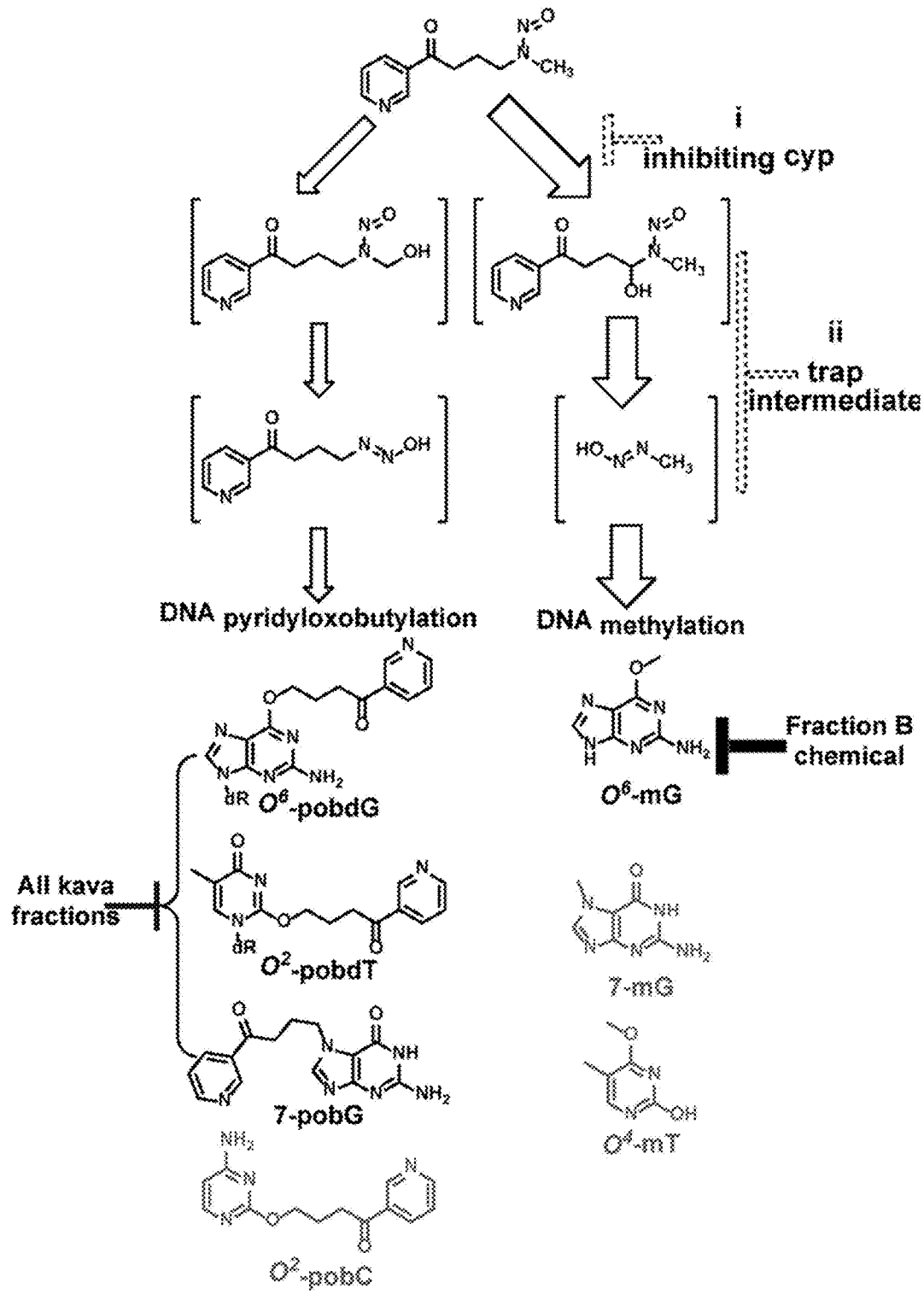
FIG. 2. Two metabolic activation pathways of NNK leading to different methylated-vs. 4-(3-pyridyl)-4-oxobut-1-yl (pob)-DNA adducts. Solid blocks indicate measured reduction in different classes of DNA adducts, as exemplified by $O^6$-mG vs. 7-pobG, $O^2$-pobdT, and $O^6$-pobdG. Dashed blocks indicate hypothetical points of action by kava chemicals or their metabolites: (i) to differentially inhibit cytochrome p450 isoform-mediated NNK metabolic activation or (ii) directly react with NNK methylene hydroxylation metabolites as chemical traps.
Figure 3:
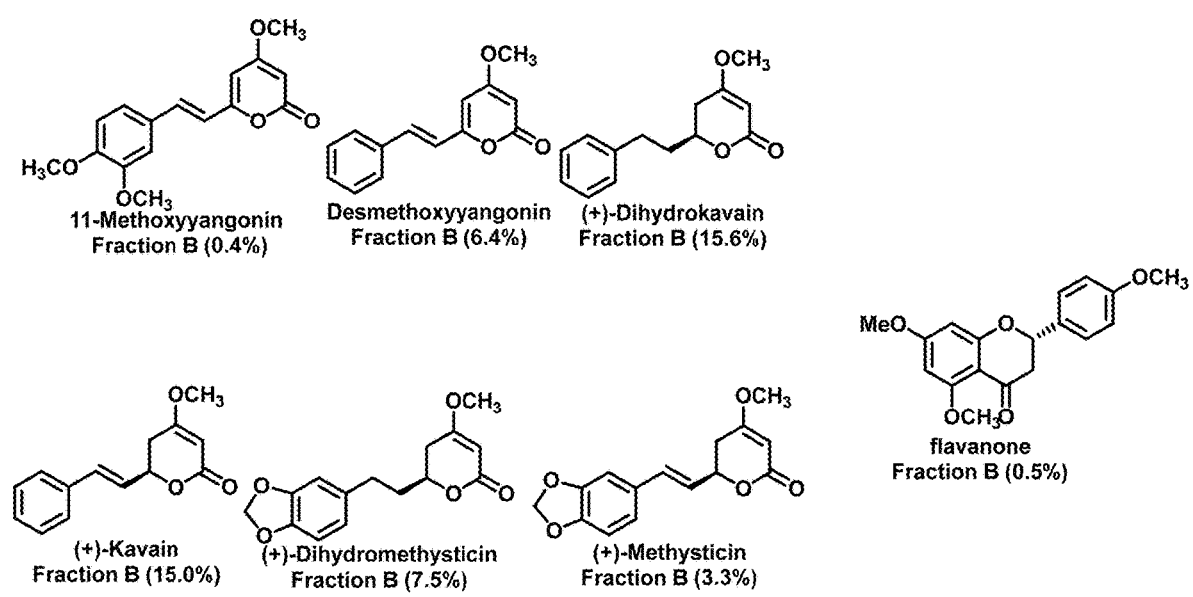
FIG. 3. Compounds in Fraction B, including dihydromethysticin and methysticin.

Given the highly selective anti-NNK-initiation action of kava and its fraction B, their effect on NNK-induced DNA damage in lung tissue was characterized as a possible mechanism. NNK, an asymmetrical nitrosamine, can be activated to two types of DNA reactive species via different hydroxylation pathways (FIG. 2). Methyl hydroxylation generates 4-oxo-4-(3-pyridyl)-1-butanediazohydroxide, which leads to a panel of DNA adducts, including 7-pobG, $O^2$-[4-(3-pyridyl)-4-oxobut-1-yl]cytidine ($O^2$-pobC), $O^2$-pobdT, and $O^6$-pobdG (Urban et al., Chem Res Toxicol 2012; 25:2167-78). Methylene hydroxylation generates methanediazohydroxide, leading to another set of DNA adducts, including 7-methylguanine (7-mG), $O^6$-mG, and $O^4$-methylthymidine ($O^4$-mT). The abundance of methylation DNA adducts are typically 10-20 fold more than those of the pob DNA adducts, likely due to a combination of preferential methylene hydroxylation of NNK and higher reactivity of methanediazohydroxide intermediate (Peterson et al., Cancer Res 1991; 51:5495-500). Four of these DNA adducts were analyzed in the lung, 7-pobG, $O^2$-pobdT, $O^6$-pobdG, and $O^6$-mG, because of their better stability, their representation of both pathways of NNK activation, and their potential tumorigenicity (Urban et al., Chem Res Toxicol 2012; 25:2167-78; Peterson et al., Cancer Res 1991; 51:5557-64; Loechler et al., Proc Natl Acad Sci USA 1984; 81:6271-5).

Surprisingly, kava treatment causes different extents of reduction in these four DNA adducts with high preference on $O^6$-mG. To our knowledge, kava is the first candidate that demonstrates such a unique mechanism. Given that the POB adducts are generated via methyl hydroxylation of NNK while $O^6$-mG is generated via methylene hydroxylation (FIG. 2), kava Fraction B chemicals may preferentially inhibit NNK methylene hydroxylation over methyl hydroxylation. It is also possible that Faction B chemicals better react with and trap methanediazohydroxide over 4-oxo-4-(3-pyridyl)-1-butanediazohydroxide, leading to the observed preferential reduction in $O^6$-mG. Nevertheless, work from Peterson et al. shows that $O^6$-mG has a strong and positive correlation with lung tumor multiplicity in A/J mice (Peterson et al., Cancer Res 1991; 51:5557-64). A/J mice with increased DNA repair capacity specific to $O^6$-mG are less susceptible to NNK-induced lung tumorigenesis as well (Liu et al., Carcinogenesis 1999; 20:279-84). In addition, the miscoding properties of $O^6$-mG have been well established (Loechler et al., Proc Natl Acad Sci USA 1984; 81:6271-5). These results argue for the high tumorigenicity of $O^6$-mG relative to the POB adducts and the possible cause-effect of its reduction by kava and Fraction B chemicals to their impressive anti-initiation efficacy.

In summary, kava blocks NNK-induced lung tumorigenesis in A/J mice with high selectivity for the initiation stage. Mechanistically kava Fraction B chemicals preferentially reduces NNK-induced $O^6$-mG DNA adduct in the lung tissues. These results also suggest that kavalactones in Fraction B may be the active compounds.

Example 2

Effect of Dietary Kava Fraction B Supplement on Carcinogenesis in Transgenic Adenocarcinoma of the Mouse Prostate (TRAMP) Mice Introduction of the Model In the TRAMP model, the rat probasin promoter drives transgenic "prostate-specific" expression of simian virus 40 (SV40) T-antigen (T-Ag) and small t-antigen; T-Ag binds and inactivates the retinoblastoma (Rb) and p53 tumor suppressor genes; and small t-antigen also drives cell proliferation (Greenberg et al, PNAS, 1995).

There are at least 2 distinct lineages of carcinogenesis in this model (Chiaverotti et al, *Am J Pathol*, 2008; Huss et al, *Neoplasia*, 2007, Wang et al, *Prostate*, 2011). One lineage is the androgen receptor (AR)-dependent glandular epithelial lesions, which usually involve the dorsal-lateral prostate (DLP) lobes, less for anterior (AP) and ventral (VP) lobes. The other lineage is the AR-independent neuroendocrine (NE)-like poorly differentiated (PD) carcinomas: life-time NE-Ca incidence=1/3 in C57BL/6 mice, usually arise from the ventral prostate (VP) lobes, smallest of all lobes. The weight of genito-urinary (GU) track (bladder, seminal vesicles, prostate lobes) is conventionally used as a measure of tumor load. Weight of DLP lobes is more specific for epithelial lesion expansion.

Research Design and Safety Monitoring

The detailed experimental design is listed in FIG. 33. The experimental protocols are included below. Specifically, AIN 93M purified powdered diet was supplemented with 0.4% of KAVA extract fraction B (see, Example 1 and the Figures). Fresh diet was prepared once a week, made into moist cookies and air dried and stored at 4 degrees C. Cookies were weighed in and out for estimating food intake by food dis-appearance data. Fresh diet provided twice a week. Food intake=approximately 3 g/mouse daily. Mice health was monitored 2-3 times initially; however, this was done more frequently when the mice were over 16 wks. Mice body weight was measured once a week initially; then bi-weekly.

Results and Conclusions

As shown in FIGS. 9-12 and FIGS. 34-35, feeding 0.4% Kava extract Fraction B from 8 weeks of age (early PIN lesions) in TRAMP mice significantly decreased genitourinary tract weight and prostate weight at 16 and 28 weeks of age, respectively. Such dietary treatment decreased incidence of NE-carcinomas at 28 weeks from 50% to 14.3% ($X^2$ test, p<0.05). Kava Fraction B inhibited both epithelial lesion lineage and NE-carcinogenesis lineage.

Example 3

Effect of Dihydromethysticin and Kava Fraction B on Lung Cancer Treatment in the Xenograft Models Introduction of the Models Cancer xenograft models inoculated using human cancer cell lines have been well-accepted as the animal model to evaluate and develop cancer therapeutic agents. Human H2009 and A549 lung cancer cell lines are two general cancer cell lines for establishing xenograft models. In this example, kava and its modalities, including Fractions A, B, C, dihydromethysticin, and methysticin, have been evaluated for their potential to suppress tumor growth, which support the potential use of these compounds/compositions as therapeutic agents for the treatment of human cancers (see, Example 1 for a description of Fractions A, B and C).

Research Design and Safety Monitoring

Typically human origin lung cancer cells were cultured and mixed with Metrigel. $2-5 \times 10^6$ cells were inoculated in the nude mice. Mice were randomized into different groups when the tumor size reached ~50 mm$^3$. Treated mice received drug candidate at a dose of 40 mg/kg bodyweight via i.p. injection or oral gavage. The tumor size was monitored once or twice a week until 5 weeks since the treatment or when the size of the tumors >1000 mm$^3$. Mouse bodyweight was monitored once a week. Mice were CO$^2$ euthanized and the tumors were collected and weighed. Major organs were grossly examined and weighed as well.

Results and Conclusion

Figure 13:
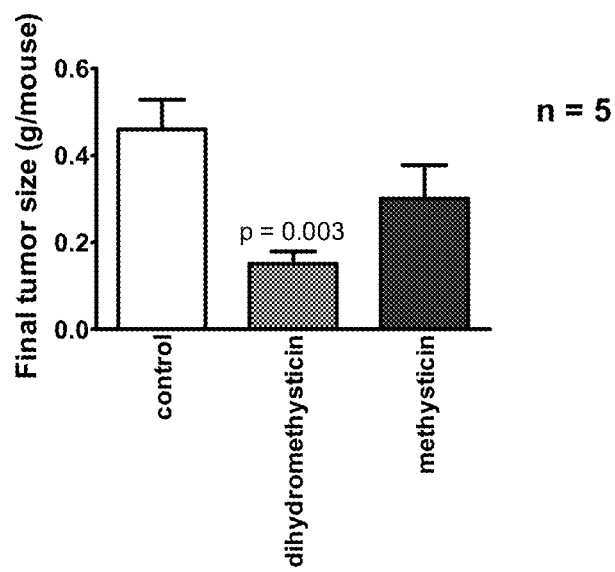
FIG. 13. The effect of dihydromethysticin and methysticin on reducing tumor volume of lung tumors inoculated by human lung H2009 cancer cell lines.
Figure 14A:
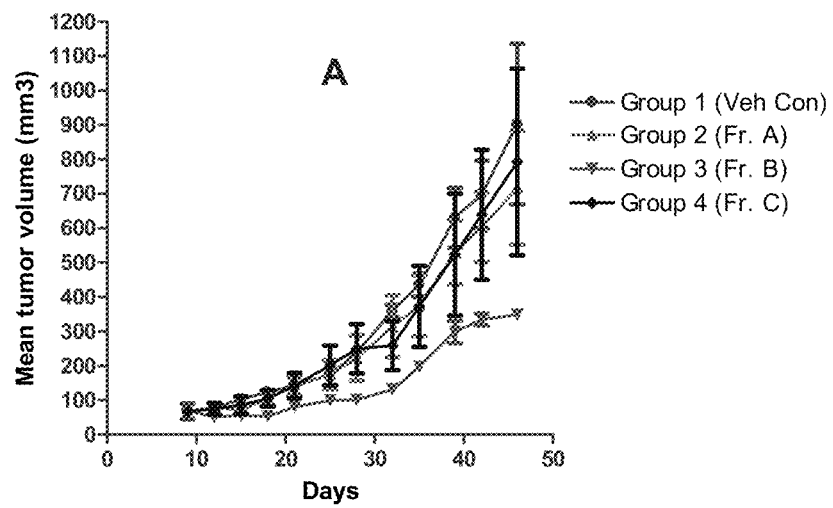
FIGS. 14A-14B. The effect of Fractions A, B, and C on reducing tumor volume of lung tumors inoculated by human lung A549 cancer cell lines. In the bottom panel (FIG. 14B), the bars represent the following, from left to right: Vehicle Control, Kava Fraction A, Kava Fraction B and Kava Fraction C.
Figure 14B:
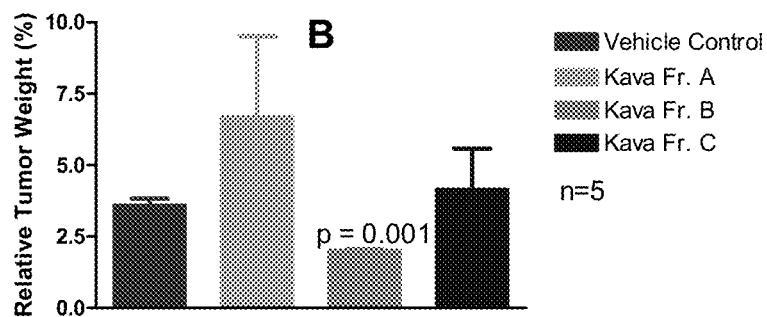
Figure 15:
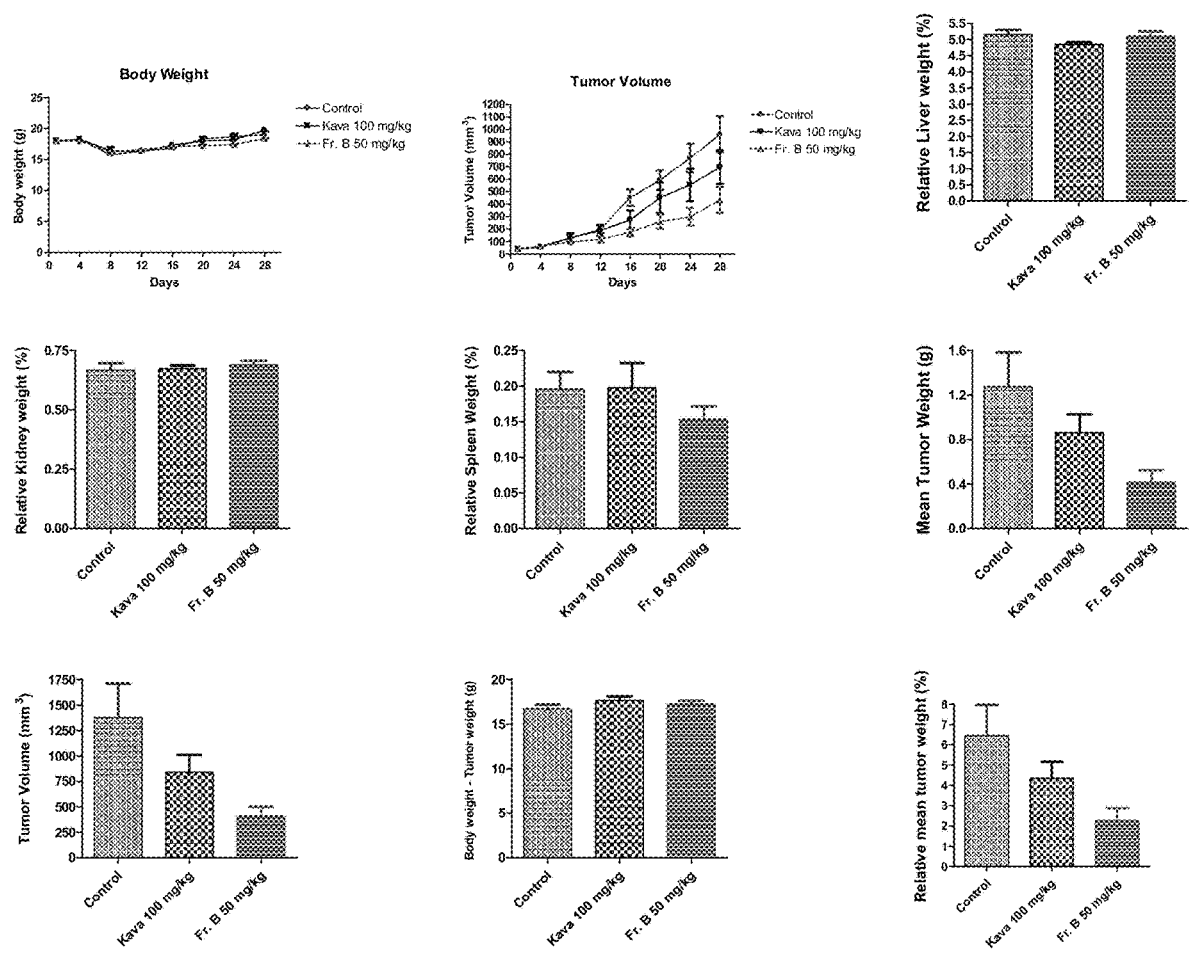
FIG. 15. The effect of kava and Fraction B on reducing tumor volume of lung tumors inoculated by human lung A549 cancer cell lines and safety.

As shown in FIG. 13, dihydromethysticin treatment significantly reduced the tumor volume induced by H2009 human lung cancer cell lines relative to control group, suggesting that dihydromethysticin is a promising anticancer agent. Similarly as shown in FIGS. 14A-14B and 15, Fraction B, which contains dihydromethysticin also significantly reduced the tumor volume induced by A549 human cancer cell line relative to control groups, suggesting that Fraction and likely dihydromethysticin are likely anticancer agents against different malignancies.

Example 4

Dihydromethysticin (DHM) from Kava Blocks Tobacco Carcinogen 4-(methylnitrosamino)-1-(3-pyridyl)-1-butanone (NNK)-Induced Lung Tumorigenesis and Differentially Reduces DNA Damage in A/J Mice Abstract As discussed herein, kava and its flavokavain-free Fraction B completely blocked 4-(methylnitrosamino)-1-(3-pyridyl)-1-butanone (NNK)-induced lung tumorigenesis in A/J mice with a preferential reduction in NNK-induced O$^6$-methylguanine (O$^6$-mG). In this study, natural (+)-dihydromethysticin (DHM) was identified as a lead compound through evaluating the in vivo efficacy of five major compounds in Fraction B on reducing O$^6$-mG in lung tissues. (+)-DHM demonstrated outstanding chemopreventive activity against NNK-induced lung tumorigenesis in A/J mice with 97% reduction of adenoma multiplicity at a dose of 0.05 mg/g of diet (50 ppm). Synthetic (±)-DHM was equally and possibly more effective as the natural (+)-DHM in these bioassays while a structurally similar analog, (+)-dihydrokavain (DHK), was completely inactive, revealing a sharp in vivo structure-activity relationship (SAR). Analyses of an expanded panel of NNK-induced DNA adducts revealed that DHM reduced a subset of DNA adducts in lung tissues derived from 4-(methylnitrosamino)-1-(3-pyridyl)-1-butanol (NNAL, the active metabolite of NNK). Preliminary 17-week safety studies of DHM in A/J mice at a dose of 0.5 mg/g of diet (at least 10× its minimum effective dose) revealed no adverse effects, suggesting that DHM is likely free of kava's hepatotoxic risk. These results demonstrate the outstanding efficacy and promising safety margin of DHM in preventing NNK-induced lung tumorigenesis in A/J mice, with a unique mechanism of action and high target specificity.

Introduction

Lung cancer causes ~160,000 deaths in the U.S. and 1.4 million deaths worldwide annually. Due to the limited success in treatment (Cohen, V et al. (2004) *Curr. Opin. Pulm. Med.* 10: 279-283), prevention is of paramount importance. Tobacco cessation would, without a doubt, be the ideal strategy and should be highly promoted since cigarette smoking causes 90% of lung cancers. Quitting, however, is very challenging because of the addictive nature of nicotine in tobacco products; many smokers will not succeed even after multiple attempts and with the best cessation support. These individuals contribute significantly to the estimated 200,000 lung cancer incidence in the U.S. each year in association with an estimated annual medical cost of $12 billion. Chemopreventive agents hence need to be developed for these high-risk populations, besides further optimizing tobacco cessation methods. During the past few decades, a number of compounds have been identified as potential lung cancer chemopreventive agents and several of them have been evaluated in the clinic, but unfortunately with no success (Hecht, S S et al. (2009) *Nat. Rev. Cancer.* 9: 476-488). The lack of clinical effectiveness is at least partly due to the moderate in vivo efficacy of some of the leads. Novel entities with superior efficacy and unique mechanisms, therefore, need to be developed.

4-(Methylnitrosamino)-1-(3-pyridyl)-1-butanone (NNK) is a tobacco-specific and highly potent pulmonary carcinogen, selectively inducing lung adenoma and adenocarcinoma in various species (Hecht, S S. (1998) *Chem. Res. Toxicol.* 11: 559-603). Substantial evidence also suggests that NNK in cigarette smoke contributes to pulmonary adenocarcinoma in the U.S. smokers. The incidence of lung adenocarcinoma has increased in the U.S. during the past few decades. Such a change has been observed only among smokers, suggesting its association with cigarette related factors. One study noted an increase in NNK levels in the mainstream smoke of a leading U.S. non-filter cigarette between 1978 and 1992 while levels of benzo[α]pyrene (BaP), another well-characterized pulmonary carcinogen, decreased in the same cigarette from 1959-1992 (Hoffmann, D et al. (1993) *Journal of Smoking-related disorders.* 4: 165-189). Further evidence supporting a role for NNK in human lung adenocarcinoma derives from the comparison of NNK content in cigarette smoke and adenocarcinoma rates among the U.S., UK, Canada and Australia (Burns, D M et al. (2011) *Cancer Causes Control.* 22: 13-22).

Figure 16:
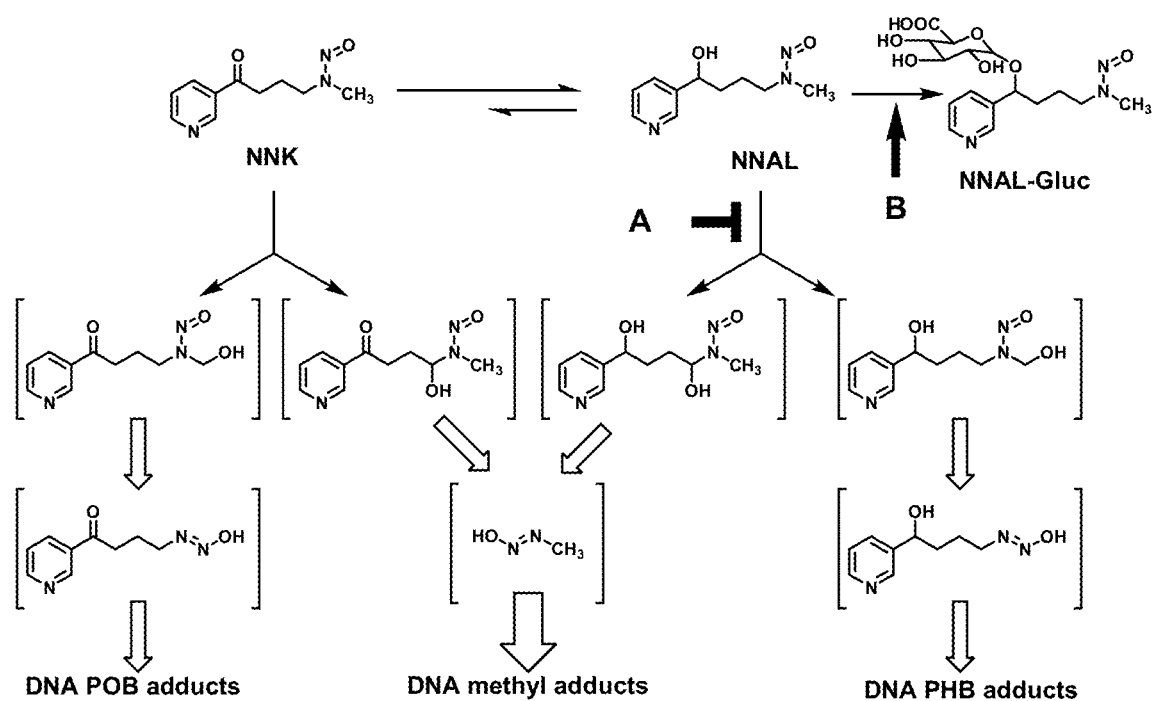
FIG. 16. Metabolic pathways of NNK leading to formation of DNA adducts and hypothetic points of action by DHM for its selective reduction in a subset of NNK-induced DNA damage in A/J mouse lung—preferential inhibition of NNAL activation via hydroxylation (A) or enhancing detoxification of NNAL via glucuronidation (B).

Mechanistically NNK is metabolically activated via α-hydroxylation to generate two reactive species, leading to two types of DNA modifications—methylation and pyridyloxobutylation (Hecht, S S. (2012) *Int. J. Cancer.* 131: 2724-2732; Hecht, S S. (2008) *Chem. Res. Toxicol.* 21: 160-171) (FIG. 16). The extent of DNA damage can be characterized by quantifying different DNA adducts—$O^6$-methylguanine ($O^6$-mG) and 7-methyl guanine (7-mG) for methylation and 7-[4-(3-pyridyl)-4-oxobut-1-yl]guanine (7-pobG), $O^6$-[4-(3-pyridyl)-4-oxobut-1-yl]-2'-deoxyguanosine ($O^6$-pobdG) and $O^2$-[4-(3-pyridyl)-4-oxobut-1-yl]thymidine ($O^2$-pobdT) for pyridyloxobutylation. NNK is also metabolically converted to 4-(methylnitrosamino)-1-(3-pyridyl)-1-butanol (NNAL) (FIG. 16). NNAL can be activated via α-hydroxylation as well to generate two reactive species, resulting in two types of DNA modifications—methylation and pyridylhydroxybutylation. The extent of pyridylhydroxybutylation can be characterized by quantifying 7-[4-(3-pyridyl)-4-hydroxobut-1-yl]guanine (7-phbG), $O^6$-[4-(3-pyridyl)-4-hydroxobut-1-yl]-2'-deoxyguanosine ($O^6$-phbdG) and $O^2$-[4-(3-pyridyl)-4-hydroxobut-1-yl]thymidine ($O^2$-phbdT). DNA damage by NNK and NNAL has been well established as one major underlying mechanism for NNK-induced lung tumorigenesis (Hecht, S S. (1998) *Chem. Res. Toxicol.* 11: 559-603). Reducing such DNA damage is, therefore, a plausible strategy for chemoprevention of lung cancer.

The A/J mouse NNK-induced lung tumorigenesis model has been widely used in evaluating lung cancer chemopreventive agents (Hecht, S S et al. (2009) *Nat. Rev. Cancer.* 9: 476-488) because A/J mice are prone to lung tumorigenesis (O'Donnell, E P et al. (2006) *Cancer Lett.* 241: 197-202) and the tumors have similar morphological, histological and molecular features as human lung adenocarcinomas (Malkinson, A M. (2001) *Lung Cancer.* 32: 265-279). With NNK treatment, A/J mice develop lung tumors with a 100% incidence and a high multiplicity (Hecht, S S et al. (2009) *Nat. Rev. Cancer.* 9: 476-488; Malkinson, A M. (2001) *Lung Cancer.* 32: 265-279). Among NNK-induced DNA adducts, the quantity of $O^6$-mG has shown a strong positive correlation with lung tumor multiplicity (Peterson, L A et al. (1991) *Cancer Res.* 51: 5557-5564) and A/J mice with an increased DNA repair capacity specific to $O^6$-mG are less susceptible to NNK-induced lung tumorigenesis (Liu, L et al. (1999) *Carcinogenesis.* 20: 279-284). In combination with the high miscoding property of $O^6$-mG (19-22), NNK-induced $O^6$-mG is believed essential to initiate lung tumorigenesis in A/J mice.

As described herein, a commercial kava product efficiently blocks NNK-induced lung tumorigenesis in A/J mice at a dose of 1.25 mg/g of diet (Leitzman, P et al. (2014) *Cancer. Prev. Res.,* 7: 86-96). Fraction B of this product, containing mostly kavalactones (FIG. 17A), fully recapitulates its chemopreventive efficacy. Kava and Fraction B reduces NNK-induced DNA damage in the lung with a preference in $O^6$-mG adduct over the POB adducts while ineffective fractions have no effect on $O^6$-mG (Leitzman, P et al. (2014) *Cancer. Prev. Res.,* 7: 86-96). Monitoring the impact of single chemicals in Fraction B on $O^6$-mG, therefore, would be an economic strategy to identify the active lead(s). It is also mechanistically intriguing regarding the preferential reduction in $O^6$-mG adduct.

Thus, described herein is the identification and confirmation of dihydromethysticin (DHM) as the active compound. DHM potently and efficiently blocks NNK-induced lung tumorigenesis in A/J mice. As described below, the mechanism leading to its differential reduction in NNK-induced DNA damage has also been investigated and preliminary long-term safety of DHM in A/J mice upon high-dose exposure is provided.

Abbreviations

DHM, dihydromethysticin; DHK, dihydrokavain; NNK, 4-(methylnitrosamino)-1-(3-pyridyl)-1-butanone; NNAL, 4-(methylnitrosamino)-1-(3-pyridyl)-1-butanol; BaP, benzo[α]pyrene; $O^6$-mG, $O^6$-methylguanine; 7-mG, 7-methylguanine; 7-pobG, 7-[4-(3-pyridyl)-4-oxobut-1-yl]guanine; $O^6$-pobdG, $O^6$-[4-(3-pyridyl)-4-oxobut-1-yl]-2'-deoxyguanosine; $O^2$-pobdT, $O^2$-[4-(3-pyridyl)-4-oxobut-1-yl]thymidine; 7-phbG, 7-[4-(3-pyridyl)-4-hydroxobut-1-yl]guanine; $O^6$-phbdG, $O^6$-[4-(3-pyridyl)-4-hydroxobut-1-yl]-2'-deoxyguanosine; $O^2$-phbdT, $O^2$-[4-(3-pyridyl)-4-hydroxobut-1-yl]thymidine; AGT, $O^6$-alkylguanine-DNA alkyltransferase; ANOVA, analysis of variance; ALP, alkaline phosphatase; ALT, alanine aminotransferase; AST, aspartate aminotransferase; BUN, blood urea nitrogen; CK, creatine kinase; H&E, hematoxylin and eosin; MTD, maximum tolerated dose; PEITC, phenethyl isothiocyanate; I3C, indole-3-carbinol.

Materials and Methods
Chemicals, Reagents and Animal Diets

NNK was prepared by following a reported procedure (Hecht, S S et al. (1983) *Carcinogenesis.* 4: 305-310). [$CD_3$]$O^6$-mG was purchased from Toronto Research Chemicals (Toronto, Ontario, Canada). [$^{13}CD_3$]7-methylguanine was prepared by following a reported procedure (Peterson, L A et al. (2013) *Chem. Res. Toxicol.* 26: 1464-1473). 7-PobG, $O^6$-pobdG, $O^2$-pobdT, 7-phbG, $O^6$-phbdG, $O^2$-phbdT and the corresponding [pyridine-$D_4$] analogues were synthesized by following reported procedures (Lao, Y et al. (2006) *Res. Toxicol.* 19: 674-682; Sturla, S J et al. (2005) *Chem. Res. Toxicol.* 18: 1048-1055; Upadhyaya, P et al. (2008) *Chem. Res. Toxicol.* 21: 1468-1476). Micrococcal nuclease and phosphodiesterase II were purchased from Worthington Biochemical Corporation (Lakewood, N.J.). Alkaline phosphatase was purchased from Roche Molecular Biochemicals (Indianapolis, Ind.).

Kava was acquired from Gaia Herbs, Inc. (Brevard, N.C.) as an ethanol extract of the wild crafted lateral root from Vanuatu. It was standardized to 150 mg/mL total kavalactones. The AIN-93 G and M powdered diets were purchased from Harlan Teklad (Madison, Wis.). For the short-term DNA damage study, the AIN-93 G diet was used during the experimental period. For the long-term lung tumorigenesis study, the AIN-93 G diet started one week before the first dose of NNK and ended one week after the second dose of NNK. The AIN-93 M diet was used during the rest of the experimental period.

Isolation of Chemicals in Fraction B

Figures 17A, 17B:
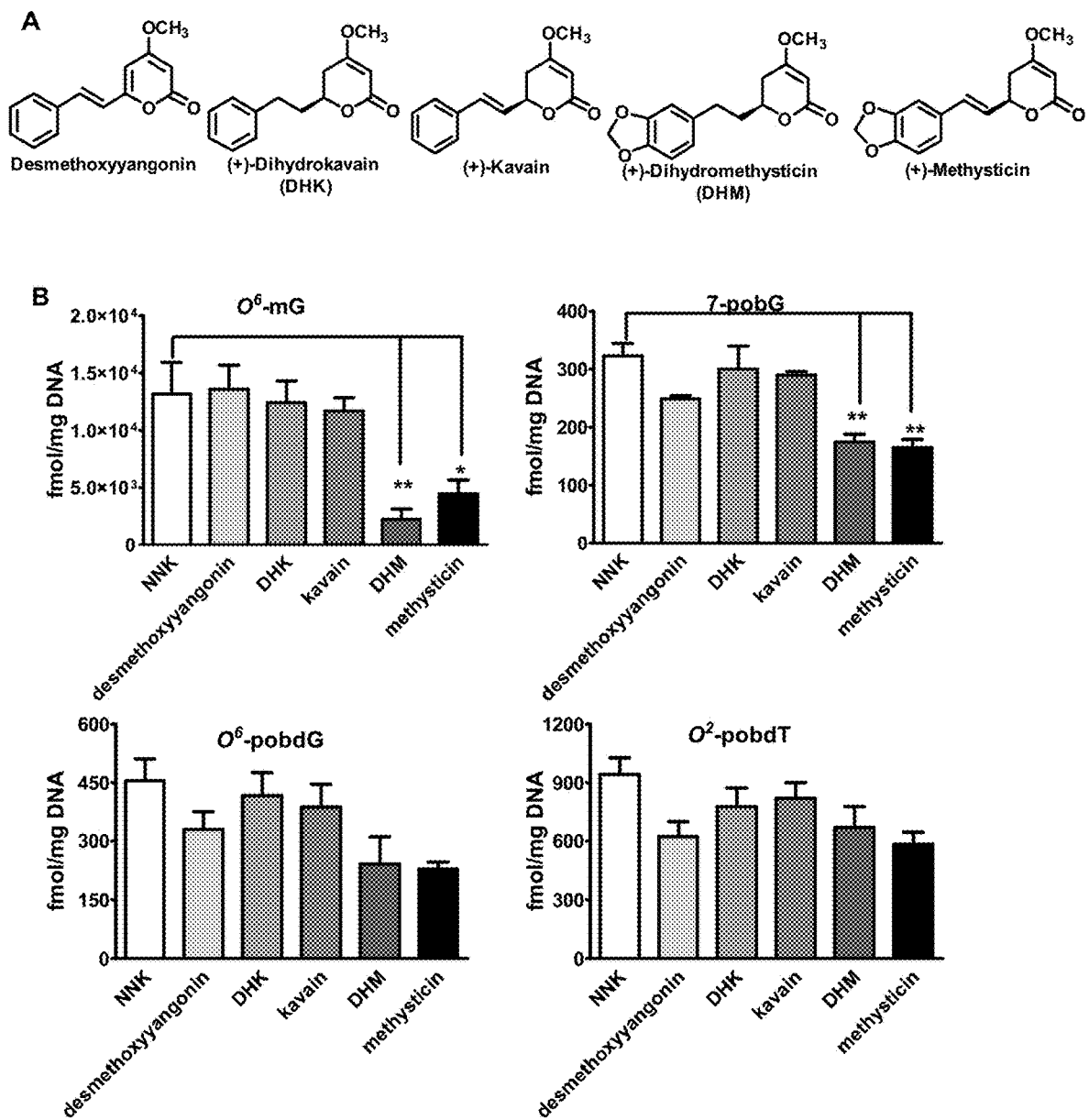
FIGS. 17A-17B. Characterization of natural kavalactones on NNK-induced DNA damage in A/J mouse lung tissues.

Five kavalactones (desmethoxyyangonin, (+)-dihydrokavain (DHK), (+)-kavain, (+)-DHM, and (+)-methysticin, FIG. 17A) were isolated from Fraction B by normal phase silica gel chromatography with a gradient mixture of hexane and ethyl acetate as the eluent. Their chemical structures were characterized by $^1$H-NMR and mass spectrometry. Their purities were estimated >90% by HPLC on a Beckman Coulter System Gold 126 solvent module with a 168 detector. A Clipeus C-18 column (5 μm, 250×4.6 mm) was used for the analyses. The flow rate was 1 mL/min. The mobile phase A was 10 mM $NH_4OAc$ aqueous solution and B was acetonitrile. The time program used for the analyses was 50% B for 15 min.

Synthesis of (±)-DHM (±)-DHM was synthesized by following a procedure similar as previously reported (Shaik, A A, Tan, J., Lu, J., Xing, C. (2012) *ARKIVOC*. viii: 137-145). Its structure and purity were characterized by $^1$H-NMR, mass spectrometry and HPLC by following the conditions detailed above.

Diet Preparation

Kava was reconstituted in absolute ethanol (50 mL) and then mixed with the AIN-93 diet (150 g). Similarly, absolute ethanol (50 mL each) reconstituted with kavalactones was mixed with the AIN-93 diet (150 g each) for the kavalactone diets. Absolute ethanol (50 mL) was mixed with the AIN-93 diet (150 g) for the control diet. The reconstituted diets were dried under vacuum to remove ethanol and then ground into fine powders. All diets were mixed with additional AIN-93 diet to the desired dose.

General Protocols for Animal Studies

Female A/J mice (5-6 weeks of age) were purchased from the Jackson Laboratory (Bar Harbor, Me.) and handled according to IACUC-approved animal welfare protocols at the University of Minnesota. Upon arrival, the mice were housed in the specific pathogen-free animal facilities of the Research Animal Resources at the University of Minnesota.

General Protocols for Isolating DNA from Lung and Liver Tissues

DNA was isolated and purified from ~100 mg lung and liver tissues of each mouse, following Genomic-tip 100/G protocol from Qiagen Corp (Valencia, Calif.).

Assessing the Effect of Five Natural Kavalactones in Fraction B on NNK-Induced $O^6$-mG and Three POB Adducts in A/J Mouse Lung Tissues After one-week acclimation, A/J mice were weighed and randomized into seven groups (3 mice per group) and switched to the AIN-93 G diet on a date defined as Day 1. Mice in Groups 1 and 2 were given the AIN-93 G diet during Day 1-Day 7. Mice in Groups 3-7 were given the AIN-93 G diet supplemented with desmethoxyyangonin, (+)-DHK, (+)-kavain, (+)-DHM, or (+)-methysticin respectively, at a dose of 1 mg/g of diet during Day 1-Day 7. Mice in Groups 2-7 were given a single dose of NNK at 100 mg/kg bodyweight in saline (0.1 ml) via intraperitoneal (i.p.) injection at the beginning of Day 7 while mice in Group 1 were given saline (0.1 ml). Mice were euthanized by $CO_2$ overdosing 24 h after NNK treatment, and lung tissues were collected and stored at −80° C. until DNA isolation. A number of NNK-induced DNA modifications ($O^6$-mG, 7-pobG, $O^6$-pobdG and $O^2$-pobdT) were quantified by following a reported procedure (Leitzman, P et al. (2014) *Cancer. Prev. Res.,* 7: 86-96).

Evaluating the Dose-Response Effect of Kava, (+)-DHM Vs. (+)-DHK and Synthetic (±)-DHM on NNK-Induced DNA Adducts in A/J Mouse Lung and Liver Tissues After one-week acclimation, A/J mice were weighed and randomized into ten groups (3 mice per group except for Group 1 that had one mouse as the negative control) and switched to the AIN-93 G diet on a date defined as Day 1. Mice in Groups 1 and 2 were given the AIN-93 G diet during Day 1-Day 7. Mice in Groups 3-10 were given the AIN-93 G diets supplemented with kava, (+)-DHK, (+)-DHM, and synthetic (±)-DHM respectively at the specified dose during Day 1-Day 7. Mice in Groups 2-10 were given a single dose of NNK at 100 mg/kg bodyweight in saline (0.1 ml) via i.p. injection at the beginning of Day 7 while the mouse in Group 1 was given saline (0.1 ml). Mice were euthanized by $CO_2$ overdosing 24 h after NNK treatment, and lung and liver tissues were collected and stored at −80° C. until DNA isolation. A set of NNK-induced DNA adducts ($O^6$-mG, 7-mG, 7-pobG, $O^6$-pobdG, $O^2$-pobdT, 7-phbG, $O^6$-phbdG and $O^2$-phbdT) were quantified by following reported procedures (Leitzman, P et al. (2014) *Cancer. Prev. Res.,* 7: 86-96; Peterson, L A et al. (2013) *Chem. Res. Toxicol.* 26: 1464-1473; Upadhyaya, P et al. (2008) *Chem. Res. Toxicol.* 21: 1468-1476). For 7-mG isolation, DNA (30 μg) was dissolved in 10 mM sodium phosphate buffer, pH 7 (500 μL) and spiked with [$^{13}C_1{}^2H_3$]7-mG (10 pmol). Samples were heated to 80° C. for 30 minutes. An aliquot (100 μL) was removed for 7-mG analysis.

Assessing the Efficacy of (+)-DHM Vs. (+)-DHK and Synthetic (±)-DHM Against NNK-Induced Lung Adenoma Formation in A/J Mice After one-week acclimation, mice were weighed, randomized into eight groups and switched to the AIN-93 G diet on a date defined as Day 1. The number of mice in each group is specified in the Results Section (FIG. 36). Mice were fed diets supplemented with different compounds at the dose specified in the Results Section during Day 1-Day 14. On Day 7 and Day 14, mice in the negative control group received 0.1 mL of saline solution while mice in the other groups received NNK (100 and 67 mg/kg, respectively, in 0.1 mL of saline solution) via i.p. injection. At the end of Day 21, mice were switched to the AIN-93 M diet until the end of the study. The diet was replenished twice weekly. The diet consumption was measured twice weekly and the body-weight was monitored weekly. This study was terminated at the end of Day 119. All mice were euthanized with $CO_2$ overdosing. The lungs were collected and tumors on the surface of the lungs were counted under blinded conditions by an A.C.V.P board certified pathologist (M.G. O'S.).

Assessing A/J Mouse Safety Upon 17-Week Continuous Exposure of (+)-DHM at a Dose of 0.5 mg/g of Diet After one-week acclimation, A/J mice were weighed and randomized into two groups (five mice in the control group and ten mice in (+)-DHM treatment group). Mice in the control group were maintained on the AIN-93 G diet for three weeks and then switched to the AIN-93 M diet until the end of Week 17. Mice in (+)-DHM treatment group were maintained on the same diet as the control group with supplementation of (+)-DHM at a dose of 0.5 mg/g of diet. Food was replenished twice weekly. Food intake was monitored twice a week and mouse bodyweight was monitored once a week. At the end of Week 8, serum samples from each mouse were prepared from blood collected via a facial vein and analyzed for a panel of clinical chemistry analytes. At the end of Week 17, mice were euthanized by $CO_2$ overdosing. Blood was collected with one portion analyzed for hematology and the other portion processed for serum and analyzed for a full panel of clinical chemistry analytes. Individual animal body weights and major organ weights (lung, liver, heart, spleen and kidney) were recorded. Lung, liver, heart, spleen, kidney and pancreas were fixed in 10% neutral-buffered formalin solution. Appropriately fixed tissues were processed into paraffin blocks using standard histological techniques, and 5µ sections were cut and stained with hematoxylin and eosin (H&E). Histological slides were examined using light microscopy by an experienced A.C.V.P board certified pathologist (M.G. O'S.).

Statistical Analyses

Data on lung adenoma multiplicity were reported as mean±SD (n=5-9). One-way analysis of variance (ANOVA) was used to compare means among the NNK and NNK/treatment groups. Dunnett's test was used for comparisons of the number of tumors between the NNK control and treatment groups when the one-way ANOVA analysis was statistically significant. p-value≤0.05 was considered statistically significant. For DNA damage studies, one-way ANOVA was used to compare means±SD (n=3). Dunnett's test was used for comparisons between the NNK control and treatment groups when one-way ANOVA analysis was statistically significant. p-value≤0.05 was considered statistically significant. For the safety study, an unpaired Student t-test was used for comparison between the control and (+)-DHM treatment groups. A two-tailed p-value≤0.05 was considered statistically significant. All analyses were conducted using GraphPad Prism 4 from GraphPad Software, Inc. (La Jolla, Calif.).

Results

The Effects of Five Kavalactones in Fraction B on NNK-Induced $O^6$-mG, 7-pobG, $O^6$-pobdG and $O^2$-pobdT in A/J Mouse Lung Tissues As previous data described herein showed that the reduction of $O^6$-mG reduction in lung tissues by different kava entities correlated positively with their lung tumor prevention efficacy and Fraction B recapitulated kava's chemopreventive effect on NNK-induced lung tumorigenesis in A/J mice (Leitzman, P et al. (2014) Cancer. Prev. Res., 7: 86-96), this experiment was designed to identify the key compound(s) in Fraction B that reduced NNK-induced $O^6$-mG, which may be the active chemopreventive agent.

Five known kavalactones have been isolated from Fraction B as its major components (FIG. 17A), accounting for 93% of its mass balance (Leitzman, P et al. (2014) Cancer. Prev. Res., 7: 86-96). These five compounds were investigated for their effect on NNK-induced DNA damage in lung tissues, including $O^6$-mG and three POB adducts (7-pobG, $O^6$-pobdG and $O^2$-pobdT) (FIG. 17B). Two compounds, (+)-DHM and (+)-methysticin, significantly reduced NNK-induced $O^6$-mG while the other compounds did not, suggesting (+)-DHM and (+)-methysticin as the potential active compounds and the importance of the 1,3-dioxol functional group. All five compounds had much weaker reduction in the POB adducts (FIG. 17B), consistent with that of Fraction B (Leitzman, P et al. (2014) Cancer. Prev. Res., 7: 86-96). Although not statistically significant, the extent of $O^6$-mG reduction by (+)-DHM was greater than that by (+)-methysticin. (+)-DHM was therefore selected as the lead for further investigation with DHK as a negative control because of its higher structural similarity to (+)-DHM relative to desmethoxyyangonin and (+)-kavain.

The Dose-Response Effect of (+)-DHM on an Expanded Panel of NNK-Induced DNA Damage in Comparison to Kava, (+)-DHK and Synthetic (±)-DHM in A/J Mouse Lung Tissues This study was designed to address three questions. First, what would be the dose of (+)-DHM to induce a similar extent of $O^6$-mG reduction as kava did at a dose of 1.25 mg/g of diet, which effectively blocked NNK-induced lung tumor formation (Leitzman, P et al. (2014) Cancer. Prev. Res., 7: 86-96)? Kava was evaluated at two dosages—5 and 1.25 mg/g of diet respectively while (+)-DHM was evaluated at four dosages—1, 0.25, 0.1 and 0.01 mg/g of diet with (+)-DHK evaluated at a dose of 1 mg/g of diet as a control. Secondly, given that the isolated (+)-DHM contained impurities, how can the impurity be ruled out as the active compound? Synthetic (±)-DHM therefore was prepared and evaluated at a dose of 1 mg/g of diet. Lastly, what is the mechanism leading to (+)-DHM's preferential reduction in $O^6$-mG over POB adducts in lung tissues? Based on the molecular bases of NNK metabolism and DNA damage (FIG. 16) (Hecht, S S. (1998) Chem. Res. Toxicol. 11: 559-603), four possible mechanisms were identified: 1) preferential inhibition of NNK methylene hydroxylation over its methyl hydroxylation; 2) an increased $O^6$-alkylguanine-DNA alkyltransferase (AGT)-mediated $O^6$-mG repair (Belinsky, S A et al. (1988) Carcinogenesis. 9: 2053-2058; Peterson, L A et al. (1993) Cancer Res. 53: 2780-2785); 3) preferential inhibition of NNAL hydroxylation over NNK hydroxylation; or 4) increased detoxification of NNAL. These mechanisms could be differentiated by characterizing the effect of DHM on an expanded panel of DNA adducts, including POB DNA adducts (7-pobG, $O^6$-pobdG and $O^2$-pobdT), PHB DNA adducts (7-phbG, $O^6$-phbdG and $O^2$-phbdT) and methyl DNA adducts ($O^6$-mG and 7-mG).

Figures 18A, 18B, 18C:
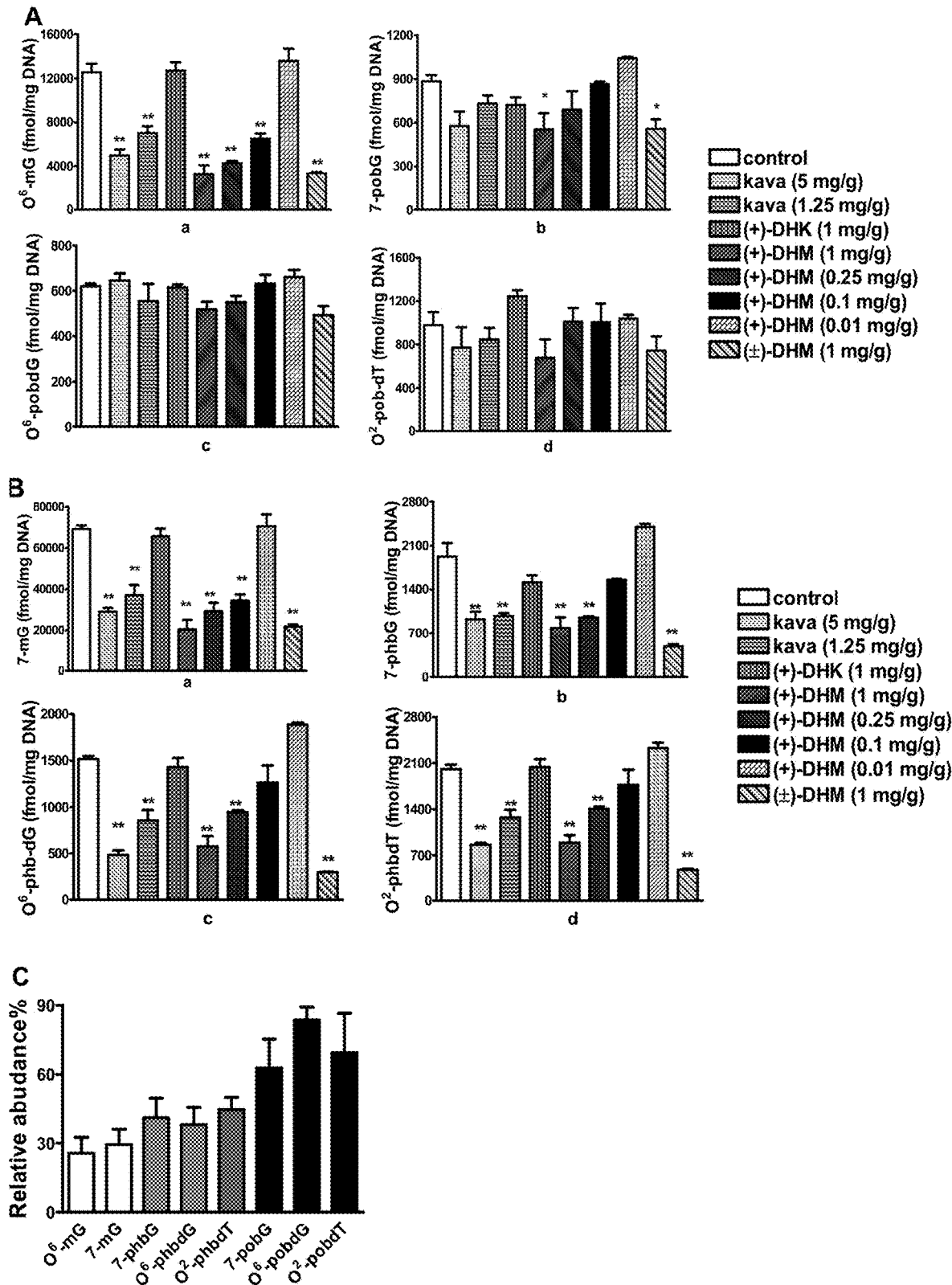
FIGS. 18A-18C. Characterization of the effect of different agents on NNK-induced DNA damage in A/J mouse lung tissues.

Consistent with previous results, kava preferentially and dose-dependently reduced $O^6$-mG in lung tissues (FIG. 18A.a) while it had minimal effects on POB adducts (FIG. 18A.b-d). (+)-DHM also preferentially and dose-dependently reduced $O^6$-mG (FIG. 18A.a) with weaker effects on POB adducts (FIG. 18A.b-d) whereas (+)-DHK did not reduce any of these adducts even at a dose of 1 mg/g of diet. The extent of reduction in $O^6$-mG by (+)-DHM at a dose of 0.1 mg/g of diet was comparable to that induced by kava at a dose of 1.25 mg/g of diet (FIG. 18A.a). Since (+)-DHM at a dose of 0.01 mg/g of diet had no effect on $O^6$-mG, the minimum chemopreventive dose of DHM would be between 0.01-0.1 mg/g of diet. (+)-DHM also dose-dependently reduced 7-mG (FIG. 18B.a) with the extents of reduction similar to those in $O^6$-mG (FIG. 18A.a). These results indicate that AGT-mediated $O^6$-mG repair is not involved in DHM's DNA damage reduction. Surprisingly, (+)-DHM dose-dependently reduced PHB adducts (FIG. 18B.b-d) in lung tissues as well, again with the extents of reduction similar to those in $O^6$-mG and 7-mG (FIGS. 18A.a and 18B.a). Since (+)-DHM has minimal effect on POB adducts, these results suggest that its reduction in NNK-induced DNA damage is likely mediated through the NNAL pathway, either by inhibiting its activation or enhancing its detoxification (A and B in FIG. 16). The synthetic (±)-DHM at 1 mg/g of diet had similar effects in reducing DNA damage as the natural (+)-DHM (FIGS. 18A and B), confirm DHM as the active compound.

The Lack of Effect of Kava, (+)-DHM, (+)-DHK and Synthetic (±)-DHM on NNK-Induced DNA Damage in A/J Mouse Liver Tissues Since liver is the major metabolizing organ of the body, we also characterized the effect of kava, (+)-DHM, (+)-DHK and (±)-DHM on NNK-induced DNA damage in liver tissues. Surprisingly none of the treatments had significant effects on NNK-induced DNA damage in the liver tissues (data not shown).

The Efficacy of Kava, (+)-DHM, (+)-DHK and Synthetic (±)-DHM on NNK-Induced Lung Adenoma Formation in A/J Mice To validate the chemopreventive potential of DHM, we carried out an NNK-induced lung adenoma assay as shown in FIG. 36. A/J mice without NNK treatment had low adenoma incidence (20%) and low adenoma multiplicity (0.2±0.4 lung adenoma/mouse, Group 1) while NNK-treated A/J mice had 100% adenoma incidence and high adenoma multiplicity (13.9±6.9 lung adenoma/mouse, Group 2). Kava at a dose of 1.25 mg/g of diet slightly reduced adenoma incidence by 20% but significantly reduced adenoma multiplicity by 95.6% (to 0.8±0.4, Group 3). Based on the estimated minimum effective dose of (+)-DHM between 0.01 and 0.1 mg/g of diet, we tested it at 0.5 and 0.05 mg/g of diet (Groups 4 and 5). (+)-DHM at both dosages reduced adenoma incidence by 40% and significantly reduced adenoma multiplicity by 97.1% (to 0.6±0.5, Groups 4 and 5), suggesting that its minimum effective dose has not been reached. All mice were adenoma free upon (±)-DHM treatment at a dose of 0.5 mg/g of diet (Group 8). (+)-DHK, as a negative control, showed no reduction at all at 0.5 or 0.05 mg/g of diet (Groups 6 and 7). Overall, these data established DHM as a lung cancer chemopreventive agent with a minimum effective dose lower than 0.05 mg/g (50 ppm).

Figure 19:
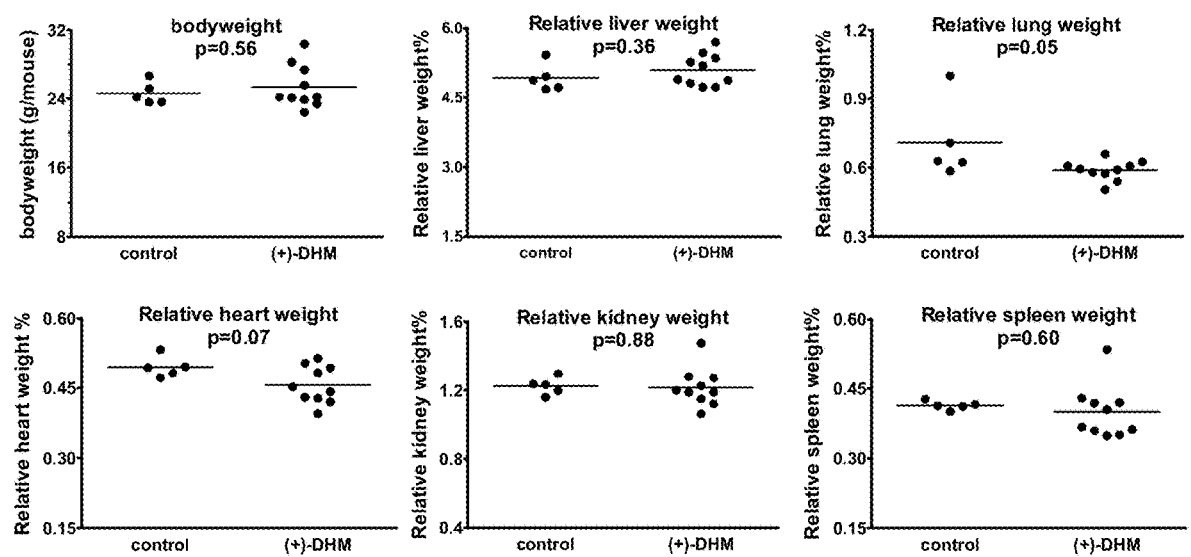
FIG. 19. Bodyweight and major organs from the control mice and mice with (+)-DHM exposure at a dose of 0.5 mg/g of diet at Week 17. p values were given with comparison between the control group (n=5) and (+)-DHM treatment group (n=10) using a two-tailed Student t-test.
Figure 20A:
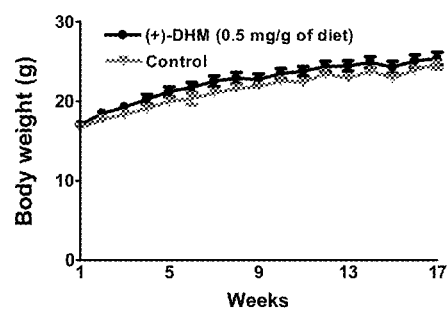
FIGS. 20A-20B. Body weight and food consumption data for A/J mice from control and (+)-DHM (0.5 mg/g of diet) treated group.
Figure 20B:
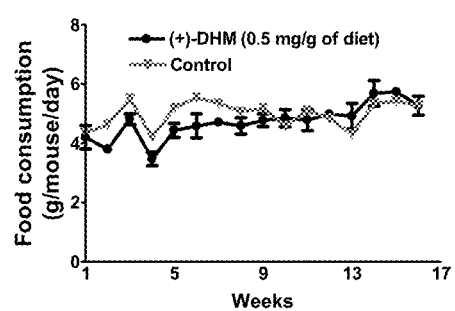
Figures 21A, 21B:
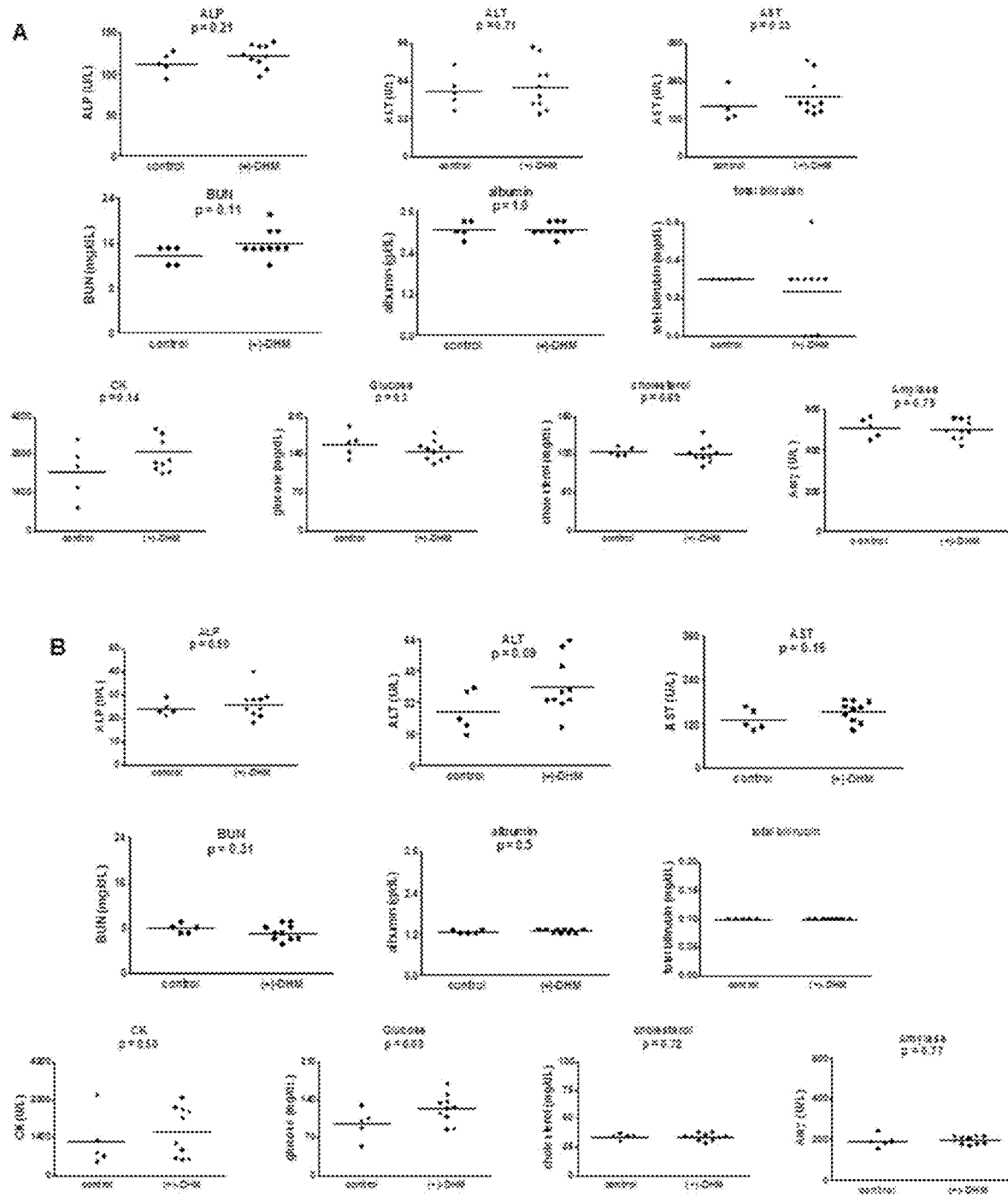
FIGS. 21A-21B. Clinical chemistry results of serum samples from the control mice and mice with (+)-DHM exposure at a dose of 0.5 mg/g of diet.
Figure 22:
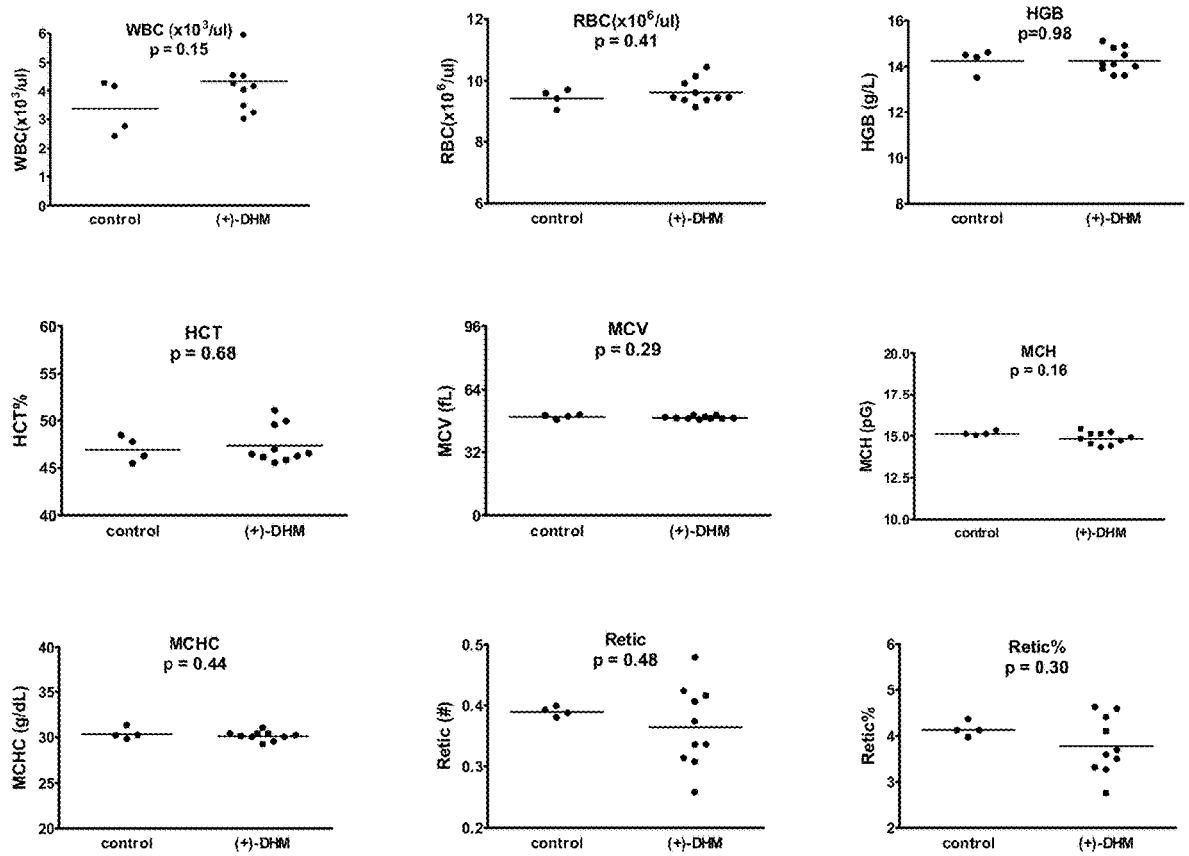
FIG. 22. Hematological results of blood samples from control mice and mice with exposure to (+)-DHM at a dose of 0.5 mg/g of diet for 17 weeks. p values were given when possible with comparison between the control group (n=4) and the treatment group (n=10) using two-tailed Student t-test.
Figure 22:
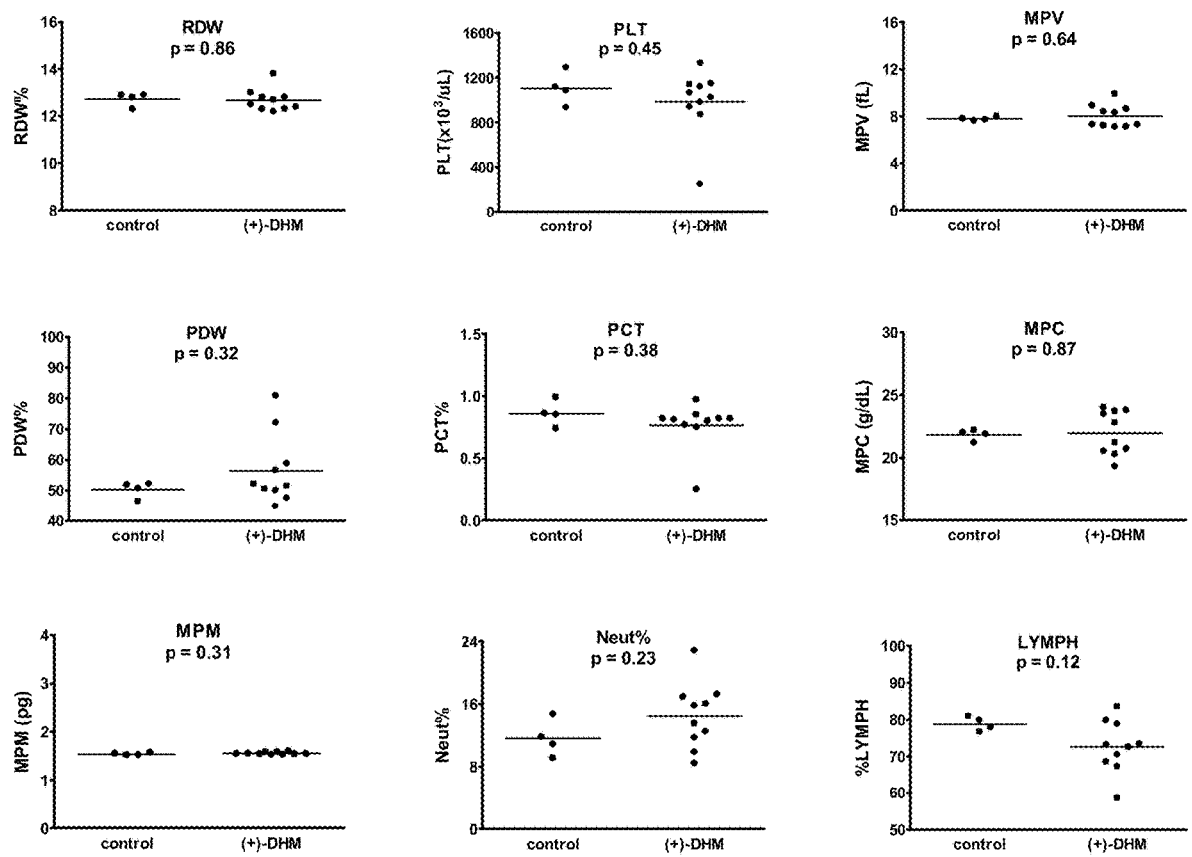
Figure 22:
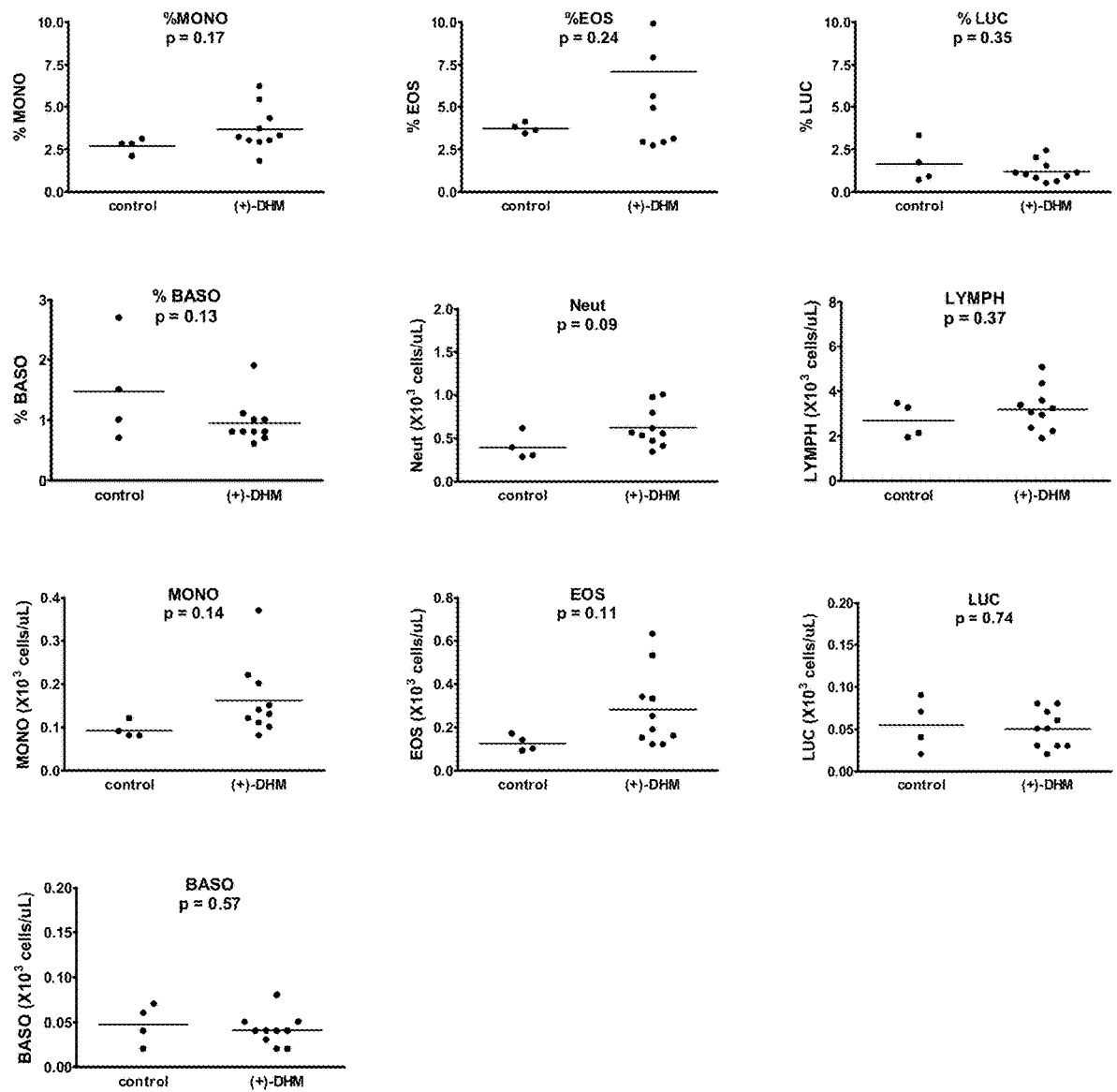

A/J Mouse Safety Assessment Upon 17-Week Continuous Exposure of (+)-DHM at a Dose of 0.5 mg/g of Diet Cognizant of the hepatotoxic concerns associated with kava (Rowe, A et al. (2012) Res. 26: 1768-1770; Teschke, R et al. (2013) *Phytother Res.* 27: 472-474), we characterized a number of parameters to assess the safety of (+)-DHM. Mice with (+)-DHM feeding started with a slightly higher average bodyweight and remained heavier than the control mice through the study, but none of the differences were statistically significant (FIG. 20A). The food intake was similar as well (FIG. 20B). The clinical chemistry results for the serum samples collected at the end of Week 8 are summarized in FIG. 21A, and they included alkaline phosphatase (ALP), alanine aminotransferase (ALT), aspartate aminotransferase (AST), blood urea nitrogen (BUN), albumin, total bilirubin, creatine kinase (CK), glucose, cholesterol and amylase. All of these parameters reflect liver functions, except for amylase (a marker for pancreas). No significant differences were detected in any of these parameters between the control group and the (+)-DHM group. The clinical chemistry results of the serum samples collected at the end of Week 17 are summarized in FIG. 21B. Same as the 8-week outcome, there were no significant differences for any of these parameters between the control group and the (+)-DHM group. The time-course changes of these parameters for each mouse also revealed no obvious difference between the control and (+)-DHM groups (data not shown). On Week 17, the concentration of various salts in the serum was quantified as well; these data were used to calculate serum osmolality and anion gap, which revealed no differences between the control and (+)-DHM groups either (data not shown). The blood samples on Week 17 were also analyzed for full-panel hematology (one blood sample from a control mouse clotted and could not be analyzed, which resulted in four data points for the control group, FIG. 22). None of these parameters were significantly different between the control and (+)-DHM groups. Lastly, the final bodyweight and the relative weights of five organs (FIG. 19) were not significantly different between the control and (+)-DHM groups except for the lung tissues. The average relative lung weight for the control group was significantly higher than that for the (+)-DHM group (p=0.05). An inspection of the data from each mouse revealed that one mouse in the control group had an increased lung weight that was attributed to multifocal hemorrhage within the lung at the time of euthanasia. Excluding this animal, there were no significant differences between the control and (+)-DHM groups (p=0.10). Histopathological examination of liver, lung, heart, kidney, spleen and pancreas tissues revealed no significant differences between the control and (+)-DHM groups (data not shown).

Discussion and Conclusion

The results described herein have unambiguously identified DHM as a potent chemopreventive agent that safely and completely blocks NNK-induced lung tumorigenesis in A/J mice at a dietary intake dose of 0.05 mg/g (50 ppm). (+)-DHM was identified as the lead among five structurally similar compounds based on their efficacy to reduce $O^6$-mG in lung tissues in a short-term assay (FIG. 17B). In a follow-up dose-response experiment using DNA adduct reduction as the readouts, its minimum effective dose was estimated between 0.01-0.1 mg/g of diet (FIG. 18). Therefore (+)-DHM was tested at doses of 0.5 mg/g of diet (500 ppm) and 0.05 mg/g (50 ppm) with a 2-week exposure window during the NNK initiation period only (FIG. 36, Groups 4 and 5). Since (+)-DHM at 0.05 mg/g reduced NNK-induced lung adenoma multiplicity by 97% and was as effective as (+)-DHM at 0.5 mg/g, its minimum effective dose would likely be lower than 0.05 mg/g. An extrapolation of an effective dose of 0.05 mg/g of diet for a mouse of 20 g (daily food intake 3 g) would be equivalent to a human dose of 47 mg/day (based on 75 kg human bodyweight) according to the Body Surface Area Normalization method (Reagan-Shaw, S et al. (2008) FASEB J. 22: 659-661). Thus from the dose aspect, (+)-DHM is highly feasible for human usage. The results of the synthetic (±)-DHM are also informative. First, they confirmed DHM as the active chemopreventive agent. Second, it appeared that the synthetic racemic forms outperformed the natural (+)-DHM in blocking NNK-induced DNA adducts and lung adenoma formation at the tested dose of 1 mg/g and 0.5 mg/g, respectively, although the differences were not statistically significant. It remains to be determined whether the synthetic (−)-DHM may be more efficacious than the natural (+)-DHM in a dose range close to its minimum effective dose.

It is interesting to note that (+)-DHK, a structural analog of (+)-DHM (FIG. 17A), was completely inactive in blocking DNA damage (FIGS. 17 and 18) or lung adenoma formation (FIG. 36). Such a sharp in vivo structure-activity relationship (SAR) between (+)-DHM and (+)-DHK suggests a high target specificity of (+)-DHM. It also highlights the importance of the 1,3-dioxol functional group in (+)-DHM for its efficacy. Such a five-member ring may be critical for (+)-DHM to specifically interact with its molecular target, which remains to be identified, leading to its outstanding chemopreventive efficacy. Alternatively (+)-DHM may be metabolized via the 1,3-dioxol functional group to generate the in vivo active form. Further investigation is needed to differentiate these possibilities.

Mechanistically (+)-DHM dose-dependently reduced $O^6$-mG, 7-mG, 7-phbG, $O^6$-phbdG and $O^2$-phbdT in the lung tissues with similar extents of reduction (FIGS. 18A.a and 18B.a-d) while it had much weaker effect on 7-pobG, $O^6$-pobdG and $O^2$-pobdT (FIG. 18A.b-d). These data suggest that DHM may preferentially block NNAL-mediated DNA damage, possibly via inhibiting NNAL activation (A in FIG. 16) or increasing NNAL detoxification (B in FIG. 16). A closer inspection of the extent of reduction in methyl and PHB adducts reveals a slightly higher reduction in methyl adducts, although the difference was not statistically significant (FIG. 18C showed a representative set of data with (+)-DHM treatment at a dose of 1 mg/g of diet). Since the extent of reduction in POB and PHB adducts are all less than those of the methyl adducts, DHM may preferentially inhibit methylene hydroxylation over methyl hydroxylation of NNK and NNAL as well. The lack of effect of DHM on NNK-induced DNA damage in the liver is intriguing, which may be mediated via a potential DHM abundance difference in lung and liver tissues. Alternatively, lung tissues may contain DHM-interacting biomolecules involved in NNAL activation/detoxification that are absent in liver tissues.

There have been limited reports characterizing multiple DNA adducts upon NNK treatment in A/J mice in both lung and liver tissues. An early study by Morse et al. showed that phenethyl isothiocyanate (PETIC) reduced $O^6$-mG in lung tissues, but other DNA adducts and liver tissues were not analyzed (Morse, M A et al. (1989) Cancer Res. 49: 2894-2897). A later study by Prokopczyk et al. showed that synthetic 1,4-phenylenebis(methylene)selenocyanate, an analog of PEITC, preferentially reduced $O^6$-mG in comparison to 7-mG (Prokopczyk, B et al. (1996) Carcinogenesis. 17: 749-753). Crampsie et al. recently reported that phenylbutyl isoselenocyanate (ISC-4), again a synthetic selenium mimic of PEITC, reduced both methyl and POB DNA damage in A/J mouse lung and liver tissues (Crampsie, M A et al. (2011) Cancer Prev. Res. 4: 1884-1894). Another promising lung cancer chemopreventive agent, indole-3-carbinol (I3C) was found to reduce $O^6$-mG in lung tissues but increased $O^6$-mG in liver tissues, potentially via increasing liver NNK metabolism (Morse, M A et al. (1990) Cancer Res. 50: 2613-2617). The study described herein is the first that characterized all three types of DNA damage in A/J mice and DHM appears to have a different mechanism relative to PEITC- and I3C-based lung cancer chemopreventive agents.

More characterizations have been performed on NNK-induced DNA damage in F344 rat lung and liver tissues and several studies have analyzed the impact of the chirality of NNAL as well (Lao, Y et al. (2006) Chem. Res. Toxicol. 19: 674-682; Upadhyaya, P et al. (2008) Chem. Res. Toxicol. 21: 1468-1476; Lao, Y et al. (2007) Chem. Res. Toxicol. 20: 235-245; Upadhyaya, P et al. (2009) Drug Metab. Dispos. 37: 1147-1151). Upadhyaya et al. demonstrated that (R)-NNAL preferentially generated PHB adducts, while (S)-NNAL and NNK produced mainly POB adducts. Although there has been no characterization of (R)- and (S)-NNAL-induced DNA damage in A/J mice, these two isomers appeared to have different metabolism and tumorigenicity (Upadhyaya, P et al. (1999) Carcinogenesis. 20: 1577-1582). It remains to be determined whether the PHB DNA damage in A/J mouse lung tissues mainly derives from (R)-NNAL and whether DHM selectively inhibits the activation of (R)-NNAL, leading to the preferential reduction in PHB DNA adducts in lung tissues. Alternatively, DHM may selectively enhance the detoxification of (R)-NNAL.

Because of the purported hepatotoxic risk of kava, the safety of (+)-DHM is of great importance. A/J mice continuously exposed to (+)-DHM at a dose of 0.5 mg/g of diet (at least ten times its minimum effective dose) for 17 weeks did not present with any adverse effects in the following parameters: average weekly bodyweight increase, average weekly food intake, clinical chemistry analyses of serum samples collected at Week 8 and Week 17, hematology analysis at Week 17, final bodyweight, relative weight of heart, lung, liver, kidney and spleen at Week 17, and the pathology of heart, lung, liver, kidney, spleen and pancreas at Week 17. Since the 0.5 mg/g dose appeared to be still below the maximum tolerated dose (MTD, which remains to be determined), (+)-DHM is expected to have a very wide safety margin as a lung cancer chemopreventive agent. One non-kavalactone compound in kava has been identified that recapitulates its hepatotoxic risk while (+)-DHM under the same conditions revealed no sign of hepatotoxic risk, suggesting that (+)-DHM is likely free of the hepatotoxic concern associated with kava (see, Example 5).

In summary, the data described herein support DHM as a potent and efficacious chemopreventive agent against NNK-induced lung tumorigenesis in A/J mice with a unique mechanism of action relative to several well-known lung cancer chemopreventive agents. Its sharp in vivo SAR suggests high target specificity, which is highly desirable to minimize adverse effects as reflected by its impressive safety profile. DHM is therefore a promising lung cancer chemopreventive agent.

Example 5

Flavokawains A and B in Kava, Not Dihydromethysticin, Potentiate Acetaminophen-Induced Hepatotoxicity in C57BL/6 Mice Abstract Anxiolytic kava products have been associated with rare but severe hepatotoxicity in humans. This adverse potential has never been captured in animal models and the responsible compound(s) remains to be determined. The lack of such knowledge greatly hinders the preparation of a safer kava product and limits its beneficial applications. In this study, the toxicity of kava as a single entity or in combination with acetaminophen (APAP) in C57BL/6 mice was evaluated. Kava alone revealed no adverse effects for long-term usage even at a dose of 500 mg/kg bodyweight. On the contrary a three-day kava pre-treatment potentiated APAP-induced hepatotoxicity, resulted in an increase in serum ALT and AST and increased severity of liver lesions. Chalcone-based flavokawains A (FKA) and B (FKB) in kava recapitulated its hepatotoxic synergism with APAP while dihydromethysticin (DHM, a representative kavalactone and a potential lung cancer chemopreventive agent) had no such effect. These results, for the first time, demonstrate the hepatotoxic risk of kava and its chalcone-based FKA and FKB in vivo and suggest that herb-drug interaction may account for the rare hepatotoxicity associated with anxiolytic kava usage in humans. Kava preparations, such as Fraction B described herein, which are free of flavokawains A and B, would have minimized risk and enriched beneficial components.

Introduction

Traditional kava is an aqueous extract of the roots of *Piper methysticum* and serves as a ceremonious and daily beverage or an herbal remedy for South Pacific islanders (Gounder, R. (2006) *Pac. Health Dialog* 13, 131-135). Kava had also been used clinically to treat mild and moderate anxiety based on results of numerous clinical trials (LaPorte, et al. (2011) *Hum. Psychopharmacol.* 26, 102-111; Sarris, et al. (2009) *Hum. Psychopharmacol.* 24, 41-48; Sarris, et al. (2009) *Psychopharmacology (Berl)* 205, 399-407; Pittler, M. H., and Ernst, E. (2000) *J. Clin. Psychopharmacol.* 20, 84-89). Anxiolytic kava was typically prepared as an organic extract of kava root with ethanol or acetone, instead of the traditional aqueous preparation. Anxiolytic kava had been banned in Europe and a few other countries since 2002 because of its risk to induce hepatotoxicity and it is listed on the USA FDA advisory board (Teschke, R., and Wolff, A. (2009) *Dig. Liver Dis.* 41, 891-901; Teschke, et al. (2013) *Phytother. Res.* 27, 472-474), but Germany's Federal Administrative Court negated the ban in June 2014 (Carreno, et al. (2014) *FRATINIVERGANO—European Lawyers* 13, 2-5).

Various causes have been proposed for kava's hepatotoxic risk but none have been validated so far. First of all, in response to high demand, anxiolytic kava may have included non-root toxic plant parts (Schulze, et al. (2003) *Phytomedicine* 10, 68-73). It has also been postulated that some kava roots were not properly dried, resulted in hepatotoxin contamination (Anke, J., and Ramzan, I. (2004) *Planta Med.* 70, 193-196). Usage of non-traditional cultivars could be another cause; different kava cultivars have diverse chemical profiles while traditional kava is prepared from only a few of them (Anke, J., and Ramzan, I. (2004) *Planta Med.* 70, 193-196; Lebot, et al. (2014) *Food Chem.* 151, 554-560). Due to preparation difference, traditional and anxiolytic kavas have distinct composition profiles (Shaik, et al. (2009) *Bioorg. Med. Chem. Lett.* 19, 5732-5736; Leitzman, et al. (2014) *Cancer Prev. Res. (Phila)* 7, 86-96), which may impose different hepatotoxic risks as well. Furthermore ~90% of the purported hepatotoxic cases associated with kava usage involved concomitant consumption of other drugs or dietary supplements (W. H. Organization (2007) Assessments of the risk of hepatotoxicity with kava products. *WHO Document Production Service*; Teschke, R., et al. (2008) *Eur. J. Gastroenterol. Hepatol.* 20, 1182-1193), suggesting that kava's hepatotoxic risk may be mediated via herb-herb or herb-drug interactions.

In addition to kava's anxiolytic benefit, one epidemiological survey suggested that traditional kava usage may be able to reduce cancer risk (Steiner, G. G. (2000) *Hawaii Med. J.* 59, 420-422), which was supported by results from several laboratory animal tumorigenesis models (Leitzman, P., et al. (2014) *Cancer Prev. Res. (Phila)* 7, 86-96; Johnson, et al. (2011) *Am. J. Chin. Med.* 39, 727-742; Johnson, et al. (2008) *Cancer Prev. Res. (Phila)* 1, 430-438; Triolet, et al. (2012) *Nutr. Cancer* 64, 838-846; Zi, X., and Simoneau, A. R. (2005) *Cancer Res.* 65, 3479-3486; Narayanapillai, et al. (2014) *Carcinogenesis* 35(10), 2365-72). Moreover despite its ban and being on USA FDA's advisory list, kava consumption has experienced a global resurgence based on the amount of kava exported from the major kava producing nations (The Republic of Vanuatu, Fiji, and Tonga) between 2008 and 2013 (Martin, et al. (2014) Measuring the chemical and cytotoxic variability of commercially available kava. *Plos One*, Accepted). With the recent overturn of the kava ban in Germany, its usage is expected to increase further globally. Our recent metabolomics and cellular cytotoxicity analyses of an array of current commercial kava products revealed that they were diverse in chemical profile and cellular cytotoxicity (Martin, et al. (2014) *Plos One*, 9(11): e111572. doi:10.1371/journal.pone.0111572), and likely distinct in their health benefit and risk.

Considering the increasing human exposure and the diverse chemical composition of current kava products, the hepatotoxic risk of kava needs to be clarified and the responsible chemicals need to be identified, which is the focus of this study. The results showed that kava was safe when given alone but significantly enhanced acetaminophen (APAP)-induced hepatotoxicity in C57BL/6 mice. Chalcone-based flavokawains A (FKA) and B (FKB) recapitulated kava's potentiation of APAP-induced hepatotoxicity while dihydromethysticin (DHM) lacked such a risk.

Abbreviations acetaminophen, APAP; flavokawain A, FKA; flavokawain B, FKB; dihydromethysticin, DHM; analysis of variance, ANOVA; alanine aminotransferase, ALT; aspartate aminotransferase, AST; polyethylene glycol-400, PEG-400.

Materials and Methods

Chemicals and Reagents

An ethanolic extract of the wild crafted kava root from Vanuatu was purchased from Gaia Herbs, Inc (Brevard, N.C., standardized to 150 mg/mL total kavalactones). DHM was purified from this kava product using normal phase silica gel chromatography as described earlier (Narayanapillai, et al. (2014) *Carcinogenesis* 35(10), 2365-72). FKA and FKB were synthesized and characterized following an established procedure (Johnson, et al. (2011) *Am. J. Chin. Med.* 39, 727-742). Kava and all compounds were completely dried under vacuum to remove any solvent residue. APAP was purchased from Sigma Aldrich (Mo., St Louis). The desired drug formulations were prepared by mixing kava or pure compounds with PEG-400 and stored at 4° C. until use.

Animal Study Design

All animal studies were performed in compliance with Institutional Animal Care and Use Committee at the University of Minnesota approvals and guidelines. Six week-old female C57BL/6J mice (Jackson Laboratories, ME) were housed at specific pathogen-free animal facilities of Research Animal Resources, University of Minnesota with free access to standard rodent food and water. All mice were acclimatized for one week before being used for experiments. Mice were gavaged with dose formulations at the indicated doses and times, euthanized by $CO_2$ overdosing with necropsy performed by experienced researchers.

The long-term study was designed to evaluate the hepatotoxicity of kava alone. C57BL/6 mice were randomized (n=4). Mice in the control group were given PEG-400 (200 µL) on a daily basis via gavage, six days a week, for 14 weeks. Mice in the kava treatment group were given kava at a dose of 500 mg/kg bodyweight on a daily basis via gavage, six days a week, for 14 weeks. The chosen kava dose was based on the recent safety studies of another kava product performed by the National Toxicology Program (National Toxicology, P. (2012) *Natl. Toxicol. Program Tech. Rep. Ser.* 1-186). Mouse bodyweight was measured once a week. Upon necropsy, final bodyweight was measured and serum from each mouse was analyzed for alanine aminotransferase (ALT) and aspartate aminotransferase (AST), two major biomarkers of liver function.

The short-term combination studies were designed to evaluate the potential synergism of kava and its chemicals to APAP induced hepatotoxicity. C57BL/6 mice were randomized (8-15 mice per group) and were administered with PEG-400 (200 μL), kava (500 mg/kg bodyweight), DHM or FKA and FKB in PEG-400 (200 μL) at the indicated doses daily via oral gavage for two days. On the third day, mice in the respective groups were co-administered with APAP (800 mg/kg bodyweight) in PEG-400 (200 μL). Bodyweight was recorded daily. Necropsies were performed 24 hours after the last gavage by experienced researchers. Serum from each mouse was analyzed for ALT and AST. Livers were collected and preserved in 10% neutral buffered formalin. Appropriately fixed tissues were processed into paraffin blocks using standard histological techniques, and 5 μm sections were cut and stained with hematoxylin and eosin (H&E). Histological slides were examined using light microscopy by an experienced A.C.V.P board certified pathologist (M.G. O'S.) under blinded conditions, with liver lesions graded on a 0 to 4 scale based on the extent of necrosis (0=absent, 1=minimal, 2=mild, 3=moderate, 4=severe).

Statistical Analysis

The clinical chemistry data were reported as mean±SD (n=4-15). For the long-term kava alone study, the two-tailed Student t-test was used to compare the means between the control and treatment groups. p-value≤0.05 was considered statistically significant. One-way analysis of variance (ANOVA) was used to compare the means among different groups in the short-term combination studies. Dunnett's test was used for comparisons of APAP and other treatment groups when the one-way ANOVA analysis was statistically significant. p-value≤0.05 was considered statistically significant. All analyses were conducted in GraphPad Prism 4 (GraphPad Software, Inc. La Jolla, Calif.).

Results

Kava Alone Did not Affect Mouse Growth and Induced No Signs of Hepatotoxicity.

Figure 23A:
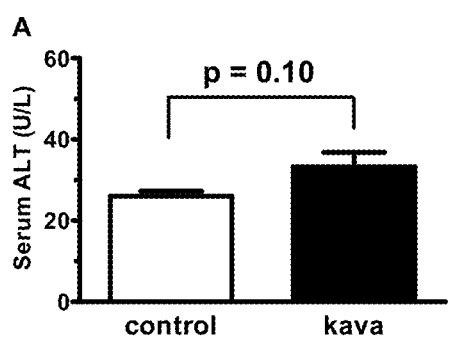
FIGS. 23A-23B. The effect of 14-week daily kava treatment (500 mg/kg bodyweight) via gavage on mouse serum ALT (FIG. 23A) and AST (FIG. 23B). p values were given with comparison between the control group (n=4) and kava treatment group (n=4) using the two-tailed Student t-test.
Figure 23B:
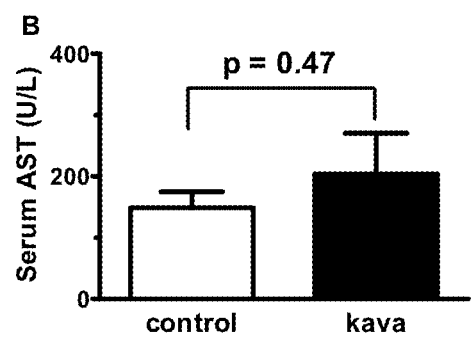

At the tested dose (500 mg/kg bodyweight), daily kava treatment did not affect mouse growth (data not shown). There were also no statistically or biologically significant differences between control and kava-treated mice with respect to ALT and AST (FIGS. 23A and 23B).

Kava Enhanced APAP-Induced Hepatotoxicity in C57BL/6 Mice.

Figure 24A:
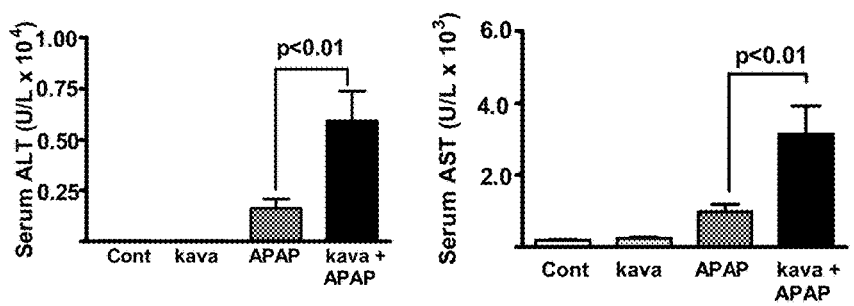
FIGS. 24A-24C. The effect of 3-day daily kava treatment (500 mg/kg bodyweight) via gavage on mouse serum ALT and AST and liver lesions with/without APAP treatment (800 mg/kg bodyweight) via gavage.
Figure 24B:
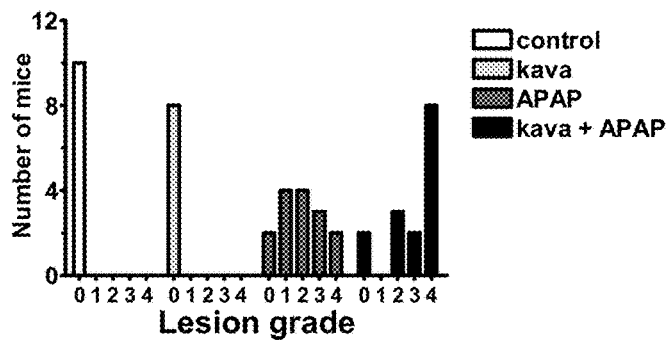
Figure 24C:
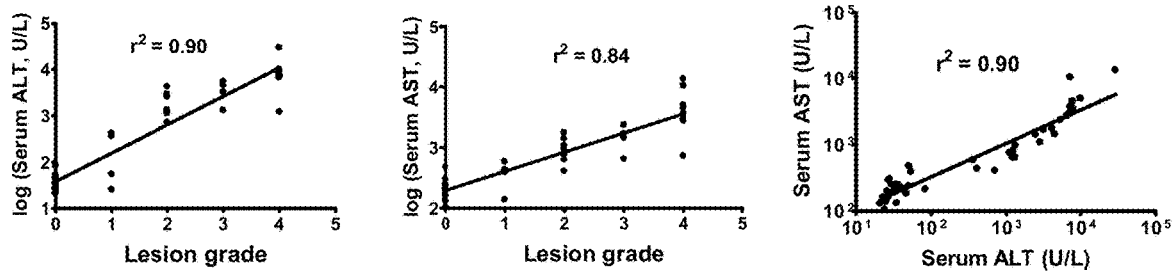

Since ~90% of the human kava hepatotoxic cases involved concurrent consumption of other medications or dietary supplements (W. H. Organization (2007) Assessments of the risk of hepatotoxicity with kava products. *WHO Document Production Service*; Teschke, R., et al. (2008) *Eur. J. Gastroenterol. Hepatol.* 20, 1182-1193), herb-drug interactions may contribute to kava's hepatotoxic risk. Based on this and on a recent report that kava enhanced the toxicity of APAP in vitro (Yang, X., and Salminen, W. F. (2011) *Phytomedicine* 18, 592-600), this study was designed to evaluate the effect of kava on APAP-induced hepatotoxicity in vivo. The treatment regimen was designed to mimic potential scenarios in humans—kava was consumed on a daily basis while APAP was used occasionally. As expected kava treatment alone had no effect on ALT and AST while APAP treatment significantly increased serum ALT and AST activities (FIG. 24A). Kava and APAP combination caused further increase in serum ALT and AST activities (~3 fold increase relative to APAP alone, FIG. 24A), and these increases were statistically significant in comparison to APAP treatment alone. Histopathological analyses of the liver tissues revealed no lesions in control and kava treated mice (FIG. 24B), confirming the lack of hepatotoxicity by kava treatment alone. The lesions from APAP-treated mice evenly distributed among different severity categories (0 being no lesion and 4 being the highest grade lesion) while kava and APAP combination markedly increased the number of mice with the highest liver lesion (FIG. 24B), supporting the notion that the increases in ALT and AST activities were biologically significant. These clinical chemistry data and histopathological findings for the first time demonstrate that kava enhanced APAP-induced hepatotoxicity in vivo, and may reflect the purported kava hepatotoxicity cases in humans. The histopathological lesion severity also nicely correlated positively with the clinical chemistry results (FIG. 24C). Therefore only clinical chemistry was performed in subsequent studies.

DHM Did not Potentiate APAP-Induced ALT and AST while FKB Increased Both.

Figure 25:
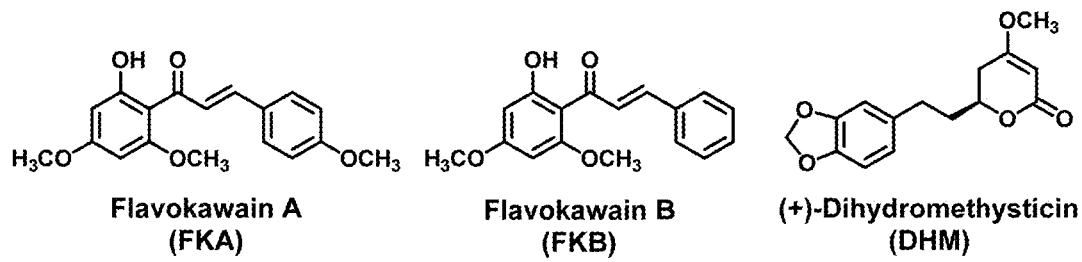
FIG. 25. Chemical structures of flavokawains A, B, and dihydromethysticin.
Figures 26A, 26B:
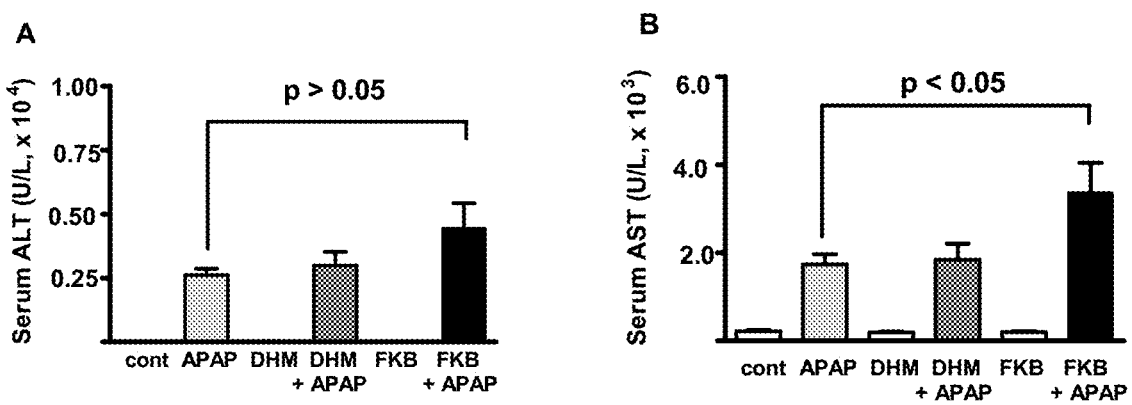
FIGS. 26A-26B. The effect of 3-day daily DHM (37.5 mg/kg) or FKB (11.5 mg/kg) via gavage on mouse serum ALT and AST with/without APAP treatment. Comparisons were made with APAP treatment group by Dunnett's test when ONE-WAY ANOVA was statistically significant (n=6-15).

This experiment was designed to explore the potential of DHM and FKB (FIG. 25) to synergize the hepatotoxicity of APAP following the same kava and APAP co-treatment regimen. Thirteen chemicals have been isolated and quantified from the kava product used in this study with no detection of pipermethystine (Leitzman, P., et al. (2014) *Cancer Prev. Res.* (*Phila*) 7, 86-96). DHM and FKB were selected for this initial evaluation because they are representatives of kavalactones and chalcones respectively, two major classes of chemicals in kava. In addition DHM has been recently demonstrated to potently and effectively block NNK-induced lung tumorigenesis in mice (Leitzman, P., et al. *Cancer Prev. Res.* (*Phila*) 7, 86-96) while FKB has been identified as the most cytotoxic compound in kava to various cancerous cells (Shaik, et al. (2009) *Bioorg. Med. Chem. Lett.* 19, 5732-5736; Jhoo, et al. (2006) *J. Agric. Food Chem.* 54, 3157-3162). The dosages for DHM (37.5 mg/kg) and FKB (11.5 mg/kg) were based on their abundance (7.5% and 2.3% respectively) in this kava product at a dose of 500 mg/kg (Leitzman, et al. (2014) *Cancer Prev. Res.* (*Phila*) 7, 86-96). DHM and FKB individually caused no effect on serum ALT and AST (FIGS. 26A and 26B). DHM had no effect on serum ALT and AST as well when combined with APAP (FIGS. 26A and 26B). FKB on the other hand when combined with APAP moderately increased the serum levels of ALT and AST, and the increase in AST was statistically significant (FIGS. 26A and 26B), suggesting that FKB contributes to kava's potentiation of APAP-induced hepatotoxicity.

The Combination of Flavokawain A (FKA) and FKB Dose-Dependently Enhanced APAP-Induced Hepatotoxicity.

Figure 27A:
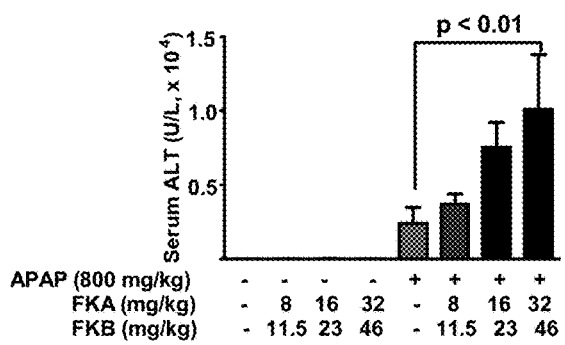
FIGS. 27A-27D. The dose-response effect of 3-day daily FKA and FKB via gavage on mouse serum ALT, AST and livers with/without APAP treatment.
Figure 27B:
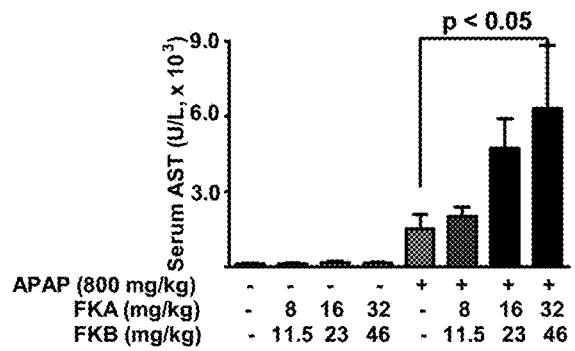
Figure 27C:
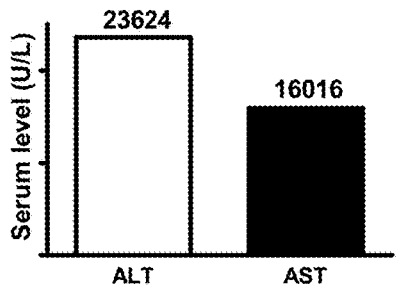
Figure 27D:
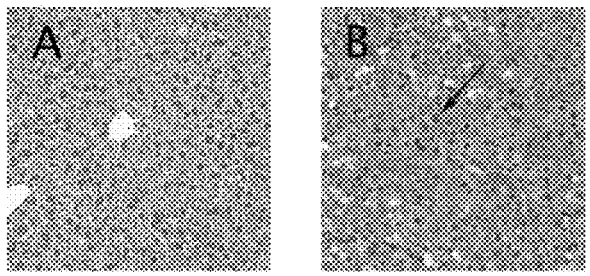

Given that the kava product used in this study contains flavokawain A (FKA) of similar abundance as FKB (FIG. 25), this experiment was designed to evaluate the dose-response effect of FKA and FKB together on APAP's hepatotoxicity following the same treatment regimen. The final dosages of FKA and FKB were 1, 2 and 4 times their abundance (1.6% and 2.3% respectively) of a kava dose at 500 mg/kg bodyweight. FKA and FKB together did not induce any changes on serum ALT and AST at the three tested dosages (FIGS. 27A and 27B). When combined with APAP, FKA and FKB dose-dependently potentiated the increase in ALT and AST induced by APAP (FIGS. 27A and 27B). Of note, one mouse with the treatment of the highest dose of FKA and FKB in combination with APAP died~0.5-2 hours before necropsy (i.e., 22 to 23.5 hours after the combined dose of APAP with FKA and FKB). This was the only mouse among all the studies that died before necropsy. Its serum ALT and AST levels were the highest among all mice (FIG. 27C), and 2-3 times higher than the next highest values. Histopathological examination revealed multifocal and coalescing acute centrilobular necrosis in the liver of this mouse (FIG. 27D, panel B), whereas livers from a control mouse (FIG. 27D, panel A) and a mouse treated with FKA and FKB alone (not shown) were histologically within normal limits. These data suggest that severe hepatotoxicity likely contributed to its early death.

DISCUSSION

Kava has demonstrated anxiolytic activity in the clinic and potentially reduces cancer risk in humans. On the other hand, kava usage has been speculated to be associated with rare but severe hepatotoxicity. Various mechanisms have been proposed and different chemicals have been postulated with no confirmation. Given kava's global resurgence and the diverse chemical composition among current kava products, it is urgent and important to recapitulate kava's hepatotoxicity in an in vivo model, which can help identify the responsible chemicals and guide the development of strategies to minimize and ideally eradicate such an adverse potential.

The results from this study demonstrated that kava when administered alone via gavage in C57BL/6 mice induced no adverse effect even at a fairly high dose (500 mg/kg bodyweight daily) in a chronic manner, as reflected in mouse growth and serum levels of ALT and AST (FIG. 23). These results are consistent with the results from many early studies (DiSilvestro, et al. (2007) Food Chem. Toxicol. 45, 1293-1300; Guo, L., (2009) Food Chem. Toxicol. 47, 433-442; Guo, et al. (2010) Food Chem. Toxicol. 48, 686-696; Sorrentino, et al. (2006) Phytomedicine 13, 542-549). On the other hand, kava significantly potentiated the hepatotoxicity of APAP in C57BL/6 mice as indicated by the increase in serum ALT and AST, and the increased severity of liver lesions (FIG. 24). The treatment regimen was designed to mimic potential circumstances among human kava users that kava would be consumed on a daily basis while other medications, APAP in this case, were used occasionally when needed. Since the majority of kava-associated hepatotoxic cases consumed other medications or dietary supplements concomitantly, the results from this study may have direct indication to the observed hepatotoxicity among kava users. It remains to be determined whether kava usage can potentiate the hepatotoxic risk of other medications or hepatotoxins, such as alcohol consumption. It also remains to be determined whether other kava treatment regimens, such as prolonged kava usage or in a fasted stage (recommended for traditional kava usage), may potentiate its hepatotoxic risk even at lower kava dosages.

With the C57BL/6 mouse model that captures kava's hepatotoxic risk in vivo, the potential responsible compound(s) were investigated. The results demonstrated that a chalcone-based compound in kava, FKB, moderately potentiated APAP's hepatotoxicity while DHM, a representative of kavalactones in kava, lacked such a risk when they were evaluated at a dose equivalent to kava at a dose of 500 mg/kg bodyweight (FIG. 26). As the kava product contains FKA, an analog of FKB, at similar abundance, the combination of FKA and FKB were evaluated, which dose-dependently enhanced APAP-induced hepatotoxicity (FIG. 27). Indeed the one mouse that died early, and which had the highest ALT and AST levels (FIG. 27C) reflecting extensive acute hepatocellular necrosis (FIG. 27D, panel B), was in the APAP co-treatment group at the highest dose of FKA and FKB. These data overall indicate that FKA and FKB are the responsible compounds in kava that potentiate APAP-induced hepatotoxicity while DHM is free of this risk. Besides FKA and FKB, flavokawain C (FKC) has been reported in other kava products (Lebot, et al. (2014) Food Chem. 151, 554-560) but was not detectable in the kava product used in this study. FKC might be another compound responsible for hepatotoxicity.

The recent analysis of a set of kava products on the current market demonstrates that the abundance of FKA and FKB can vary~20 fold (Martin, et al. (2014) Plos One, 9(11): e111572. doi:10.1371/journal.pone.0111572). Similarly a recent study analyzed the abundance of FKA, FKB, and FKC in different kava cultivars (Lebot, et al. (2014) Food Chem. 151, 554-560). Cultivars not recommended for traditional use were found to contain higher abundance of FKA, FKB, and FKC than the traditionally consumed cultivars (Lebot, et al. (2014) Food Chem. 151, 554-560). Further studies therefore are warranted to evaluate whether cultivars or kava products with higher content of FKA, FKB, and FKC would impose a higher hepatotoxic risk. Future studies are also needed to elucidate the molecular mechanisms of the observed hepatotoxicity enhancement, such as the depletion of glutathione (Zhou, et al. (2010) FASEB J. 24, 4722-4732). Such knowledge will help guide the preparation of kava products for human use with higher health benefit and minimal adverse effects.

Example 6

Figure 28A:
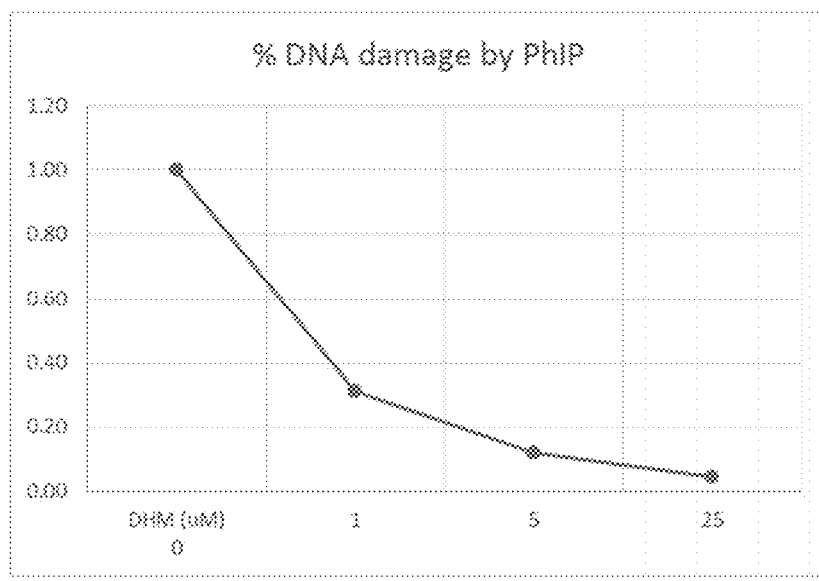
FIGS. 28A-28B. The dose-response effect of dihydromethysticin on reducing 2-Amino-1-methyl-6-phenylimidazo[4,5-b]pyridine (FIG. 28A) and benzo(a)pyrene-induced DNA damage (FIG. 28B) in cell culture Hepe1c1c7 cells.
Figure 28B:
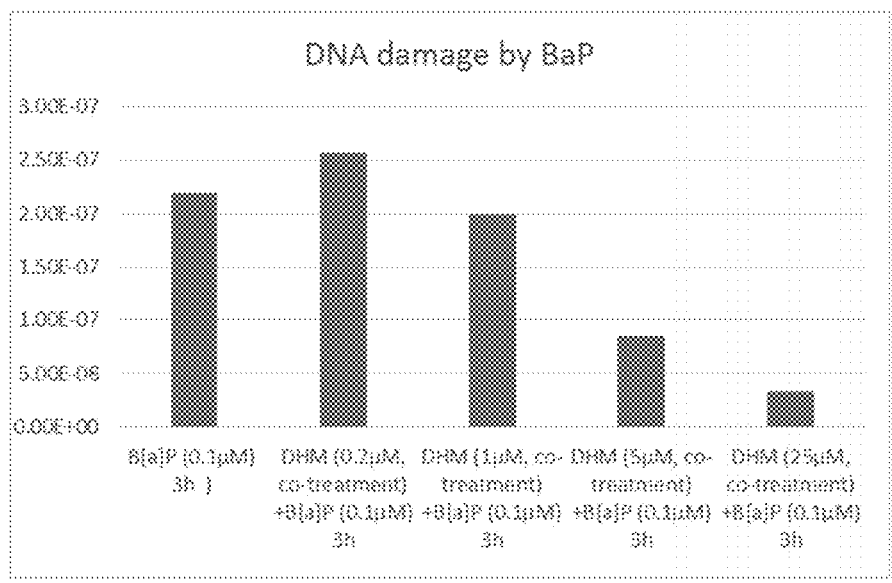

Dihydromethysticin Effectively Blocks 2-amino-1-methyl-6-phenylimidazo(4,5-b)pyridine (PhIP) and benzo (a)pyrene (BaP)-Induced DNA Damage
Introduction The goal of this study was to explore the potential scope of dihydromethysticin in blocking/reducing different carcinogen-induced DNA damage and detoxifying such carcinogens. 2-Amino-1-methyl-6-phenylimidazo[4,5-b]pyridine (PhIP) is one of the most abundant heterocyclic amines in cooked meats (Ni W, (2008) Journal of agricultural and food chemistry. 56(1):68-78.) and possibly the most potent carcinogen among them, particularly for colon cancer, prostate cancer and breast cancer (Nishikawa A, (2005). Toxicological sciences: an official journal of the Society of Toxicology. 84(2):243-8.). Benzo(a)pyrene (BaP) is a representative polyaromatic hydrocarbon-based carcinogen in cigarette smoke and is present in various industrial/motor exhaust/waste. BaP is a human carcinogen to lung, stomach and other tissues. A rodent liver cancer cell line was used in these studies. Briefly, the hepe1c1c7 cells were co-treated with dihydromethysticin (1, 5, and 25 μM) and PhIP (10 μM) for 24 hours with DNA isolated and PhIP-based DNA damage quantified (FIG. 28A). It is clear that dihydromethysticin effectively and dose-dependently reduced PhIP-induced DNA damage, demonstrating its efficacy in blocking carcinogen-induced DNA damage and indicating its detoxifying function and cancer chemopreventive potential against colon, prostate and breast cancer. Similarly the cells were co-treated with dihydromethysticin (1, 5, and 25 μM) and BaP (0.3 μM) for 3 hours with DNA isolated and BaP-based DNA damage quantified (FIG. 28B). Dihydromethysticin effectively and dose-dependently reduced BaP-induced DNA damage, demonstrating its efficacy in blocking carcinogen-induced DNA damage and indicating its detoxifying function and cancer chemopreventive potential against lung cancer and stomach cancer.

Example 7

The following illustrate representative pharmaceutical dosage forms, containing 'Compound X', for therapeutic or prophylactic use in humans. As described herein, Compound X may represent a compound described herein, for example, such as dihydromethysticin, methysticin, dihydrokavain, kavain, desmethoxyyangonin and 11-methoxyyangonin.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Aerosol 1 | mg/can |
|---|---|
| Compound X= | 10.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (viii) Aerosol 2 | mg/can |
|---|---|
| Compound X= | 5.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (ix) Aerosol 3 | mg/can |
|---|---|
| Compound X= | 2.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating cancer, preventing cancer, preventing tumorigenesis, reducing DNA damage, reducing protein damage, detoxifying physical carcinogens, and/or detoxifying chemical carcinogens in a mammal in need of such treatment comprising, administering to the mammal a composition comprising 11-methoxyyangonin, flavanone:

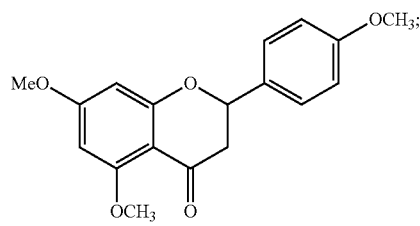

and
dihydromethysticin, wherein the composition comprises less than 0.3% by weight of a bornyl ester of cinnamic acid of the formula:

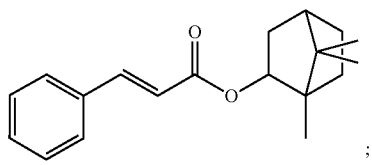 [SMILES: CC1(C)C2CCC1(C)C(OC(=O)/C=C/c1ccccc1)C2]

comprises less than 0.3% by weight of flavokawain B; and comprises less than 0.3% by weight of flavokawain A.

2. The method of claim 1, which is a method for treating cancer.

3. The method of claim 1, which is a method for preventing cancer.

4. The method of claim 1, which is a method for preventing tumorigenesis.

5. The method of claim 1, which is a method for reducing DNA damage, reducing protein damage, detoxifying physical carcinogens, and/or detoxifying chemical carcinogens.

6. The method of claim 1, wherein the cancer is lung cancer, prostate cancer, skin cancer, melanoma, genitourinary cancer, colon and rectum cancer, breast cancer, ovary cancer, esophageal cancer, pancreatic cancer, urinary bladder cancer, cervical cancer, liver cancer, kidney and renal cancer, head and neck cancer, brain cancer or hematological cancers.

7. The method of claim 1, wherein the DNA damage is a DNA adduct, and wherein the DNA adduct is selected from the group consisting of $O^6$-methylguanine, BaP, PhIP, POB and PHB adducts.

8. The method of claim 1, wherein the weight percent of dihydromethysticin in the composition is about 15±5%.

9. The method of claim 1, wherein the weight percent of the flavanone:

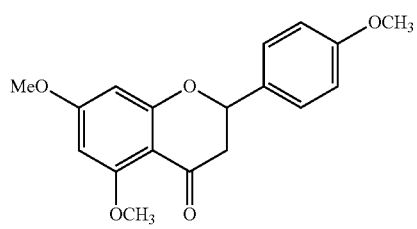 [SMILES: COc1ccc(C2CC(=O)c3c(OC)cc(OC)cc3O2)cc1]

in the composition is about 1.0±0.5%; and wherein the weight percent of 11-methoxyyangonin in the composition is about 0.8±0.5%.

10. The method of claim 1, wherein the composition further comprises at least one compound selected from the group consisting of methysticin, dihydrokavain, kavain and desmethoxyyangonin.

11. The method of claim 10, wherein the composition further comprises methysticin.

12. The method of claim 11, wherein the weight percent of methysticin in the composition is 6 d: 5%.

13. The method of claim 10, wherein the composition further comprises dihydrokavain.

14. The method of claim 13, wherein the weight percent of dihydrokavain in the composition is 30±5%.

15. The method of claim 10, wherein the composition further comprises kavain.

16. The method of claim 15, wherein the weight percent of kavain in the composition is about 29±5%.

17. The method of claim 10, wherein the composition further comprises desmethoxyyangonin.

18. The composition of claim 17, wherein the weight percent of desmethoxyyangonin in the composition is 12±5%.

19. The method of claim 1, wherein the composition is substantially free of pinostrobin, bornyl ester of 3,4-methylenedioxy cinnamic acid:

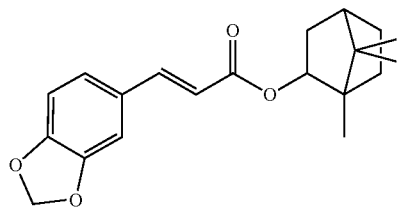

and/or
flavanone:

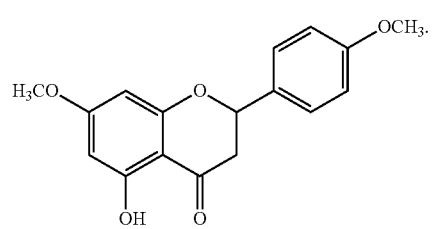 [SMILES: COc1ccc(C2CC(=O)c3c(O)cc(OC)cc3O2)cc1]

20. The method of claim 1, wherein the composition consists essentially of dihydromethysticin, 11-methoxyyangonin, desmethoxyyangonin, dihydrokavain, kavain, methysticin and flavanone:

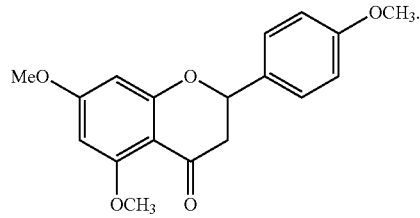

21. The method of claim 1, wherein the composition comprises a kava extract.

22. The method of claim 1, wherein the composition is formulated in a tablet, capsule, chewing gum, nano-emulsion, cream, wafer or gel.

23. The method of claim 1, wherein the 11-methoxyyangonin, flavanone, and dihydromethysticin are collectively present in the composition in an amount from 5 mg to 1000 mg.

24. The method of claim 1, wherein the 11-methoxyyangonin is present in the composition in an amount from 10 mg to 100 mg; and/or wherein the dihydromethysticin is present in the composition in an amount from 10 mg to 100 mg.

25. A method for treating anxiety in a mammal in need of such treatment comprising, administering to the mammal a composition comprising 11-methoxyyangonin, flavanone:

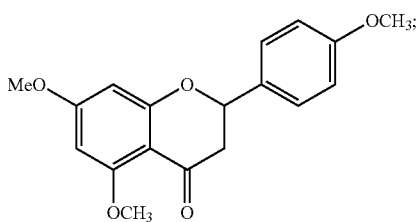

and
dihydromethysticin, wherein the composition comprises less than 0.3% by weight of a bornyl ester of cinnamic acid of the formula:

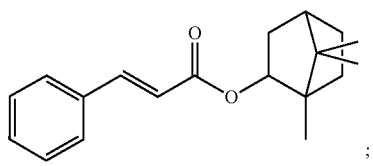 [SMILES: CC1(C)C2CCC1(C)C(OC(=O)/C=C/c1ccccc1)C2]

comprises less than 0.3% by weight of flavokawain B; and comprises less than 0.3% by weight of flavokawain A.

26. The method of claim 25, wherein the weight percent of dihydromethysticin in the composition is about 15±5%.

27. The method of claim 25, wherein the weight percent of the flavanone:

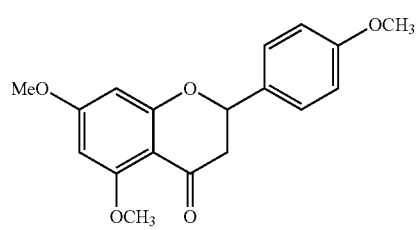 [SMILES: COc1ccc(C2CC(=O)c3c(OC)cc(OC)cc3O2)cc1]

in the composition is about 1.0±0.5%; and wherein the weight percent of 11-methoxyyangonin in the composition is about 0.8±0.5%.

28. The method of claim 25, wherein the composition further comprises at least one compound selected from the group consisting of methysticin, dihydrokavain, kavain and desmethoxyyangonin.

29. The method of claim 28, wherein the composition further comprises methysticin.

30. The method of claim 29, wherein the weight percent of methysticin in the composition is 6±5%.

31. The method of claim 28, wherein the composition further comprises dihydrokavain.

32. The method of claim 31, wherein the weight percent of dihydrokavain in the composition is 30±5%.

33. The method of claim 28, wherein the composition further comprises kavain.

34. The method of claim 33, wherein the weight percent of kavain in the composition is about 29±5%.

35. The method of claim 28, wherein the composition further comprises desmethoxyyangonin.

36. The composition of claim 35, wherein the weight percent of desmethoxyyangonin in the composition is 12±5%.

37. The method of claim 25, wherein the composition is substantially free of pinostrobin, bornyl ester of 3,4-methylenedioxy cinnamic acid:

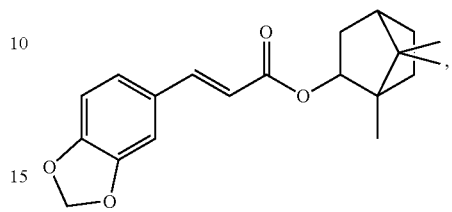

and/or
flavanone:

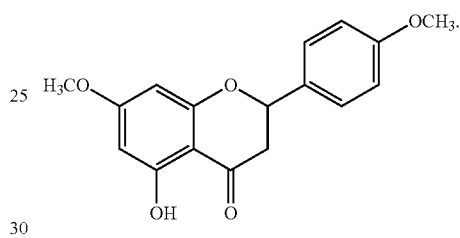

38. The method of claim 25, wherein the composition consists essentially of dihydromethysticin, 11-methoxyyangonin, desmethoxyyangonin, dihydrokavain, kavain, methysticin and flavanone:

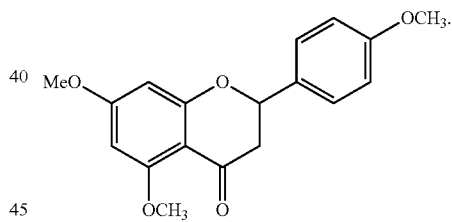

39. The method of claim 25, wherein the composition comprises a kava extract.

40. The method of claim 25, wherein the composition is formulated in a tablet, capsule, chewing gum, nano-emulsion, cream, wafer or gel.

41. The method of claim 25, wherein the 11-methoxyyangonin, flavanone, and dihydromethysticin are collectively present in the composition in an amount from 5 mg to 1000 mg.

42. The method of claim 25, wherein the 11-methoxyyangonin is present in the composition in an amount from 10 mg to 100 mg, and/or wherein the dihydromethysticin is present in the composition in an amount from 10 mg to 100 mg.

* * * * *

UNITED STATES PATENT AND TRADEMARK OFFICE
CERTIFICATE OF CORRECTION

PATENT NO. : 10,918,687 B2
APPLICATION NO. : 16/750812
DATED : February 16, 2021
INVENTOR(S) : Chengguo Xing et al.

Page 1 of 1

It is certified that error appears in the above-identified patent and that said Letters Patent is hereby corrected as shown below:

In the Claims

Column 71, Line 57, Claim 12, please delete "composition is 6 d: 5%." and insert -- composition is 6 ± 5%. -- therefor.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*